(12) United States Patent
Larsen et al.

(10) Patent No.: US 7,279,274 B2
(45) Date of Patent: Oct. 9, 2007

(54) METHOD FOR DIAGNOSING DIABETES IN A MAMMAL

(75) Inventors: Peter Mose Larsen, Odense S (DK); Stephen J. Fey, Aarhus C (DK); Allan E. Karlsen, Allerod (DK); Thomas Sparre, Frederiksberg C (DK); Jorn Nerup, Holte (DK)

(73) Assignee: Pride Proteomics A/S, Odense M (DK)

( * ) Notice: Subject to any disclaimer, the term of this patent is extended or adjusted under 35 U.S.C. 154(b) by 0 days.

(21) Appl. No.: 10/960,652

(22) Filed: Oct. 7, 2004

(65) Prior Publication Data

US 2006/0008881 A1    Jan. 12, 2006

Related U.S. Application Data

(63) Continuation of application No. 10/479,530, filed as application No. PCT/DK02/00368 on May 29, 2002.

(30) Foreign Application Priority Data

May 29, 2001 (DK) .............................. 2001 00852
Mar. 22, 2002 (DK) .............................. 2002 00446

(51) Int. Cl.
*C12Q 1/00* (2006.01)
*C12Q 1/68* (2006.01)
*G01N 33/53* (2006.01)
*C12P 11/00* (2006.01)
*A01N 37/18* (2006.01)
*C07K 16/00* (2006.01)
*C12N 5/16* (2006.01)

(52) U.S. Cl. .............................. 435/4; 435/7.1; 435/6; 435/130.1; 435/325; 514/2; 530/388.26

(58) Field of Classification Search .................... 435/6, 435/7.1, 325; 514/2; 530/388.26
See application file for complete search history.

(56) References Cited

U.S. PATENT DOCUMENTS 6,146,831 A * 11/2000 Davis et al. .................... 435/6

FOREIGN PATENT DOCUMENTS

WO    98 19271    5/1998
WO    01 01130    1/2001

OTHER PUBLICATIONS

Mose Larsen P. et al. "Proteome analysis of interleukin-1beta-induced changes in protein expression in rat islets of Langerhans." DIABETES, vol. 50, May 2001 pp. 1056-1063.
John N.E. et al. "Cytokine- or chemically derived nitric oxide alters the expression of proteins detected by two-dimensional gel eletrophoresis in neonatal rat islets of Langerhans." DIABETES, vol. 49, Nov. 2000, pp. 1819-1829.
Andersen H.U. et al. "Interleukin-1beta induced changes in the protein expression of rat islets: a computerized database." ELECTROPHORESIS, vol. 18, 1997, pp. 2091-2103.
Christensen U.B. et al. "Islet protein expression changes during diabetes development in islet syngrafts in BB-DP islet allografts." AUTIMMUNITY, vol. 32, 2000, pp. 1-15.

* cited by examiner

*Primary Examiner*—Rebecca E. Prouty
*Assistant Examiner*—Iqbal Chowdhury
(74) *Attorney, Agent, or Firm*—Merchant & Gould P.C.

(57) ABSTRACT

Provided are mammalian secreted and non-secreted diabetes mediating proteins, including protective and deleterious diabetes-mediating proteins, as well as polynucleotides encoding same, drug screening methods for identifying a test compound capable of altering the expression of a diabetes-mediating protein, and methods of preventing or ameliorating diabetes by administering a compound capable of the expression of a diabetes-mediating protein.

6 Claims, 74 Drawing Sheets

FIG. 1 NEONATAL BB-DP rat islets

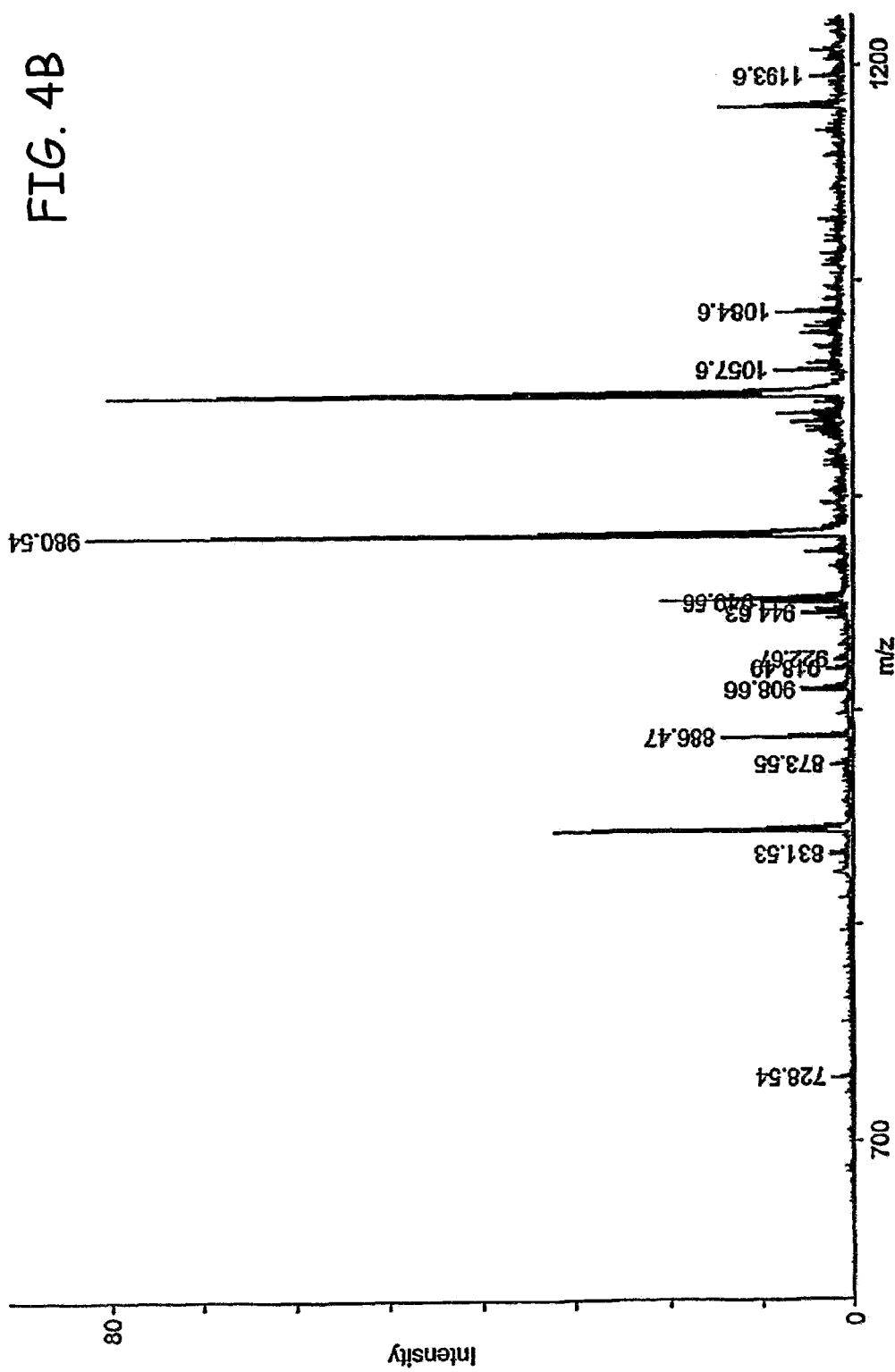

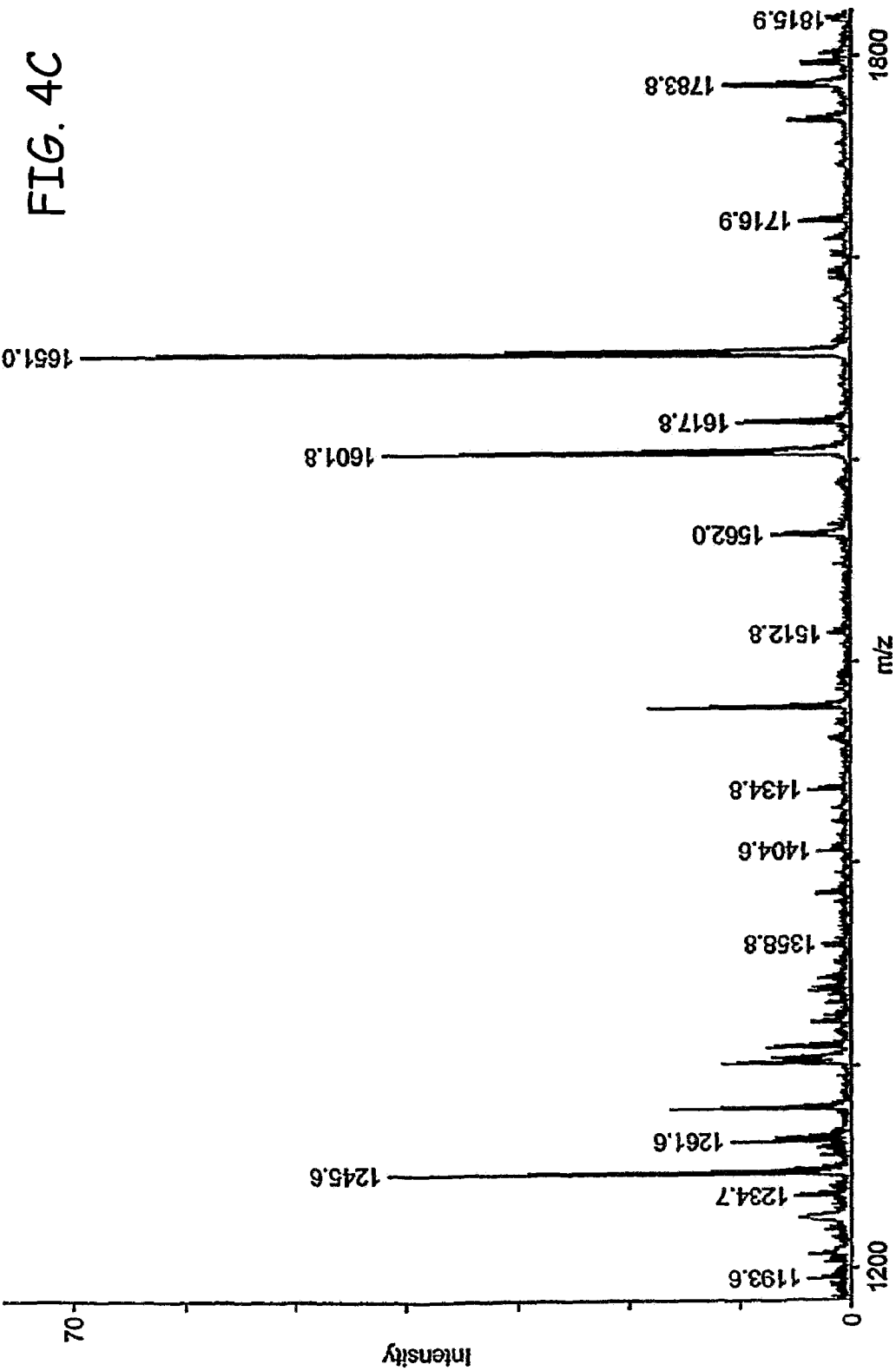

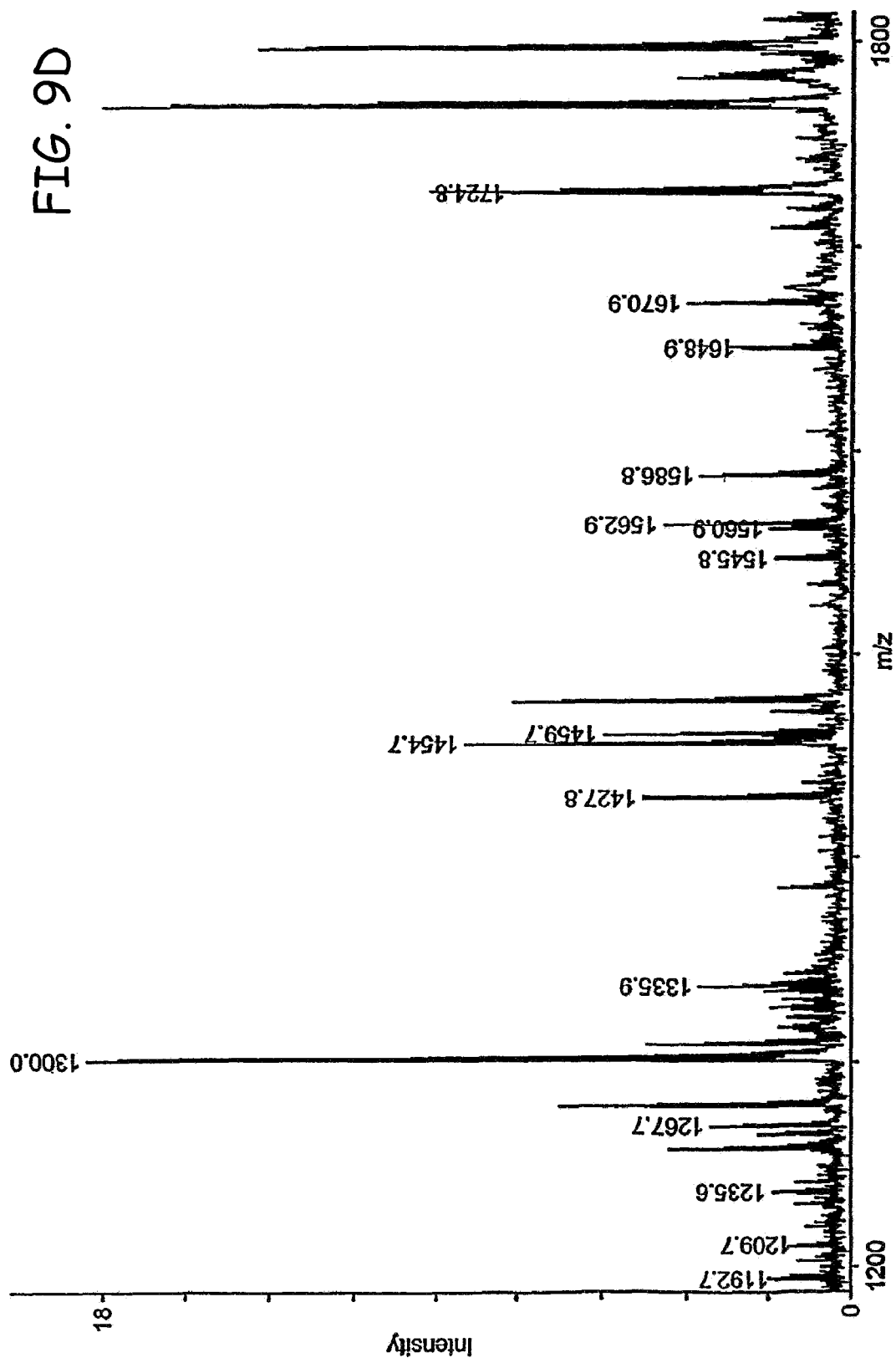

METHOD FOR DIAGNOSING DIABETES IN A MAMMAL

This application is a continuation of application Ser. No. 10/479,530, filed Dec. 1, 2003, which is a National Stage of PCT/DK02/00368 which application is incorporated herein by reference.

FIELD OF INVENTION

Proteome analysis has allowed for the identification of proteins and their association to diabetes. These proteins, in themselves, either up-regulated or down-regulated, are indicators of diabetes in a patient. The pattern of regulation of a grouping of these proteins also serves as an indicator of diabetes. These proteins can be used as targets for the treatment of diabetes or for treatment itself. The proteins were identified by monitoring IL-1β induced protein changes in diabetes prone mammalian islets of Langerhans.

BACKGROUND OF THE INVENTION

Type 1 Diabetes Mellitus is a multifactorial polygenetic autoimmune disease, where the insulin producing β-cells are selectively destroyed. The initiating events and precise mechanisms leading to selective β-cell destruction remains unknown. One current hypothesis [3] is that in genetically predisposed individuals the β-cells are influenced by factors from the internal or external environment which can damage the β-cells (e.g. cytokines, virus and chemicals) and then lead to release of β-cell specific proteins. During the destructive process IL-1β is released by macrophages in the islets and the cytotoxic effects of IL-1β on the β-cells results in production of free radicals (e.g. nitric oxide (NO.), super oxide ($O_2$.) and hydroxyl ($OH^-$) inside the β-cells. Free radicals and NO. are also produced in and secreted from macrophages in the islet infiltrate. The effects of free radicals are attempted scavenged by β-cell protective proteins (e.g. haeme oxygenases and manganese superoxide dismutase (MnSOD)) [25, 26]. A race between protective and destructive mechanisms is initiated, and when the destructive mechanisms exceed the protective mechanisms, the β-cells die [3].

Autoimmune insulin-dependent diabetes mellitus (T1DM) is caused by specific destruction of the insulin producing β-cells in the islets of Langerhans in the pancreas. During this process islets are infiltrated with macrophages and lymphocytes, releasing a mixture of cytokines, such as interieukin-1β (IL-1β), tumor necrosis factor-α (TNF-α) and interferon-γ (IFN-γ), which is specifically toxic to the β-cells. Cytokines have been demonstrated to induce free radicals such as nitric oxide (NO.), catalyzed by inducible nitric oxide synthase (INOS) and oxygen derived radical.

Development of Type 1 Diabetes Mellitus (T1DM) is characterized by mononuclear cell infiltration in the islets of Langerhans (insulitis) and selective destruction of the insulin producing β-cells [1, 2]. It is generally accepted that the autoimmune destruction of the β-cells result from interactions between various environmental factors and immune mechanisms in genetically susceptible individuals [3]. The very first events initiating the destructive process has not been described yet. Cytokines, in particular interleukin-1β (IL-1β), are known to be released within the islets in low concentrations by a limited number of nonendocrine cells in sufficient quantities to inhibit and modulate β-cell function in vitro [4]. In response to low concentrations of IL-1β islets increase insulin release but insulin release is decreased at high concentrations of IL-1β. Furthermore IL-1β influences many important cellular functions such as decreasing DNA synthesis, decreasing protein synthesis and intracellular energy production and induction of apoptosis. Many of these effects are mediated through induction of the inducible NO syntase (INOS) and its product, the free radical nitric oxide (NO.) [5]. The present investigators hypothesize that the β-cell when exposed to IL-1β initiates a self protective response in competition with a series of deleterious events, and that in β-cells the deleterious prevail [3]. In support of this, overexpression of scavengers of free radicals such as catalase and glutatione peroxidase reduces the deleterious effects of cytokines on β-cells [6].

The present investigators have recently described a similar behavior of Wistar Furth (WF) rat islets exposed to IL-1β in vitro [7]. IL-1β induced significant changes in expression level of 105 proteins in WF islets where both protective proteins e.g. such as galectin-3 and HSP70 are up-regulated and deleterious protein changes e.g. mortalin and lamin A and B1, were identified. In addition proteins involved in mitochondrial energy production were suppressed e.g. adenylate kinase and mitochondrial ATP synthase regulatory subunit B [7].

The BioBreeding diabetes prone (BB-DP) rat spontaneously develops a diabetic syndrome with many characteristics common with human T1DM [8]. Originally the BB-DP rat strain has been breed from a WF rat colony [9]. Strain-dependent variations in β-cell sensitivity to IL-1β effects have been demonstrated in vitro and in vivo [10] [11]. Islets isolated from grown Norway rats were less sensitive to IL-1β compared to Wistar Furth (WF), Lewis-Scripps (LS) and BB (both diabetes prone (DP) and diabetes resistant (DR)) rats. The BB-DP rat islets produce lower protective stress responses (HSP70) than the diabetes resistant BB rat which might promote enhanced vulnerability and β-cell destruction [12]. The present investigators have previously shown that there is no difference in nitric oxide (NO.) production and 24 hour accumulated insulin release in BB-DP and WF islets in response to exposure to 150 pg/ml IL-1β for 24 hours [13]. The higher resistance to IL-1β induced inhibition of β-cell function in vitro and in vivo in BN rat islets was associated with lower expression of inducible nitric oxide synthase (INOS) compared to Wistar Kyoto and Ls rats [11].

The present investigators previously demonstrated that IL-1β induces reproducible and statistically significant changes in the expression level of 82 protein spots in BB-DP rat islets of Langerhans in vitro out of a total of 1.815 protein spots visualized by 2 dimensional gel electrophoresis. Twenty-two protein spots were up-regulated and 60 protein spots down-regulated [13].

Recently, the present investigators have separated approximately 1.900 protein spots according to molecular weight and isoelectric point (pI) by high resolution 2 dimensional gel electrophoresis of WF rat islets of Langerhans [14]. One hundred and five of these protein spots changed expression levels after IL-1β incubation in vitro and the majority of these proteins have now been identified by mass spectrometry. The identified proteins were classified into the following functional groups (in brackets number of different proteins): a) energy transduction and redox potentials (n=14), b) glycolytic enzymes (n=10), c) protein synthesis (n=5), d) chaperones, protein folding and translocation (n=19), e) signal transduction, regulation, differentiation and apoptosis (n=9) suggesting broad variety of pathways involved in IL-1β toxicity on islets [7].

SUMMARY OF THE INVENTION

The present investigators have demonstrated that the combination of 2 dimensional gel electrophoresis and mass spectrometry is a powerful tool in the identification of proteins involved in the cytotoxic effects of IL-1β in neonatal BB-DP rat islets. This study demonstrates that IL-1β exposure of BB-DP and WF rat islets involves essentially the same pathways and results in equal production of NO and accumulated insulin release over 24 hours and the same final result after IL-1β exposure, necrosis and apoptosis although some of the involved proteins are slightly different in the two rat strains.

Moreover, the present investigators have examined the effects of IL-β on BB-DP rat islets in vitro as a simplified model for β-cell destruction in the pathogenesis of T1DM and found that a preponderance of identified changes in protein expression relate to cytokine mediated β-cell destruction and development of T1 DM.

Thus, the present investigators have identified proteins associated with diabetes by detecting the absolute or relative presence of the proteins of tables 1, 2 and 3 in a biological sample. Typically, the biological sample is selected from the group consisting of urine, blood, CSF, saliva, lymphatic fluids, and tissue. Suitably, the tissue is pancreatic islets of Langerhans.

Proteome analysis applied to BB-DP rat islets exposed to IL-1β reveals insight into mechanisms responsible for β-cell destruction at the protein level as well as identifying proteins of relevance in the treatment of diabetes. Furthermore comparison of protein changes identified by proteome analysis in WF and BB-DP rat islets exposed to IL-1β identify proteins and pathways involved in β-cell destruction specific for the diabetes prone BB rat.

DESCRIPTION OF THE FIGURES:

FIGS. 4B-4D represent enlarged regions of FIG. 4A for protein I 266 such that particular peaks may be readily identified.

FIGS. 9B-9E represent enlarged regions of FIG. 9 A for protein I 683 such that particular peaks may be readily identified.

FIGS. 11B-11H represent enlarged regions of FIG. 11A for protein I 8264 such that particular peaks may be readily identified.

DETAILED DESCRIPTION OF THE INVENTION

Figure 1:
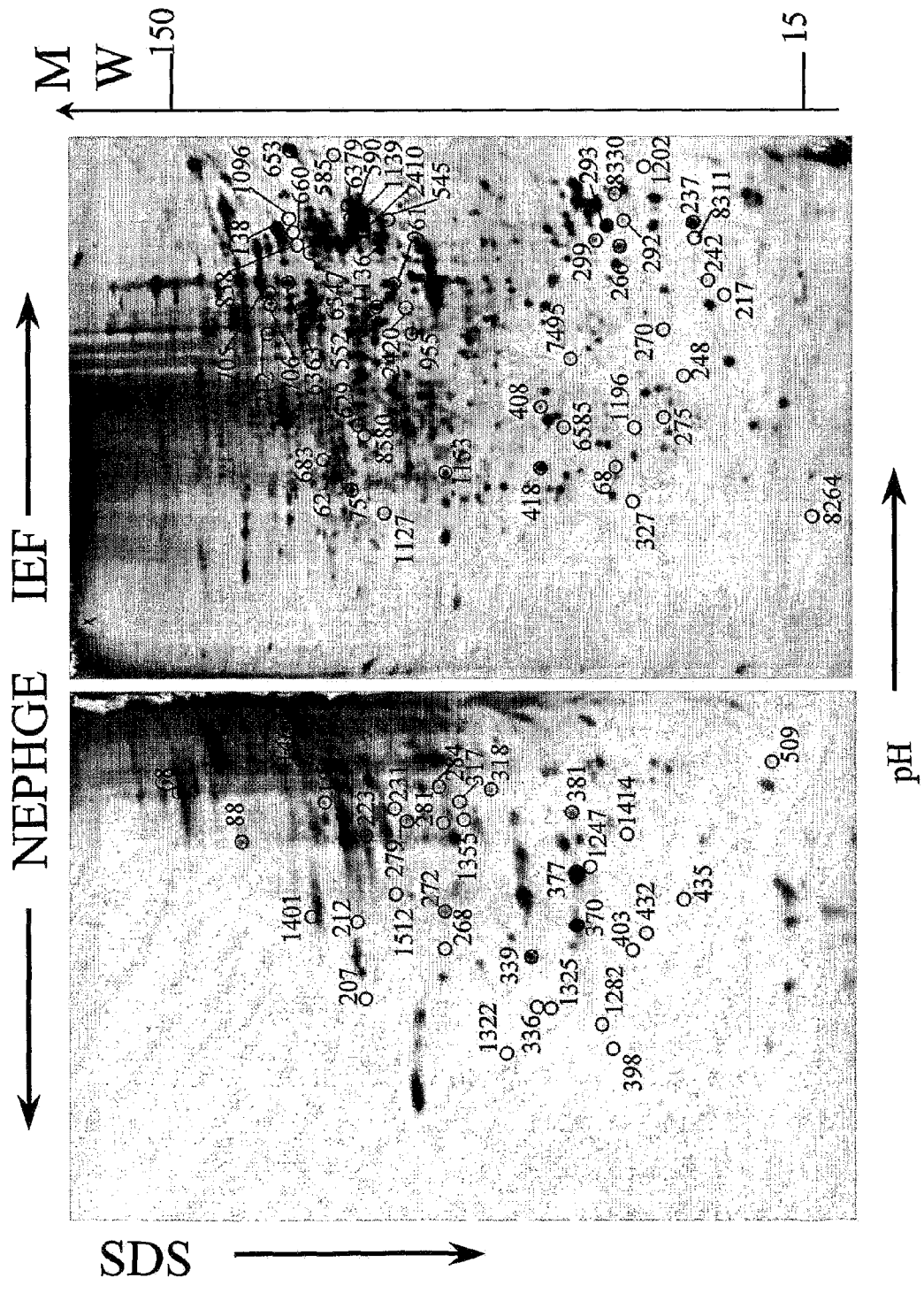
FIG. 1 is a fluorograph of two-dimensional gels of neonatal BB-DP rat islets of Langerhans. Marked proteins are those with altered levels of expression following incubation with IL-1β and the numbering corresponds to proteins listed in tables 1 and 2. A non-equilibrium pH-gradient electrophoresis (NEPHGE gel, pH 6.5-10.5) is represented on the left and an isoelectric focusing gel (IEF gel, pH 3.5-7) is represented on the right.
Figure 2:
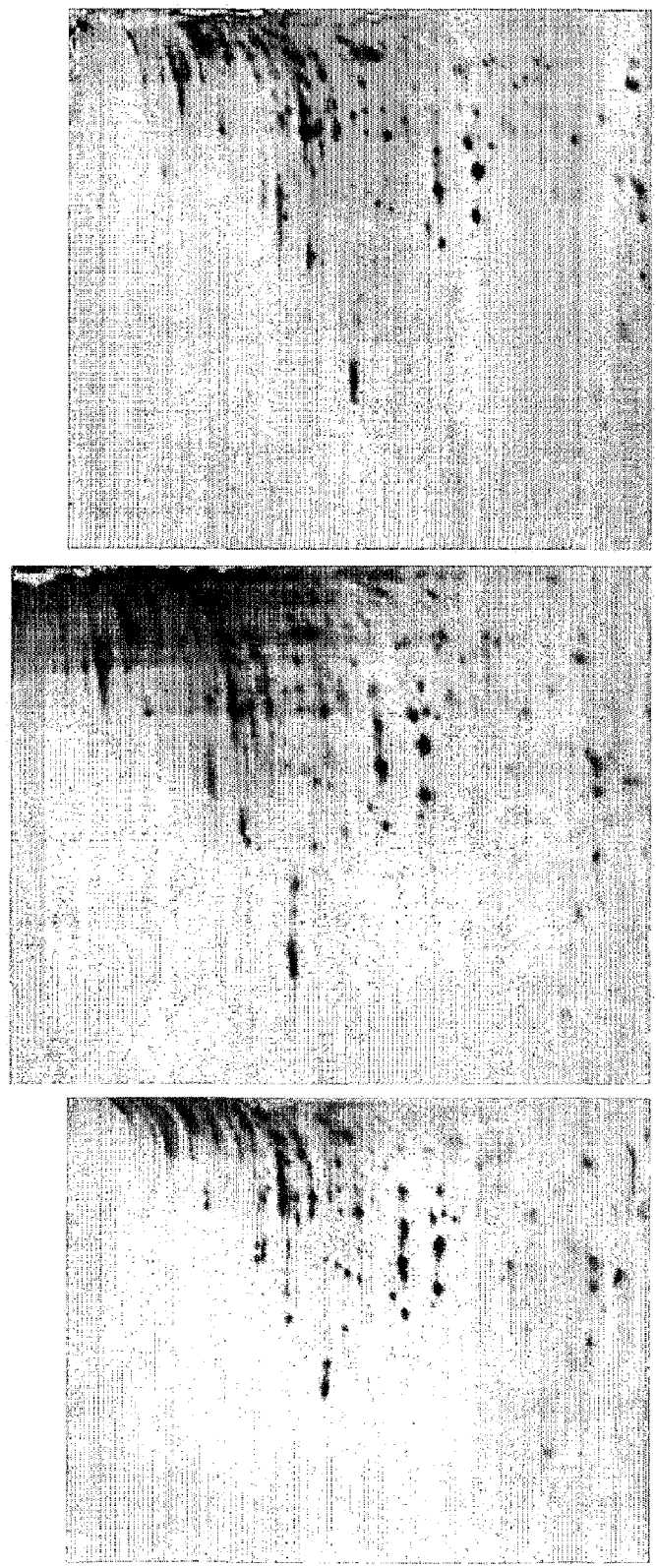
FIG. 2 is a fluorograph of two-dimensional gels of neonatal BB-DP rat islets of Langerhans prepared after 24-hour incubation in a control medium followed by [35S]-methionine labeling.
Figure 3A:
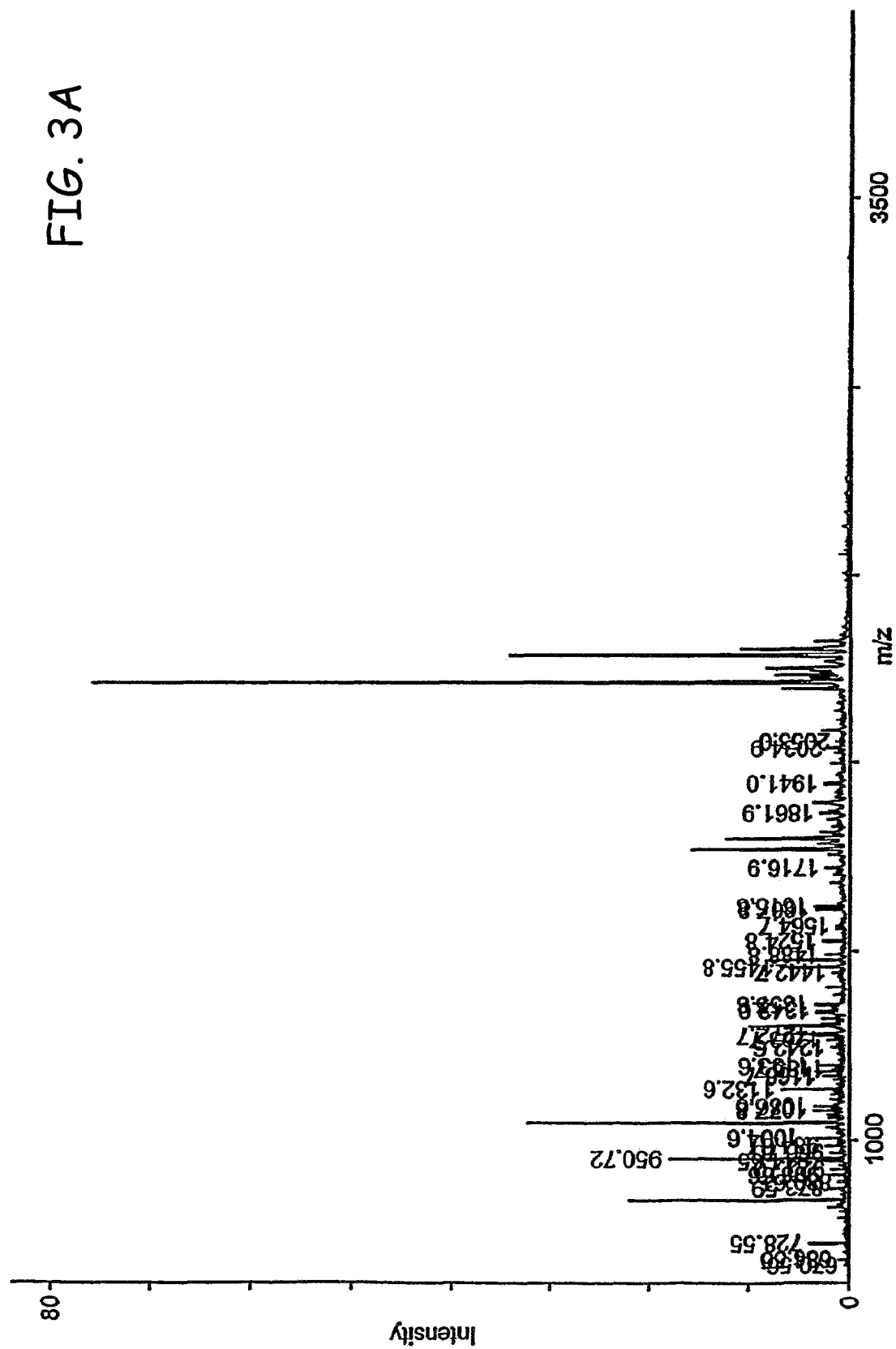
FIG. 3A is a total mass spectrometric graph with peak molecular weights noted in Daltons for IEF protein I 75 prepared from tryptic peptide fragments.
Figure 3B:
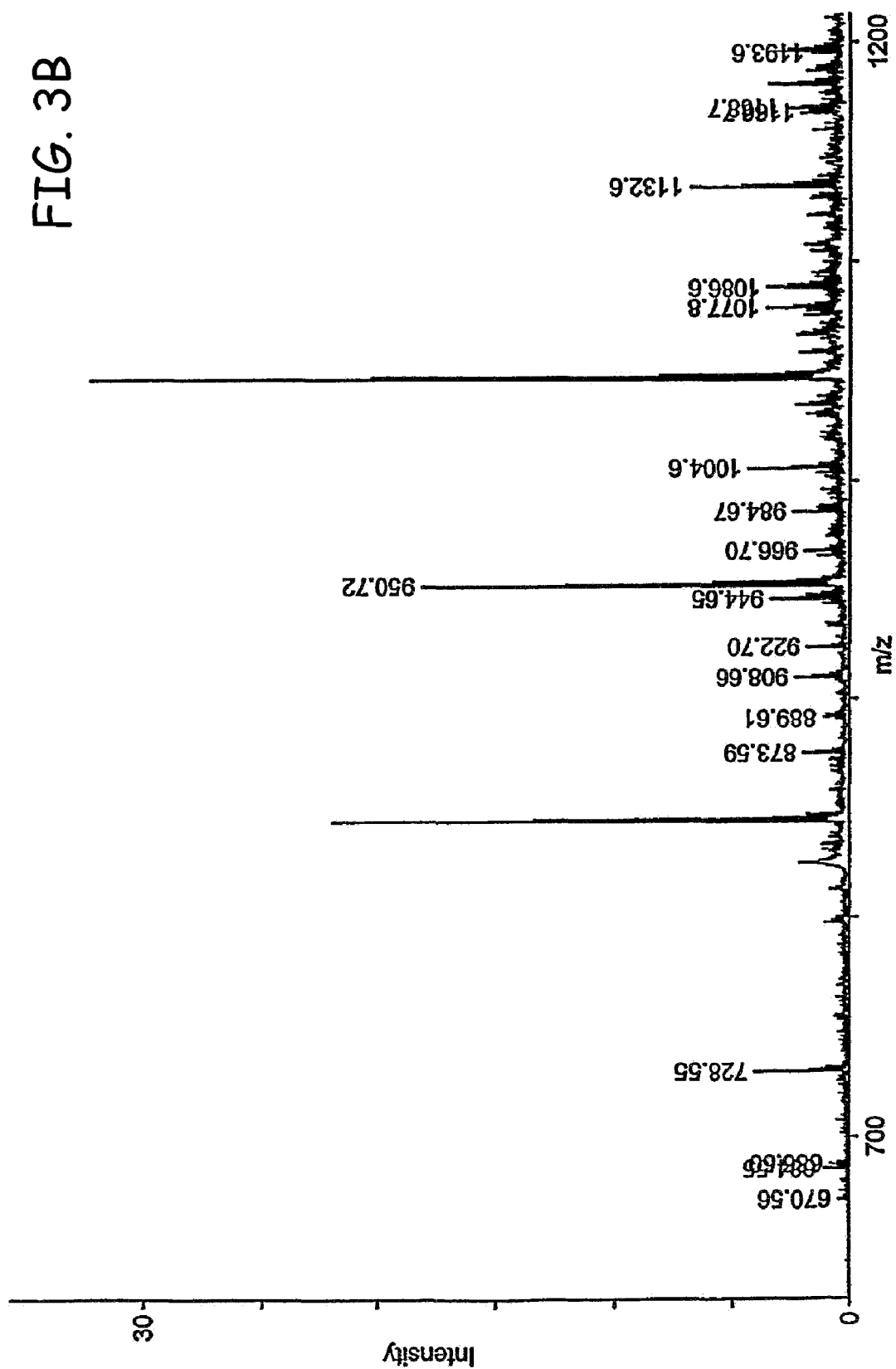
FIGS. 3B-3D represent enlarged regions of FIG. 3A for protein I 75 such that particular peaks may be readily identified.
Figure 3C:
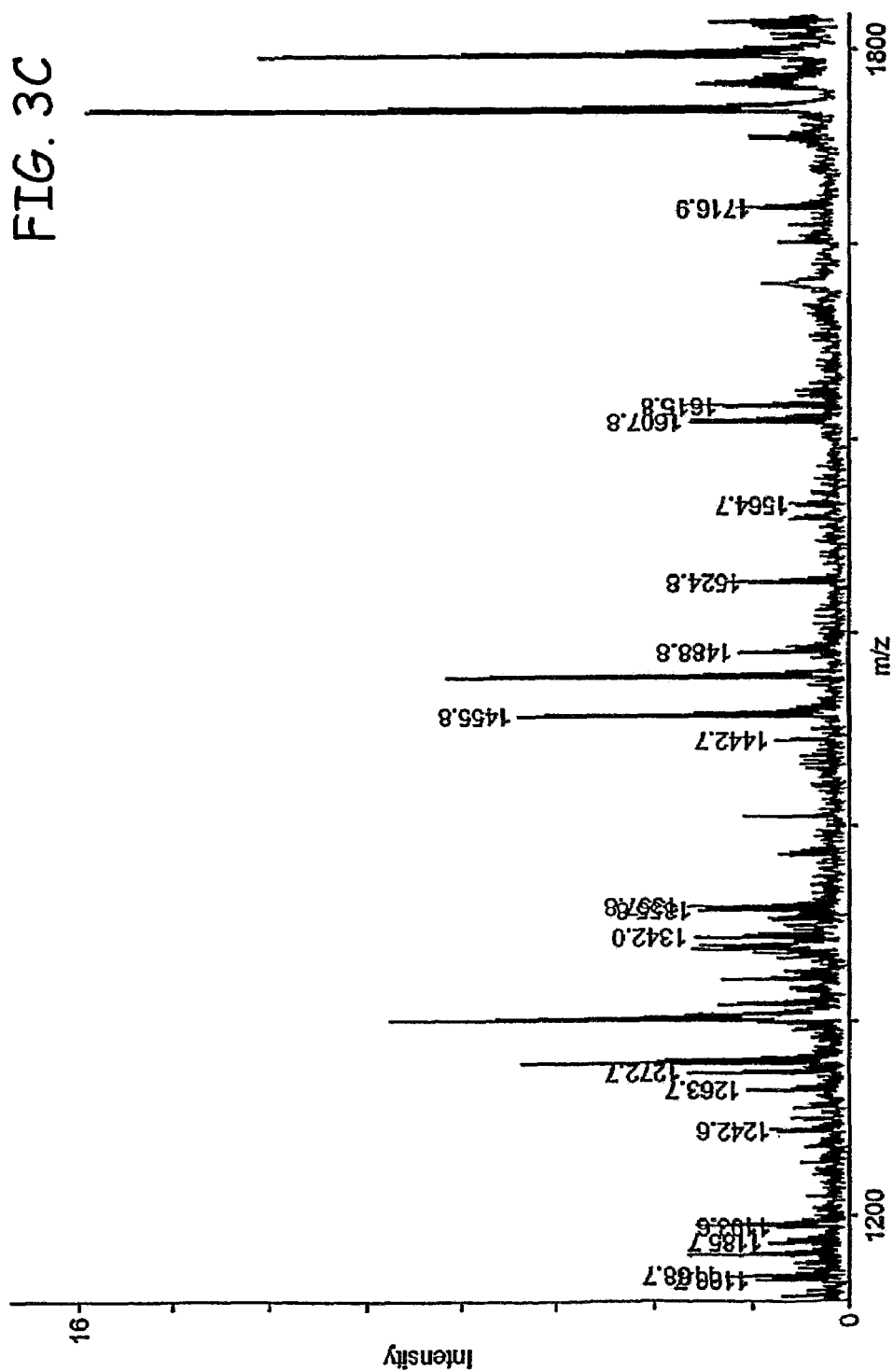
Figure 3D:
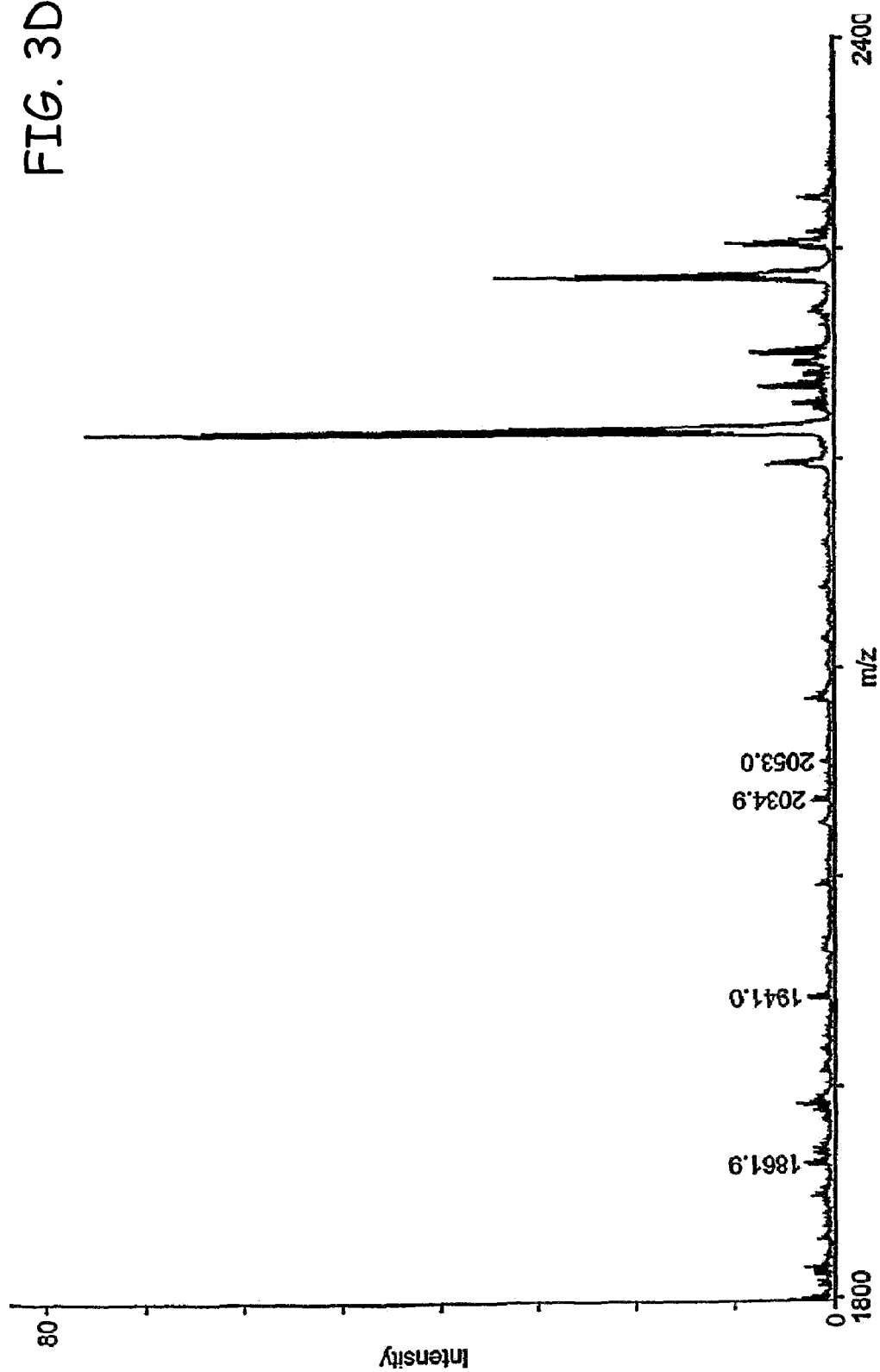
Figure 4A:
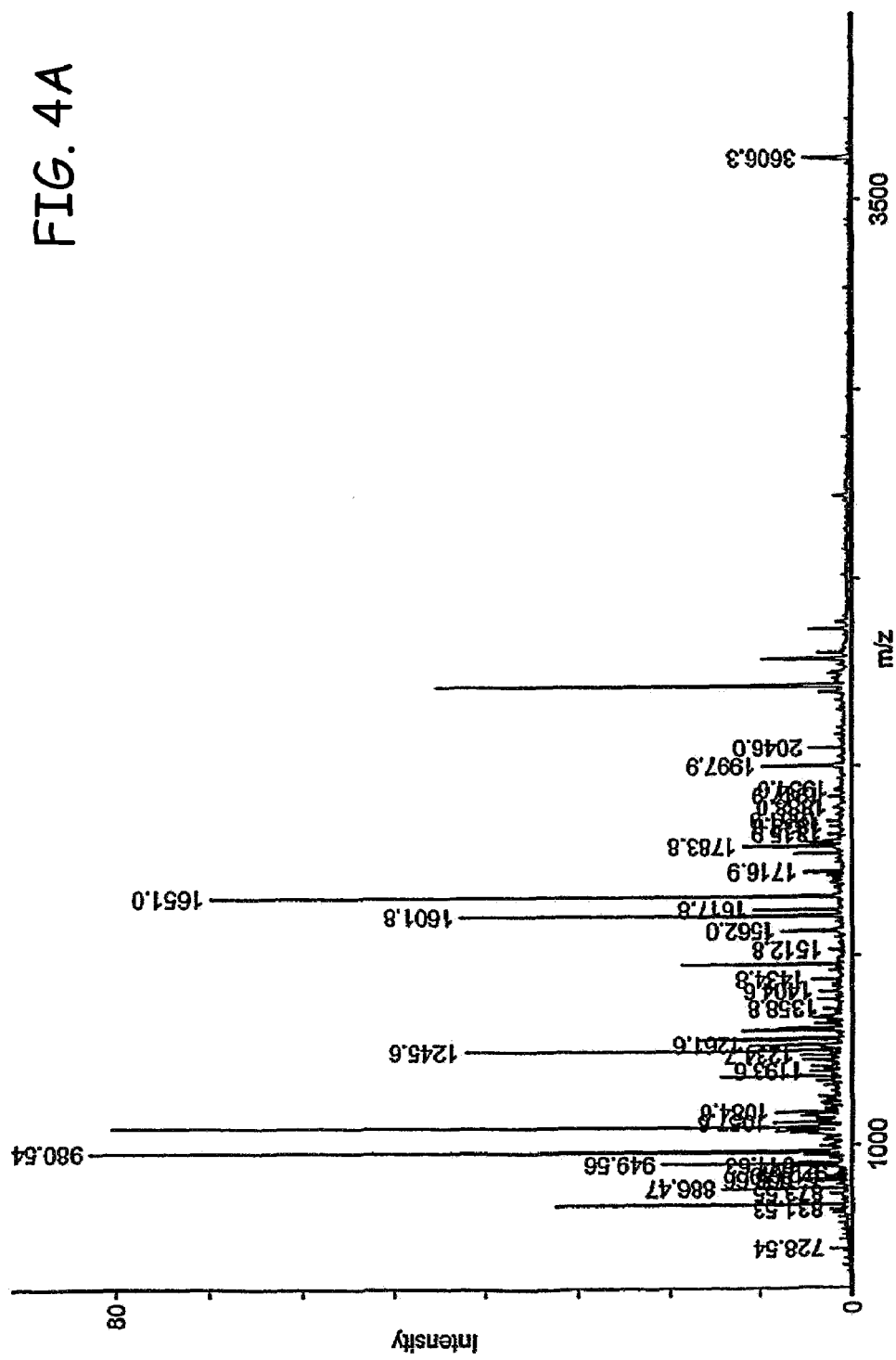
FIG. 4A is a total mass spectrometric graph with peak molecular weights noted in Daltons for IEF protein I 266 prepared from tryptic peptide fragments.
Figure 4D:
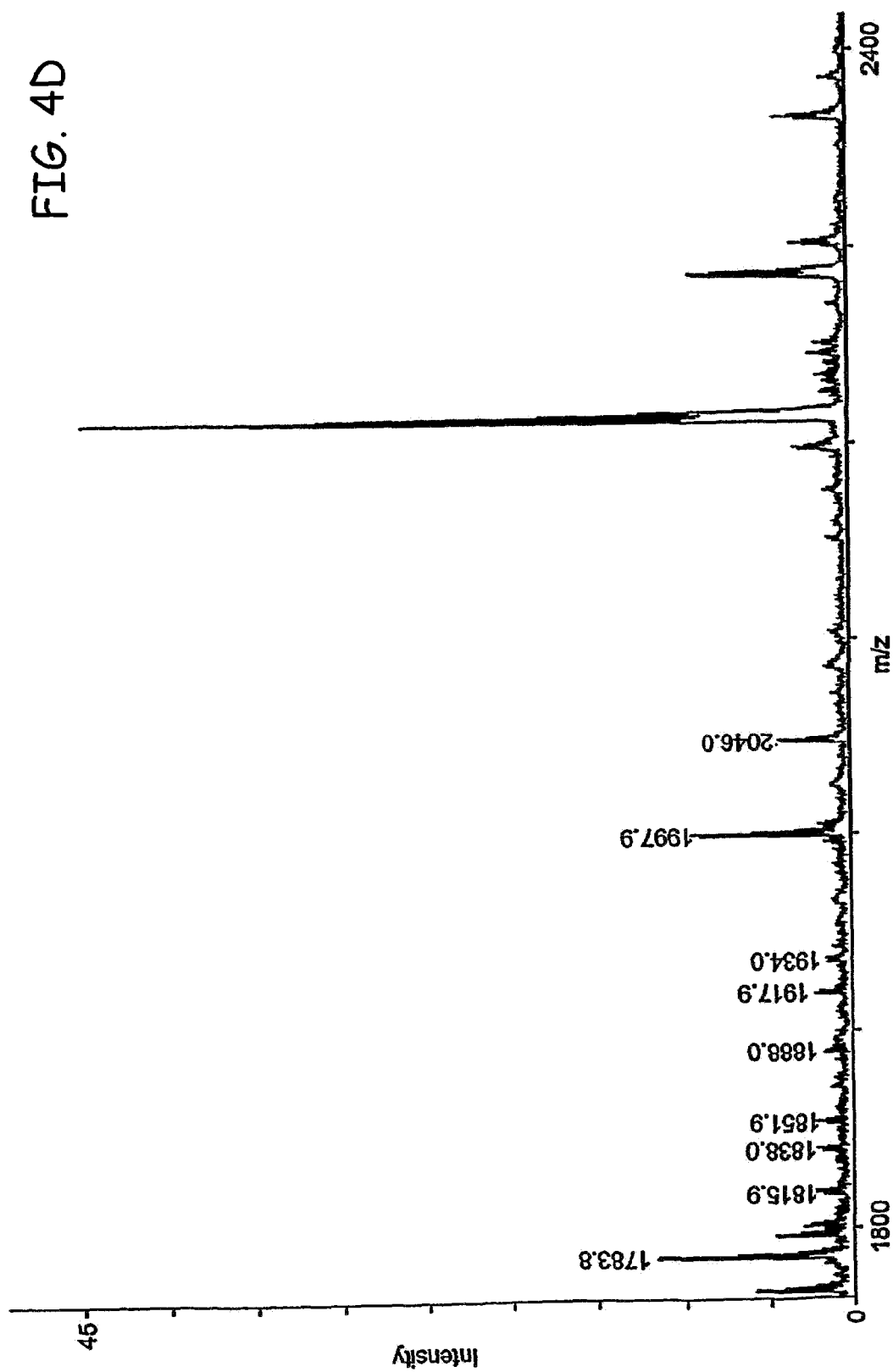
Figure 5A:
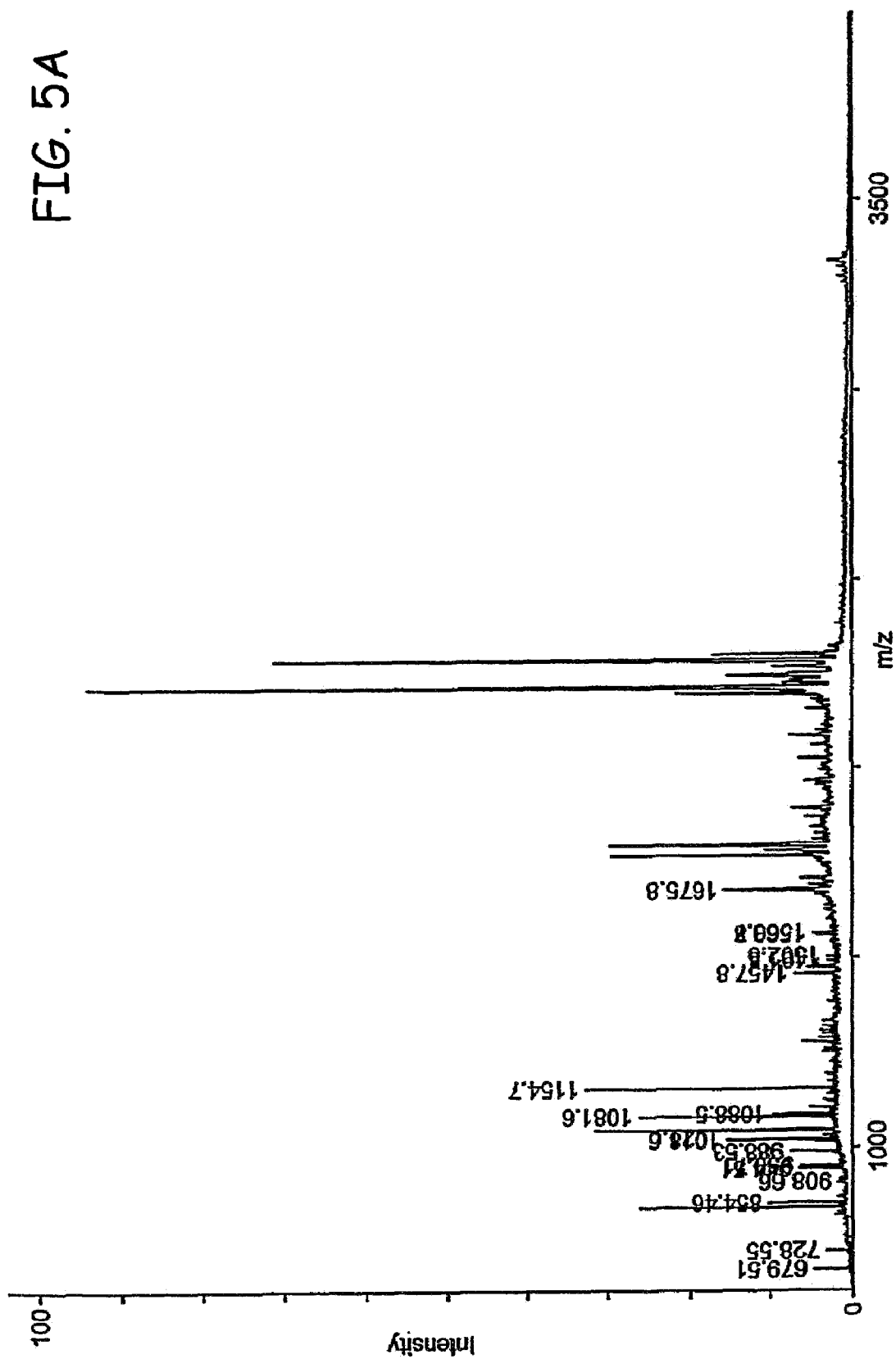
FIG. 5A is a total mass spectrometric graph with peak molecular weights noted in Daltons for IEF protein I 270 prepared from tryptic peptide fragments.
Figure 5B:
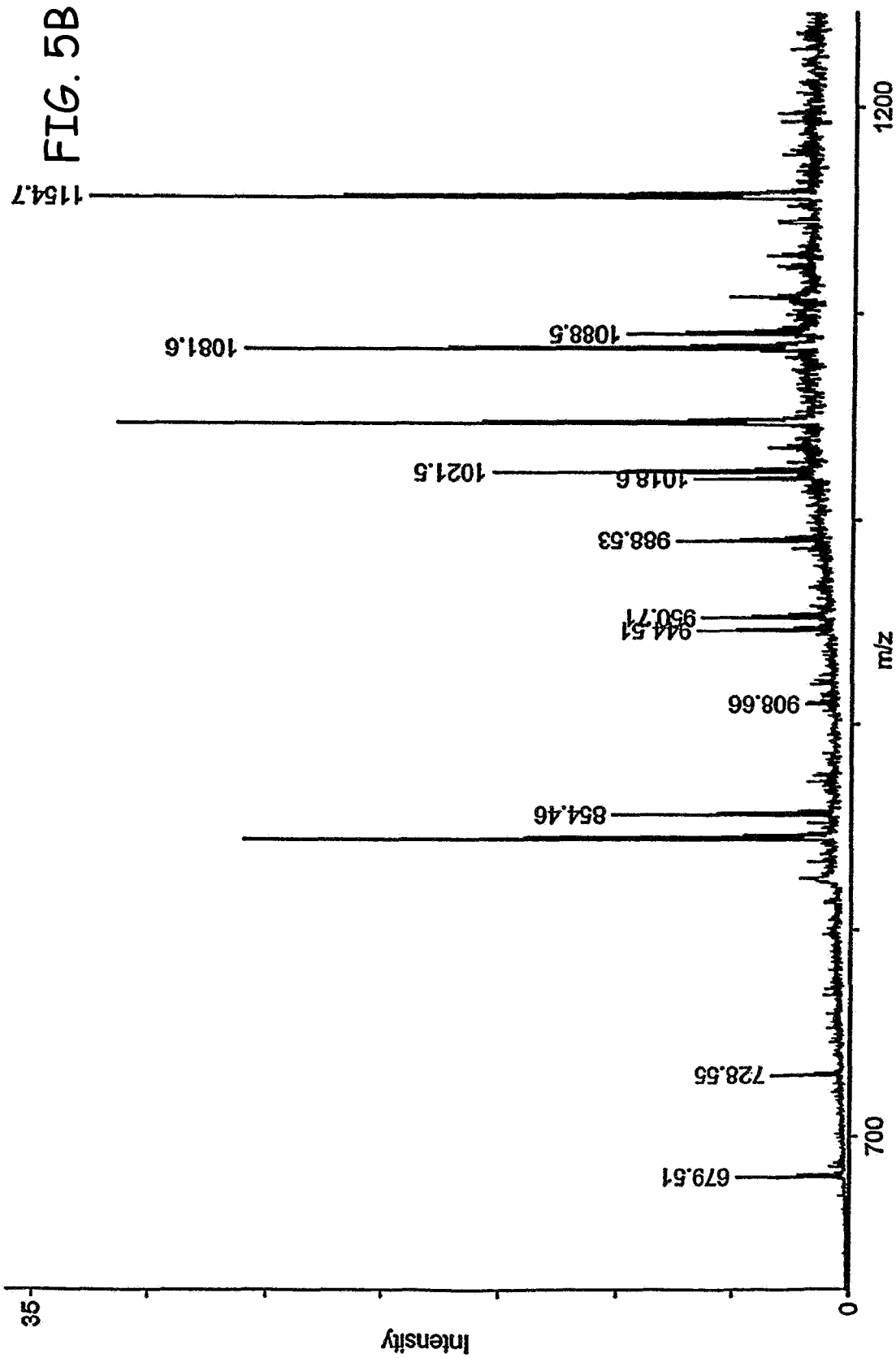
FIGS. 5B-5C represent enlarged regions of FIG. 5A for protein I 270 such that particular peaks may be readily identified.
Figure 5C:
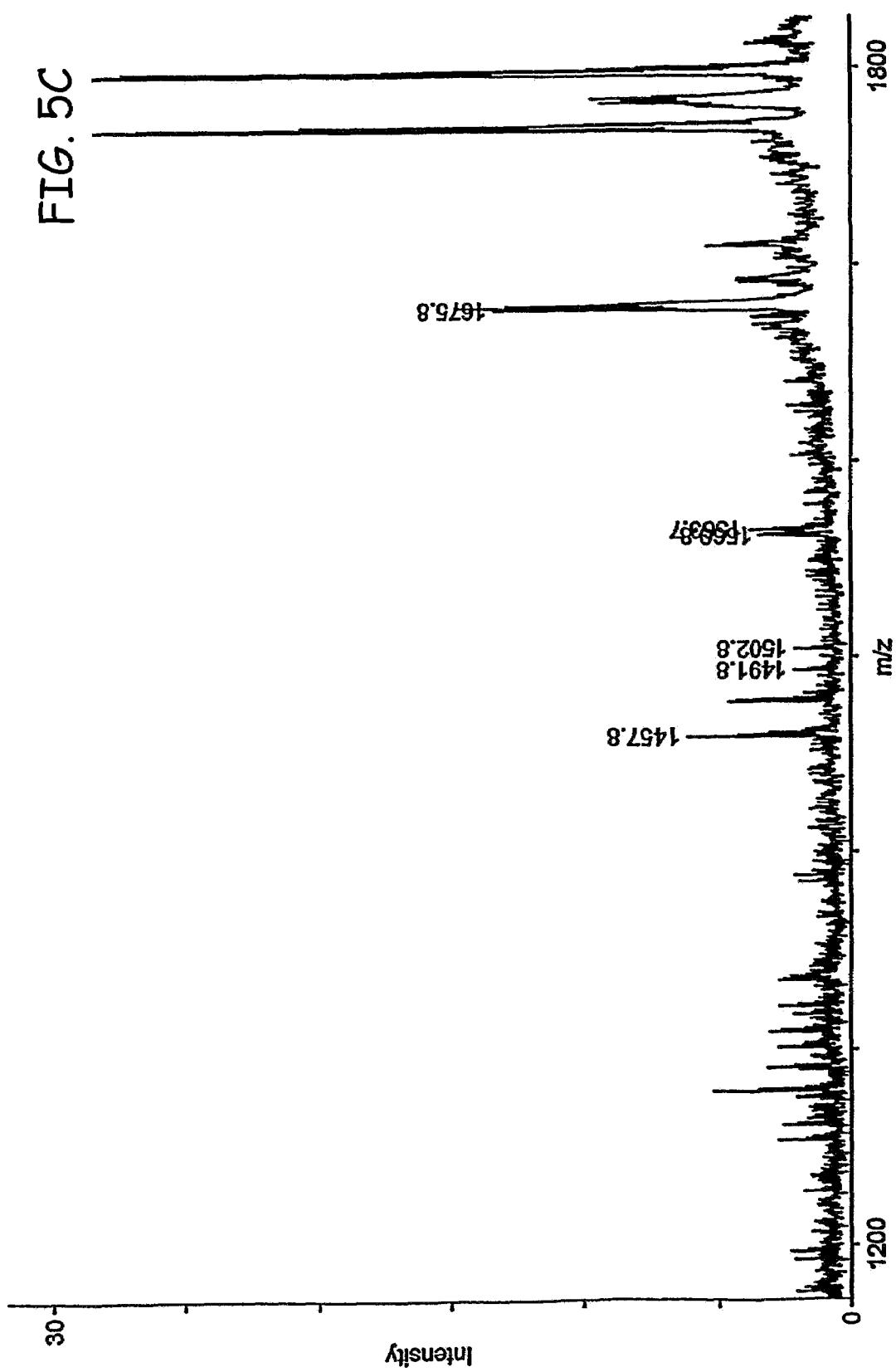
Figure 6A:
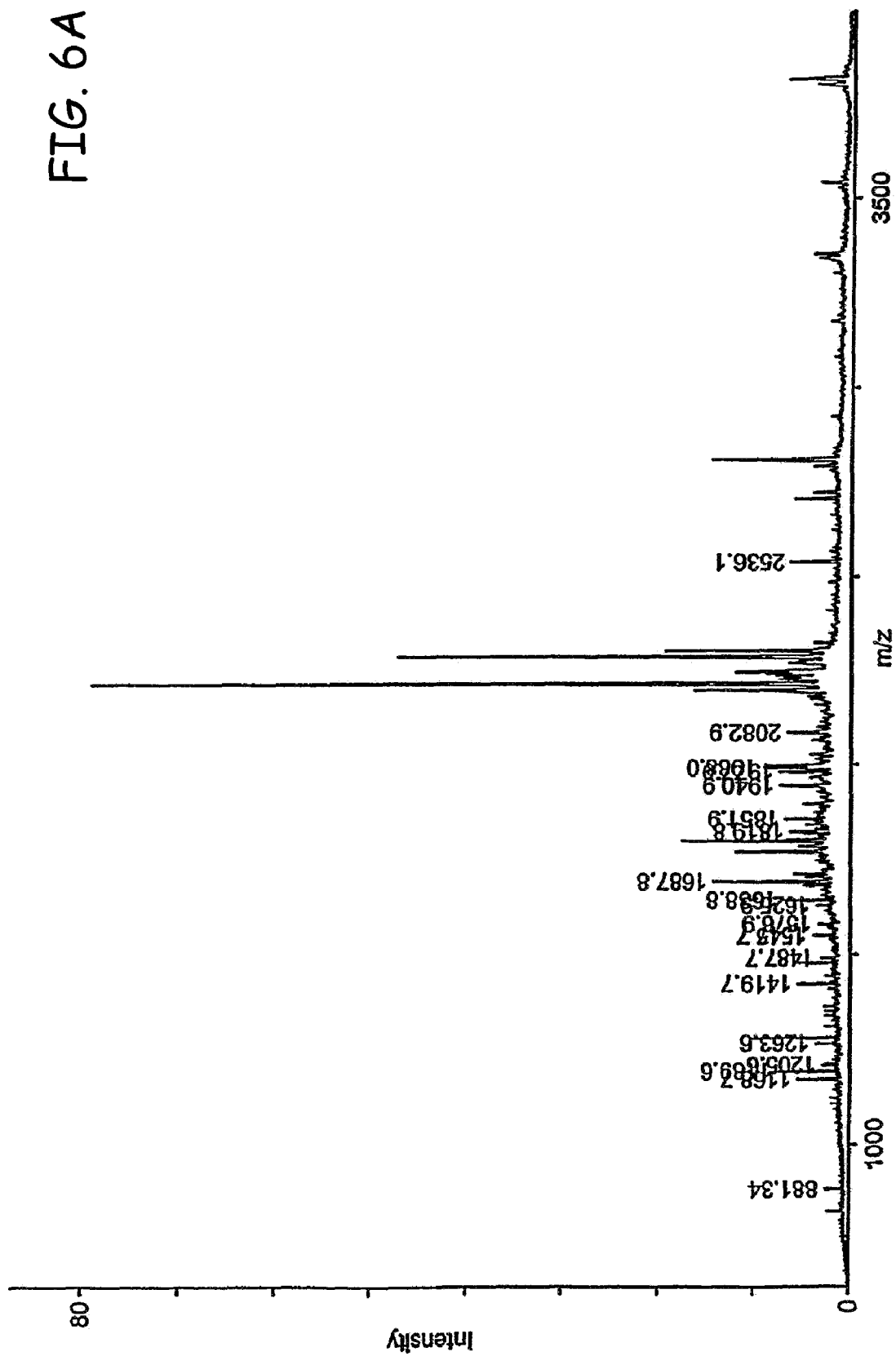
FIG. 6A is a total mass spectrometric graph with peak molecular weights noted in Daltons for IEF protein I 292 prepared from tryptic peptide fragments.
Figure 6B:
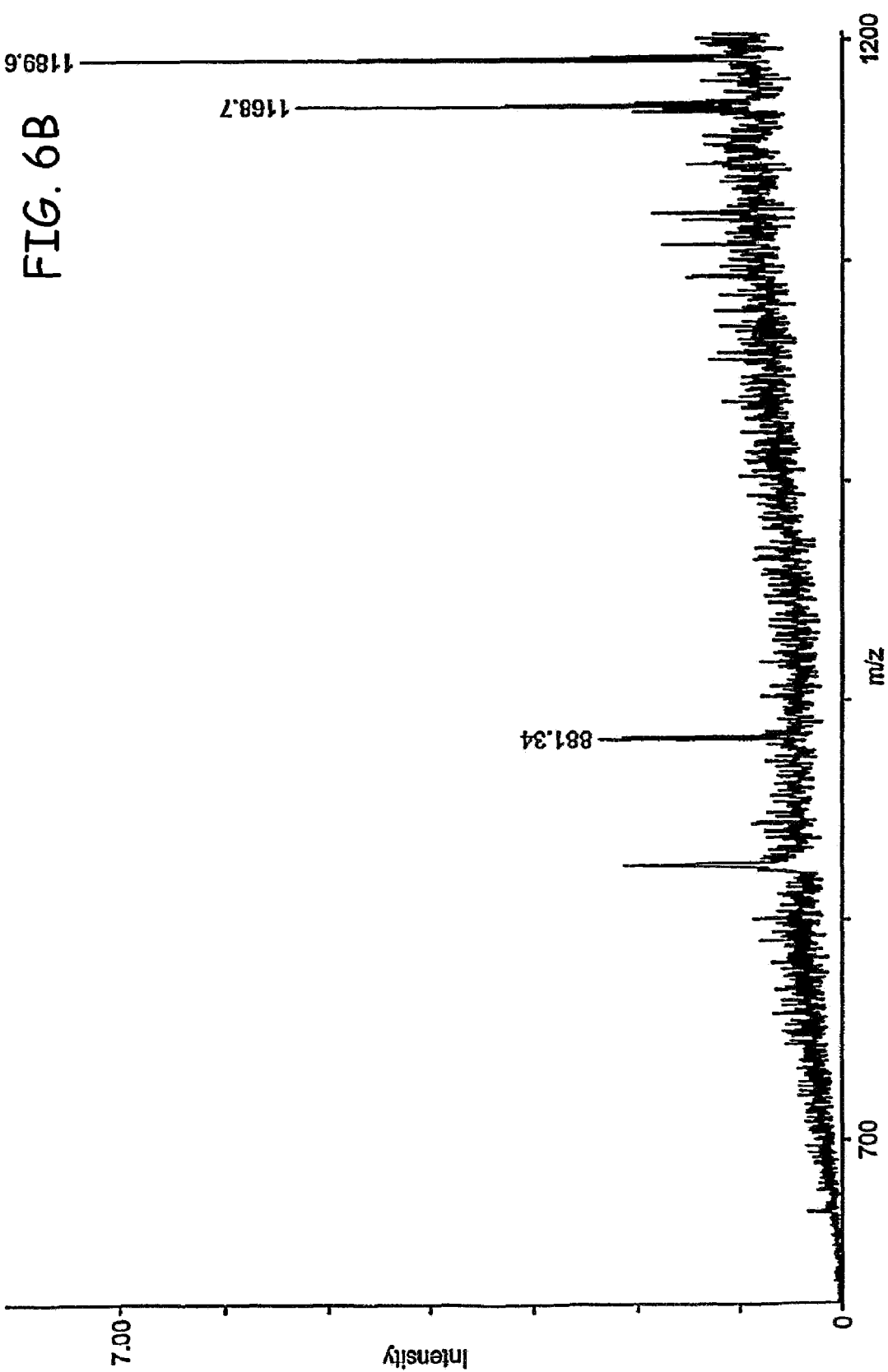
FIGS. 6B-6E represent enlarged regions of FIG. 6A for protein I 292 such that particular peaks may be readily identified.
Figure 6C:
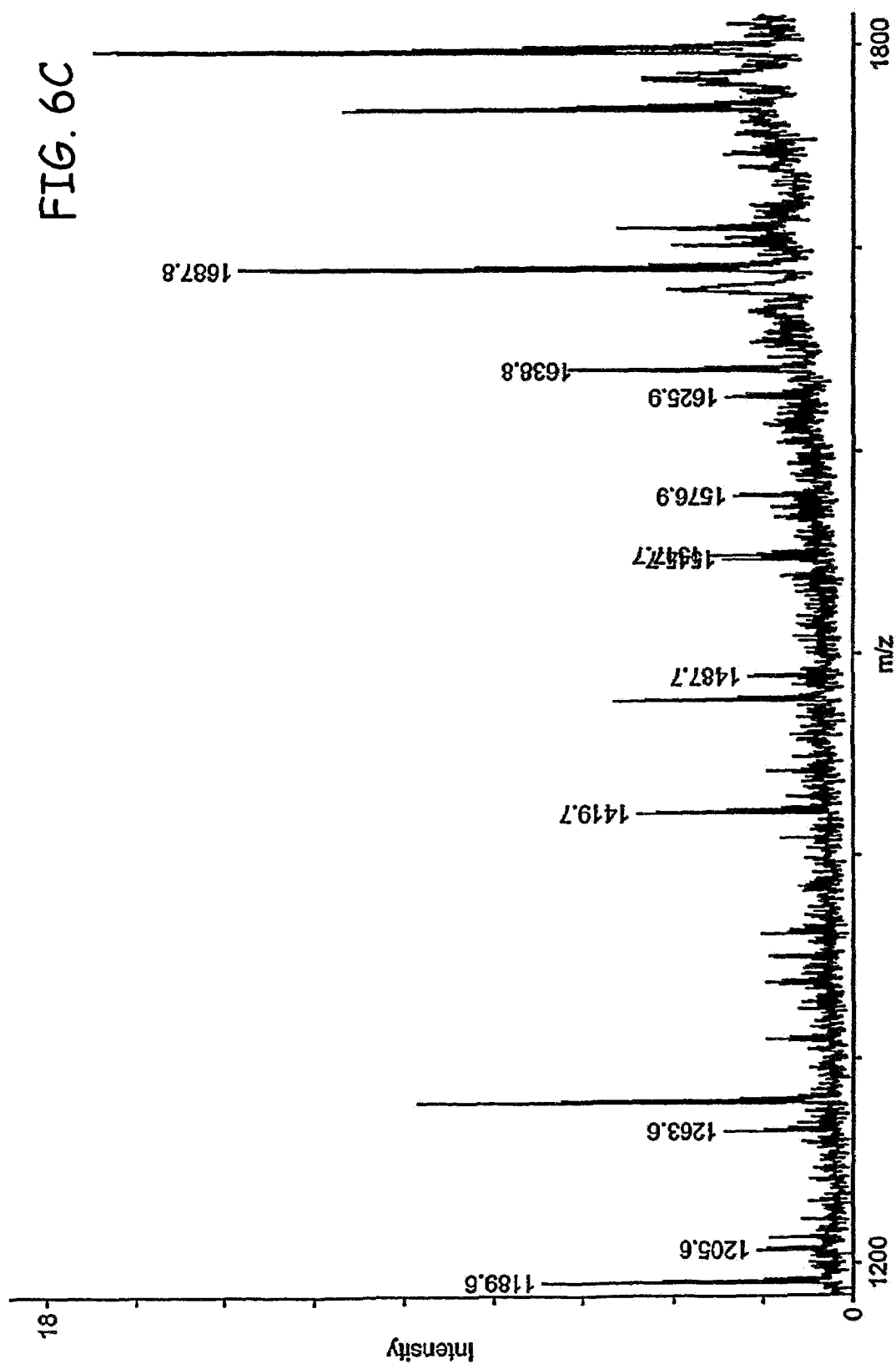
Figure 6D:
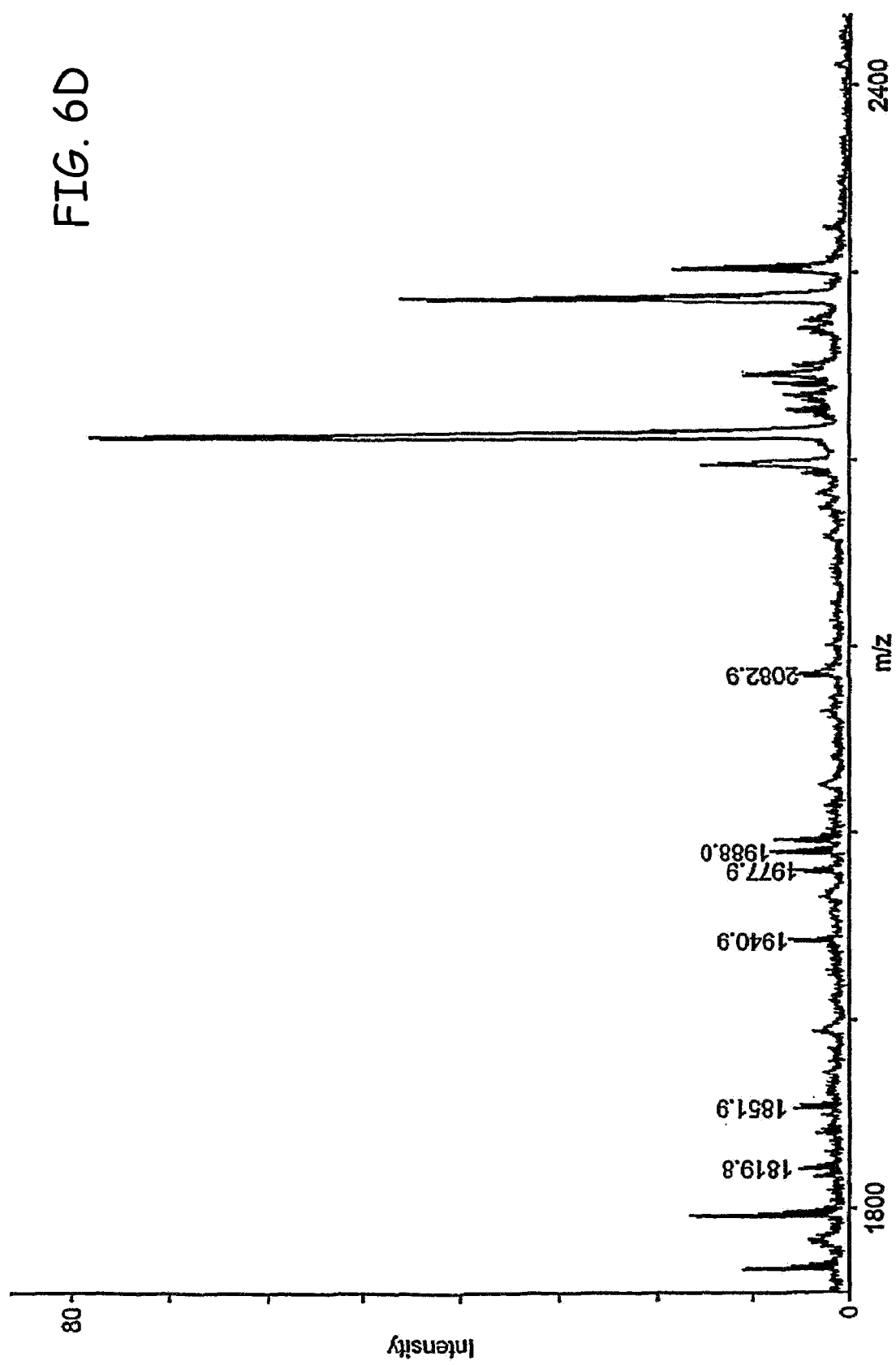
Figure 6E:
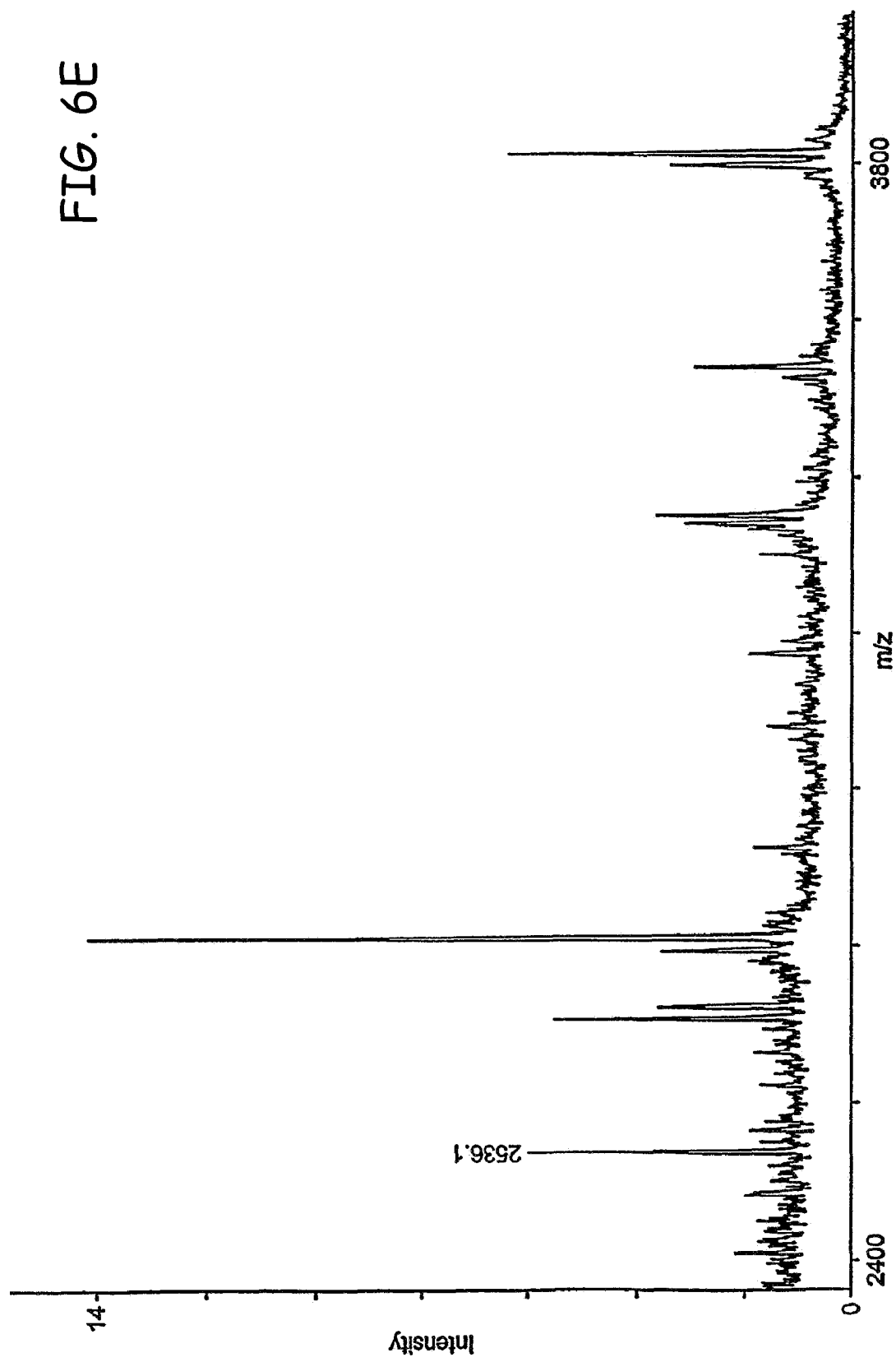
Figure 7A:
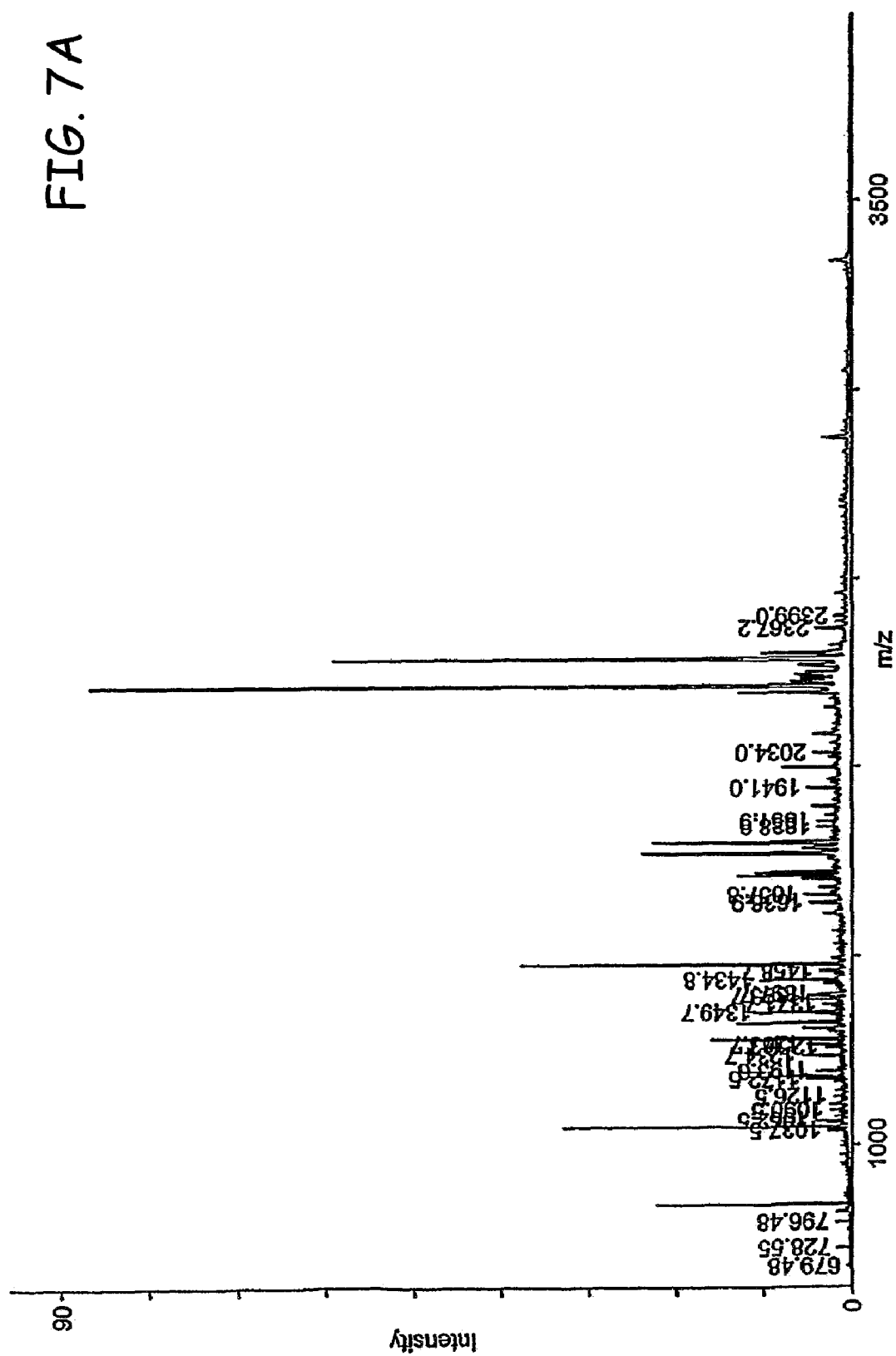
FIG. 7A is a total mass spectrometric graph with peak molecular weights noted in Daltons for LEE protein I 408 prepared from tryptic peptide fragments.
Figure 7B:
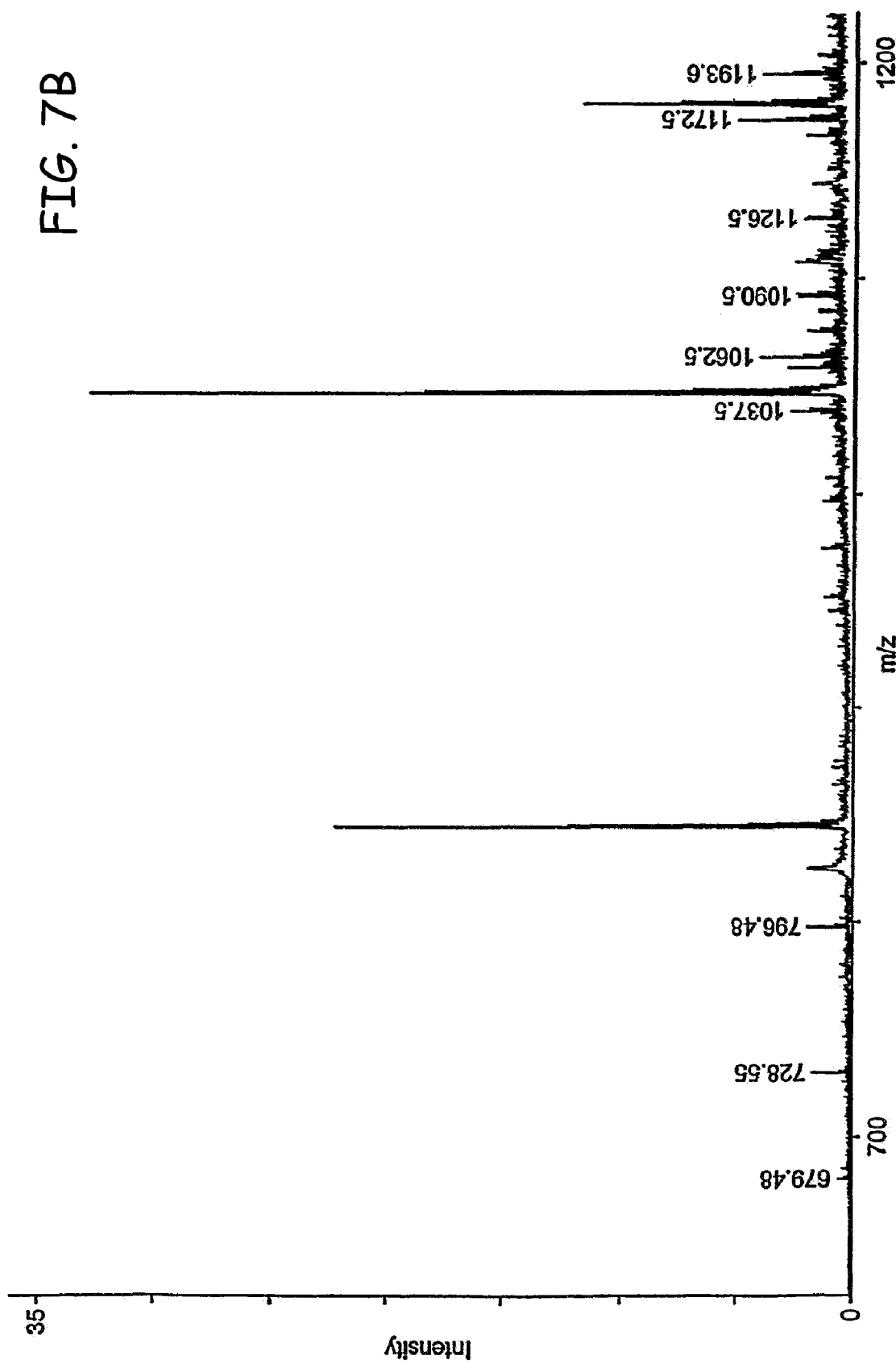
FIGS. 7B-7D represent enlarged regions of FIG. 7A for protein I 408 such that particular peaks may be readily identified.
Figure 7C:
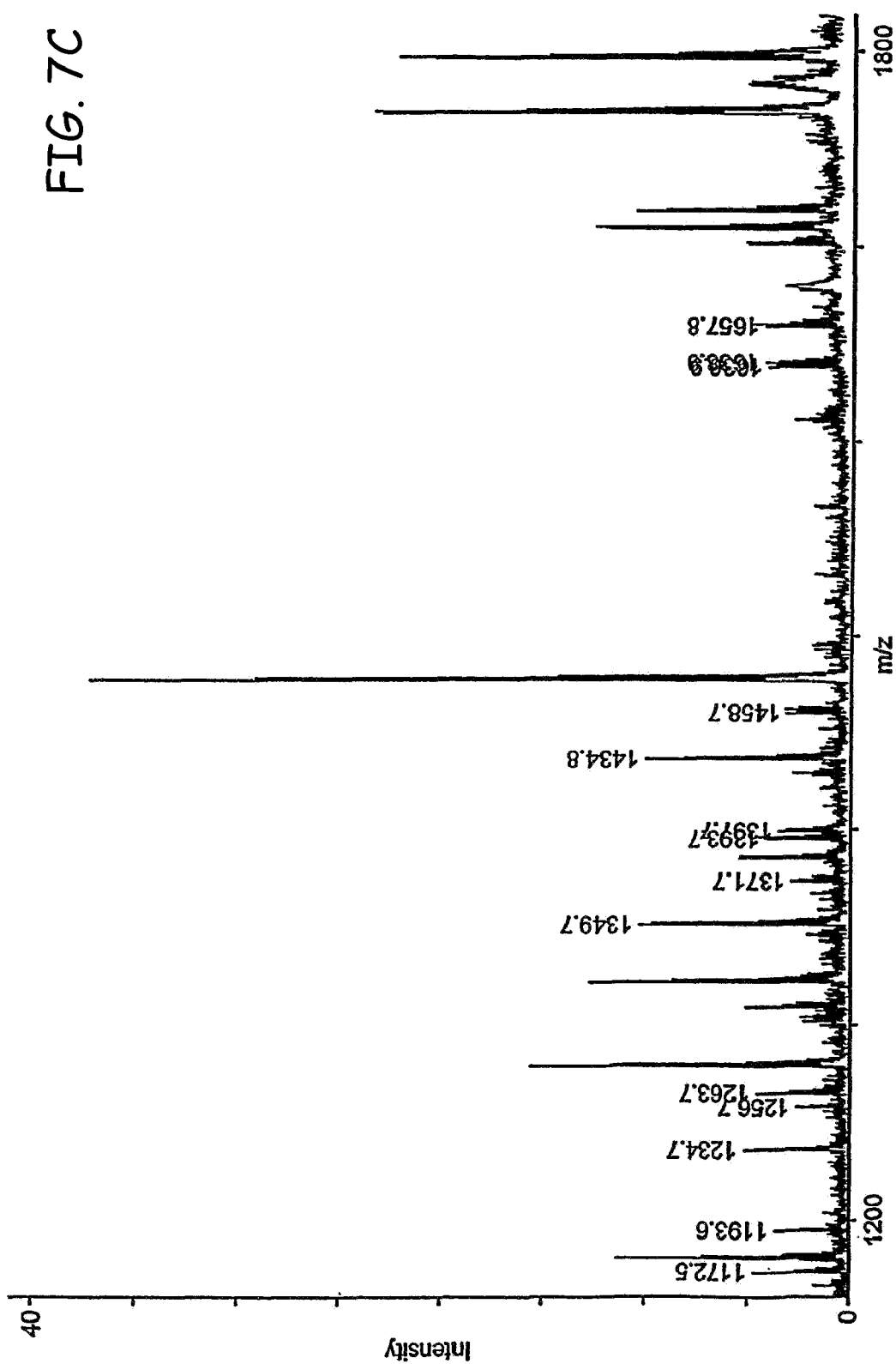
Figure 7D:
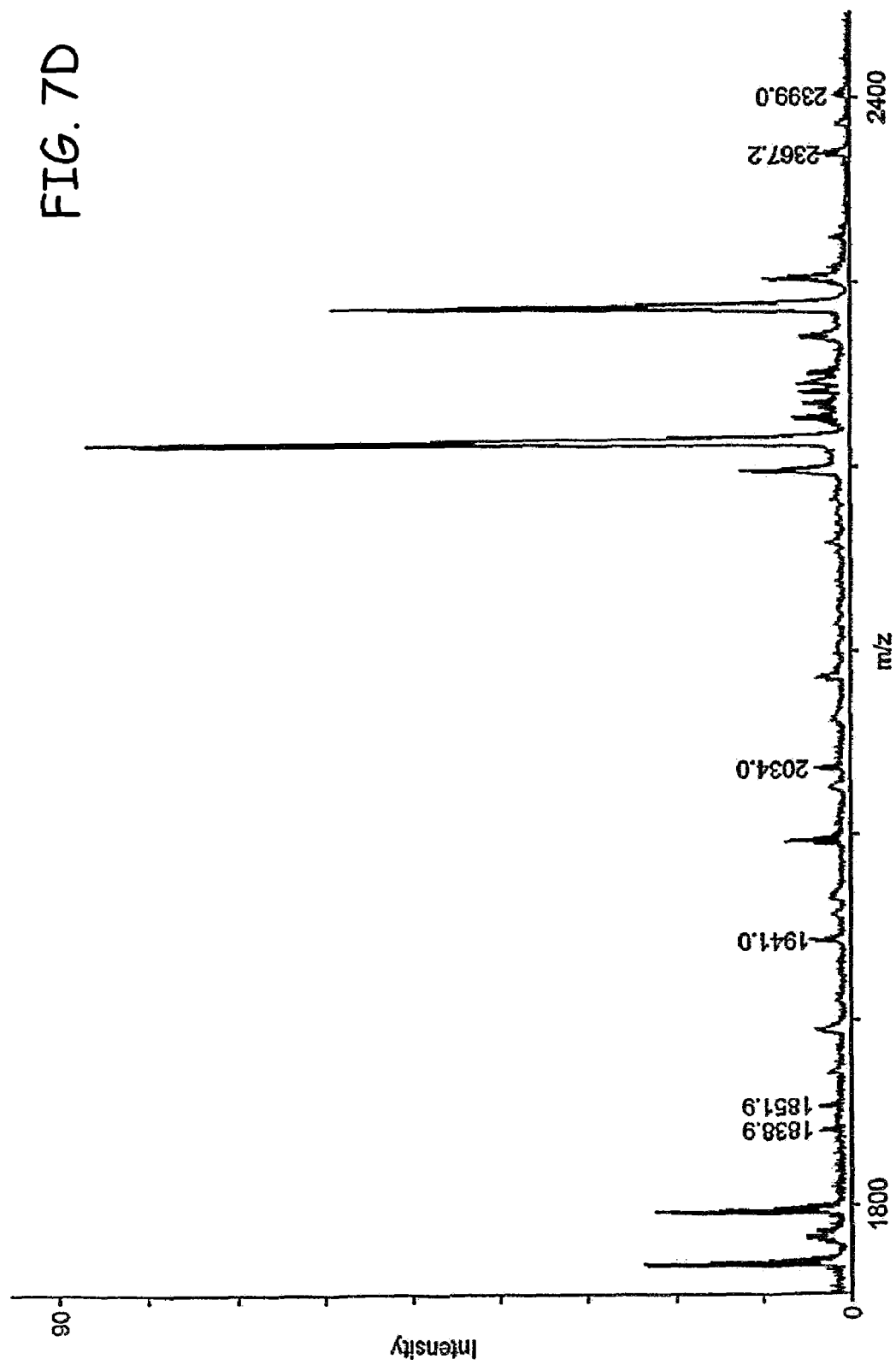
Figure 8A:
FIG. 8A is a total mass spectrometric graph with peak molecular weights noted in Daltons for IEF protein I 418 prepared from tryptic peptide fragments.
Figure 8B:
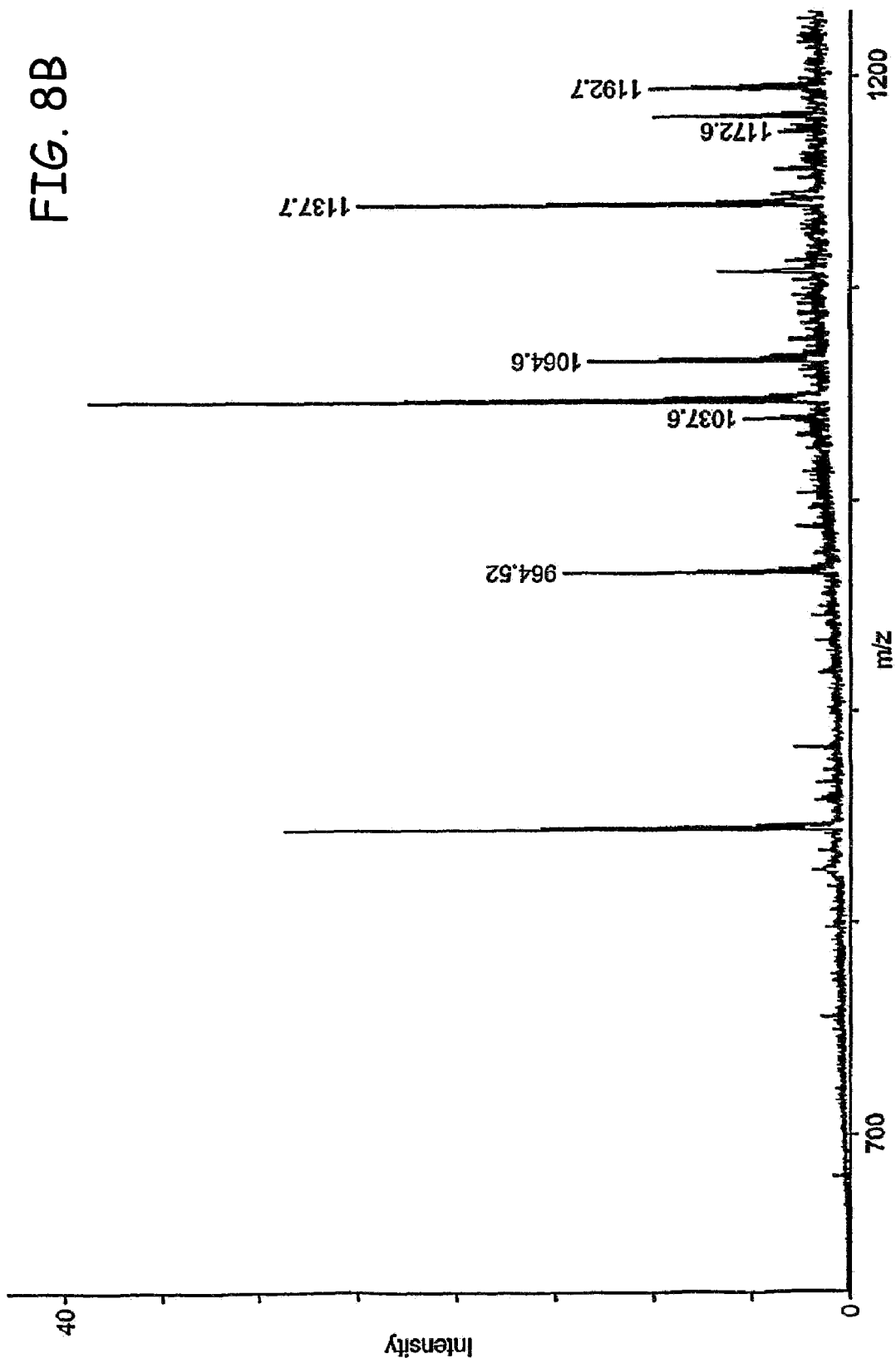
FIGS. 8B-8E represent enlarged regions of FIG. 8A for protein I 418 such that particular peaks may be readily identified.
Figure 8C:
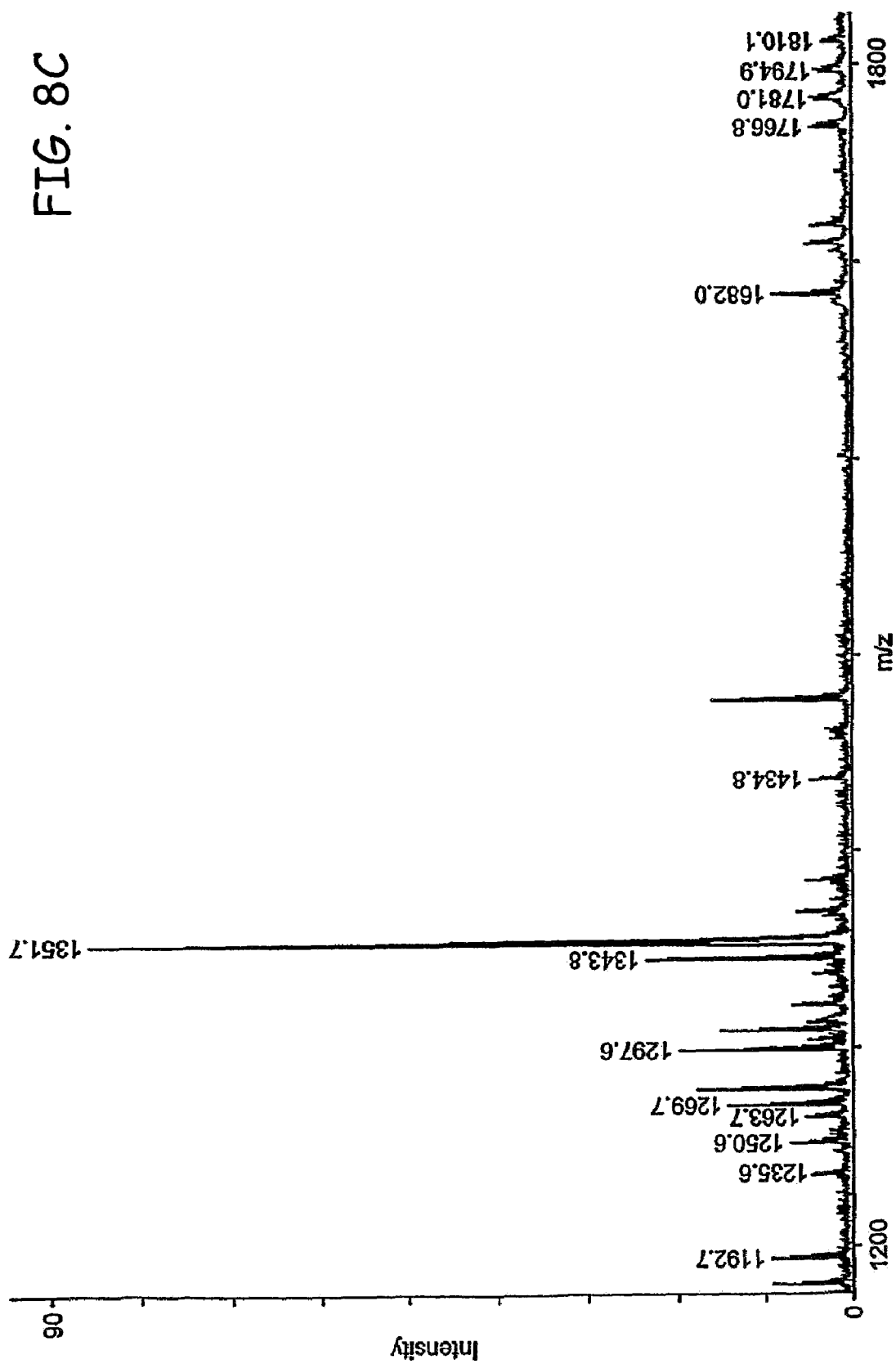
Figure 8D:
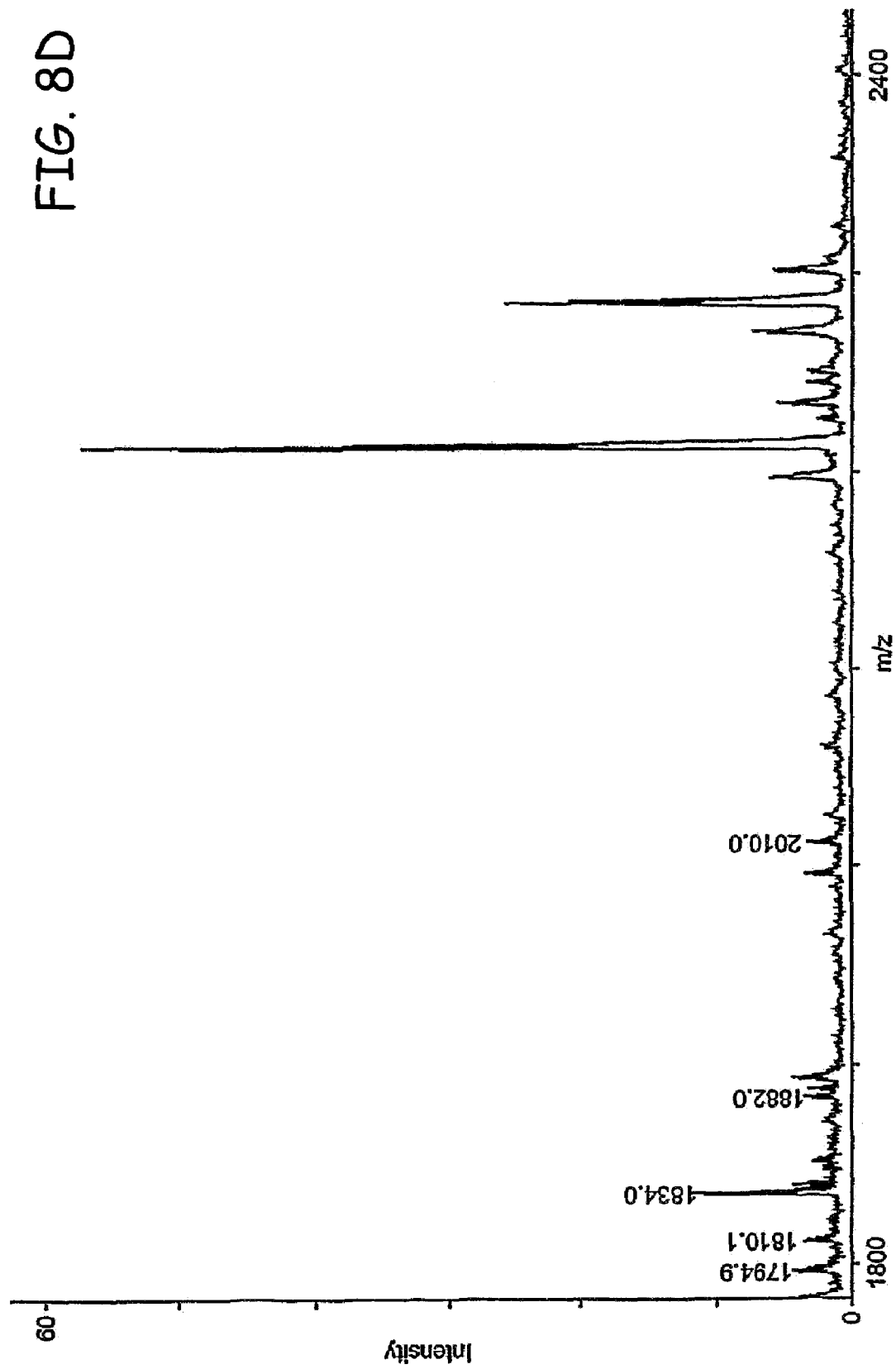
Figure 8E:
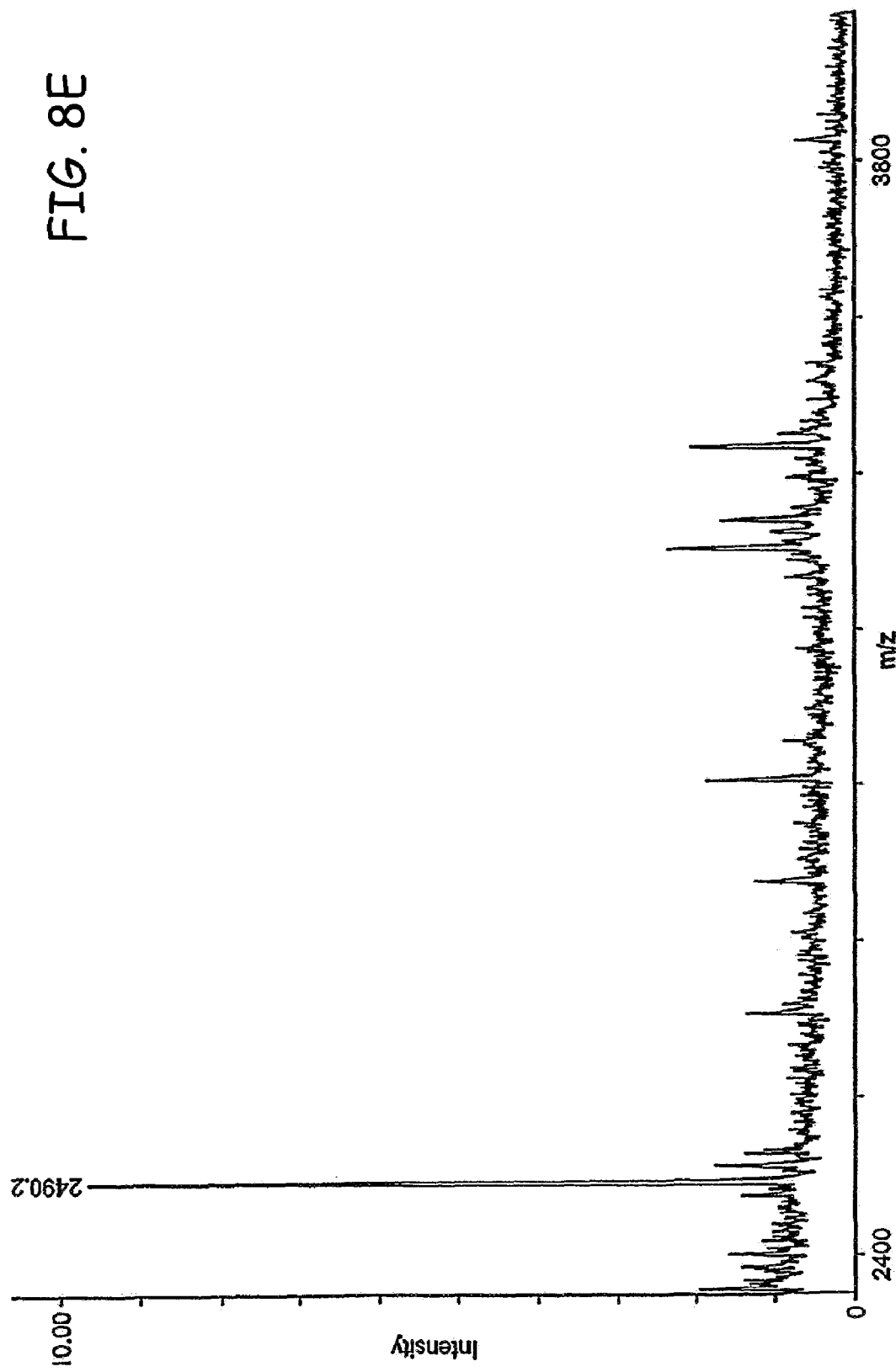
Figure 9A:
FIG. 9A is a total mass spectrometric graph with peak molecular weights noted in Daltons for IEF protein I 683 prepared from tryptic peptide fragments.
Figure 9B:
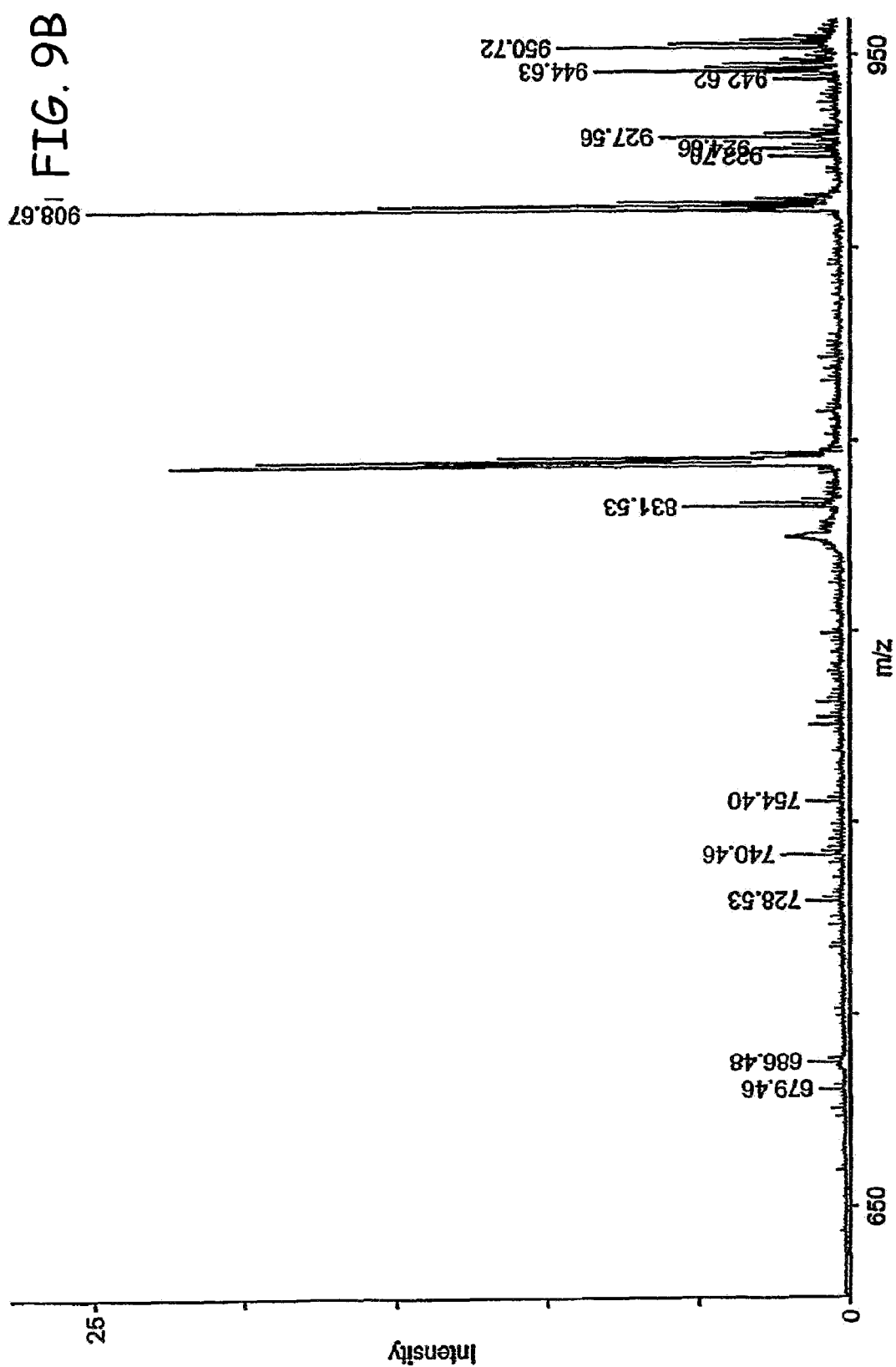
Figure 9C:
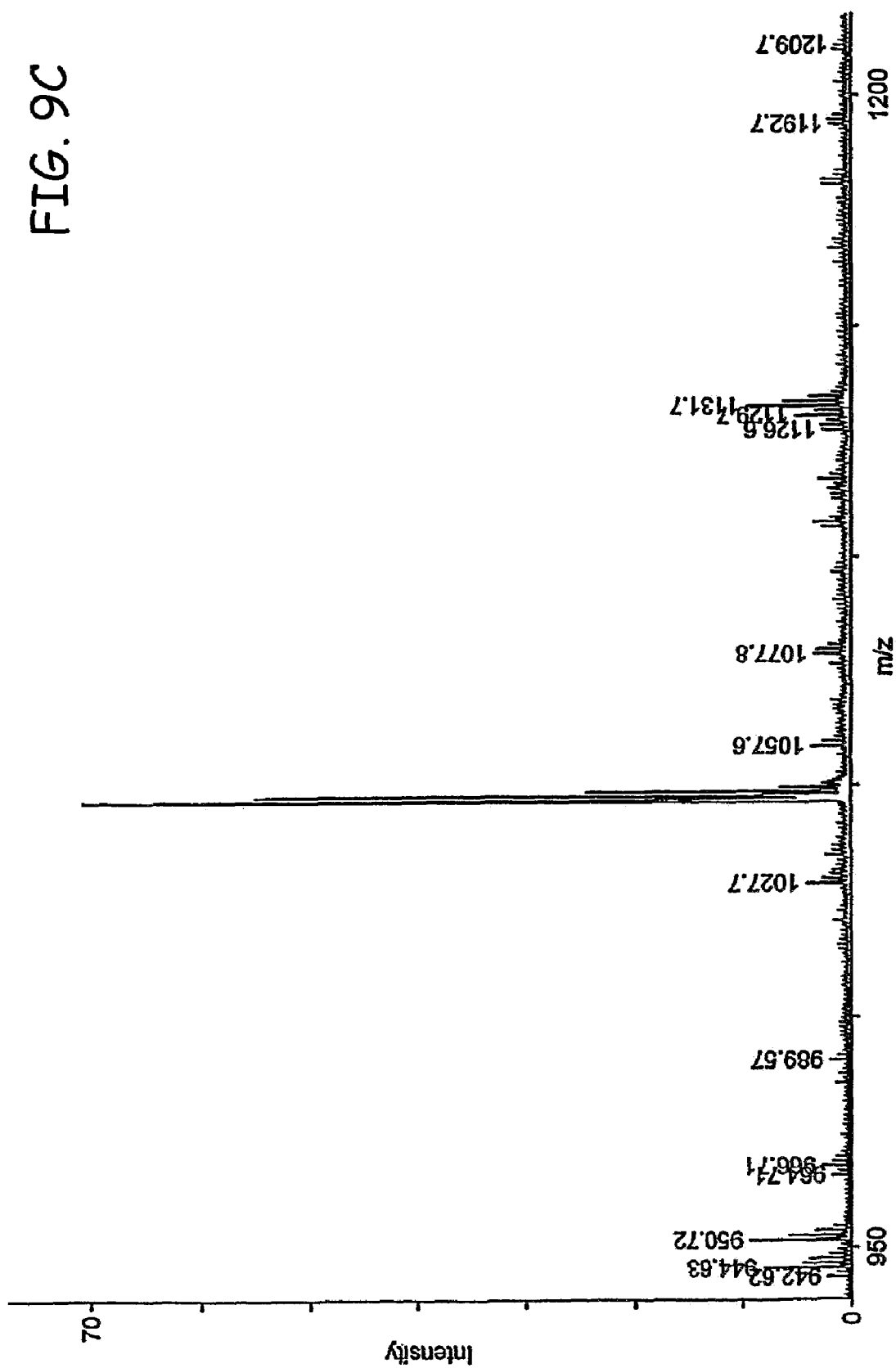
Figure 9E:
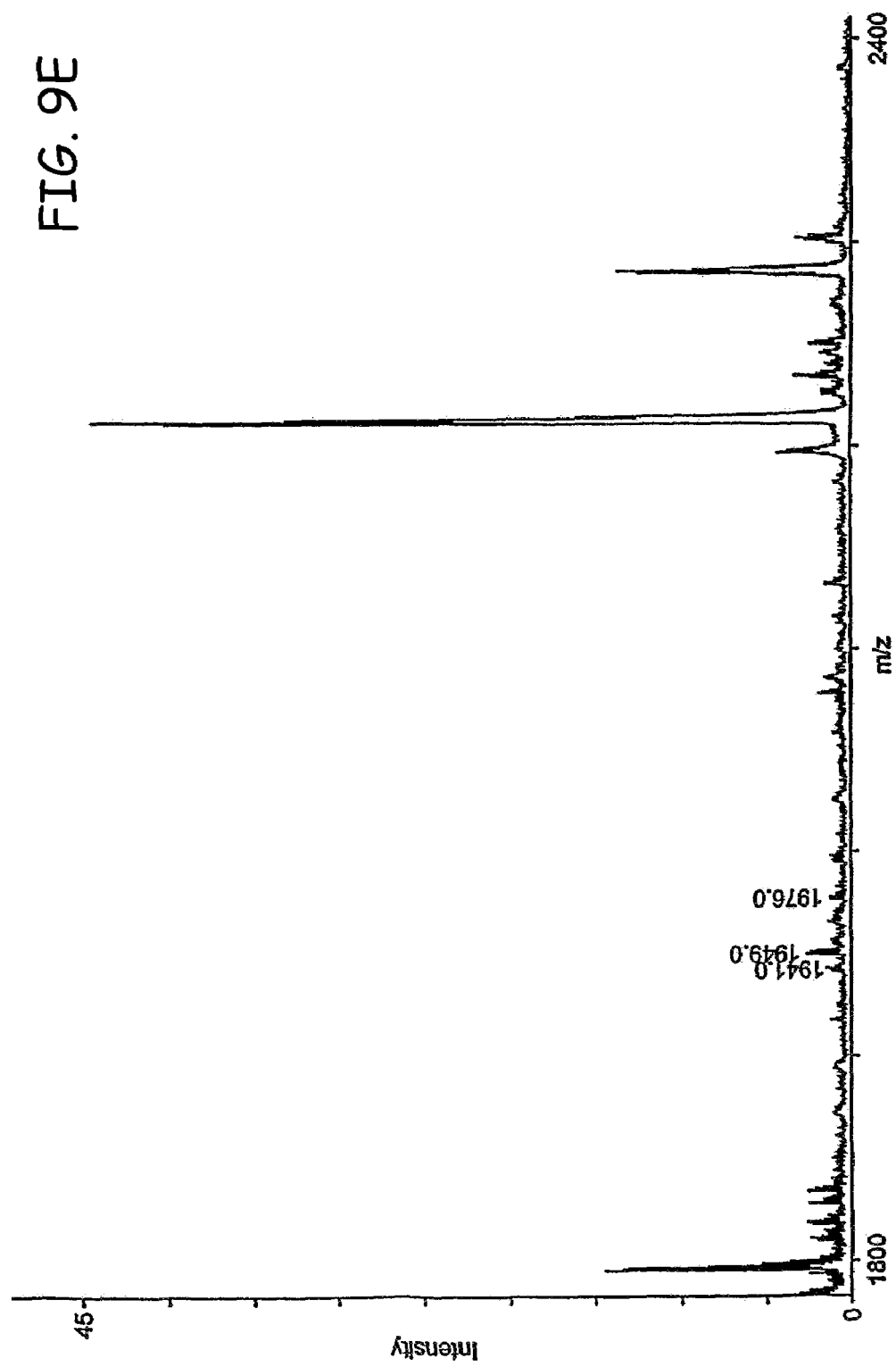
Figure 10A:
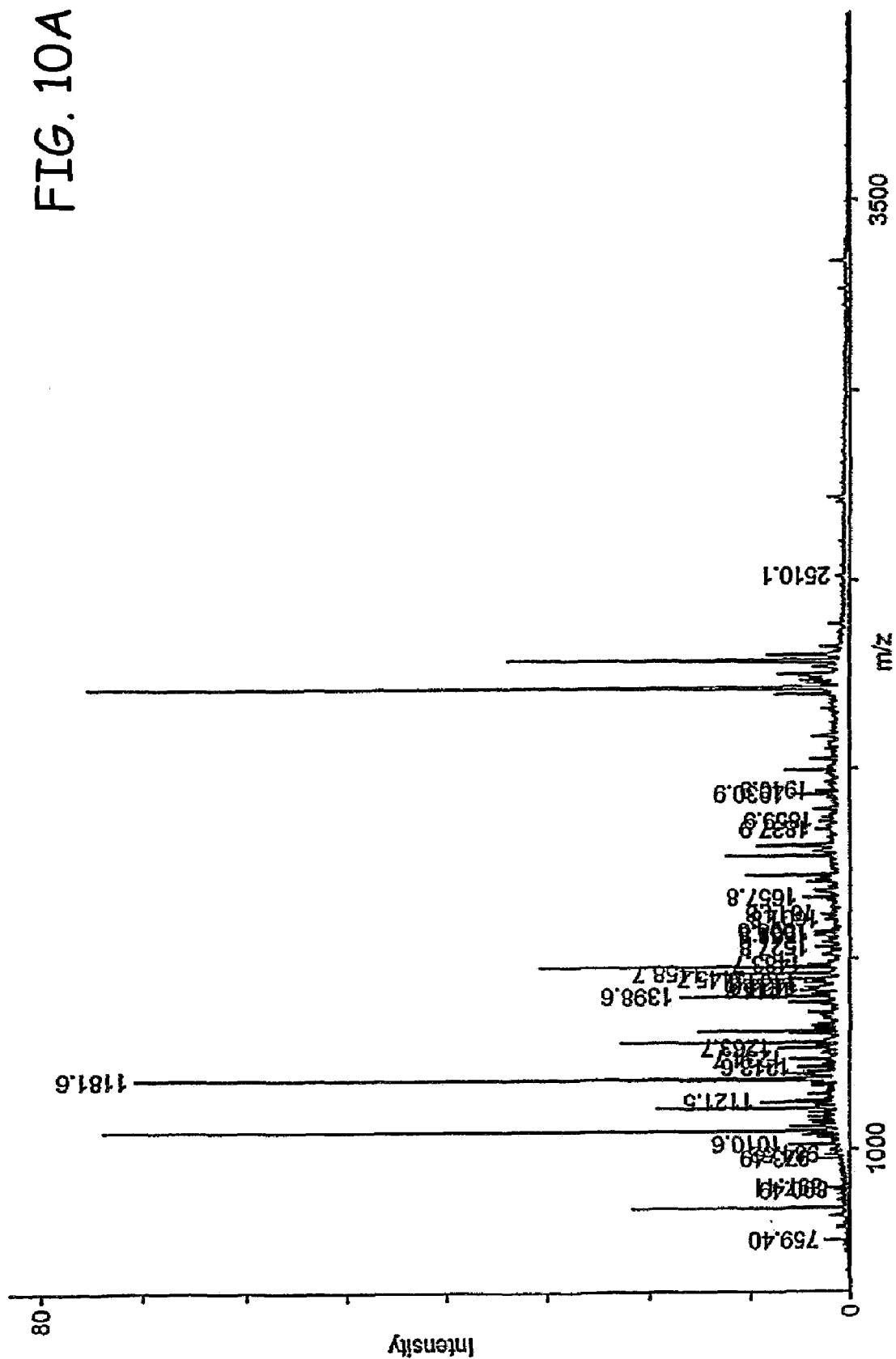
FIG. 10A is a total mass spectrometric graph with peak molecular weights noted in Daltons for IEF protein I 961 prepared from tryptic peptide fragments.
Figure 10B:
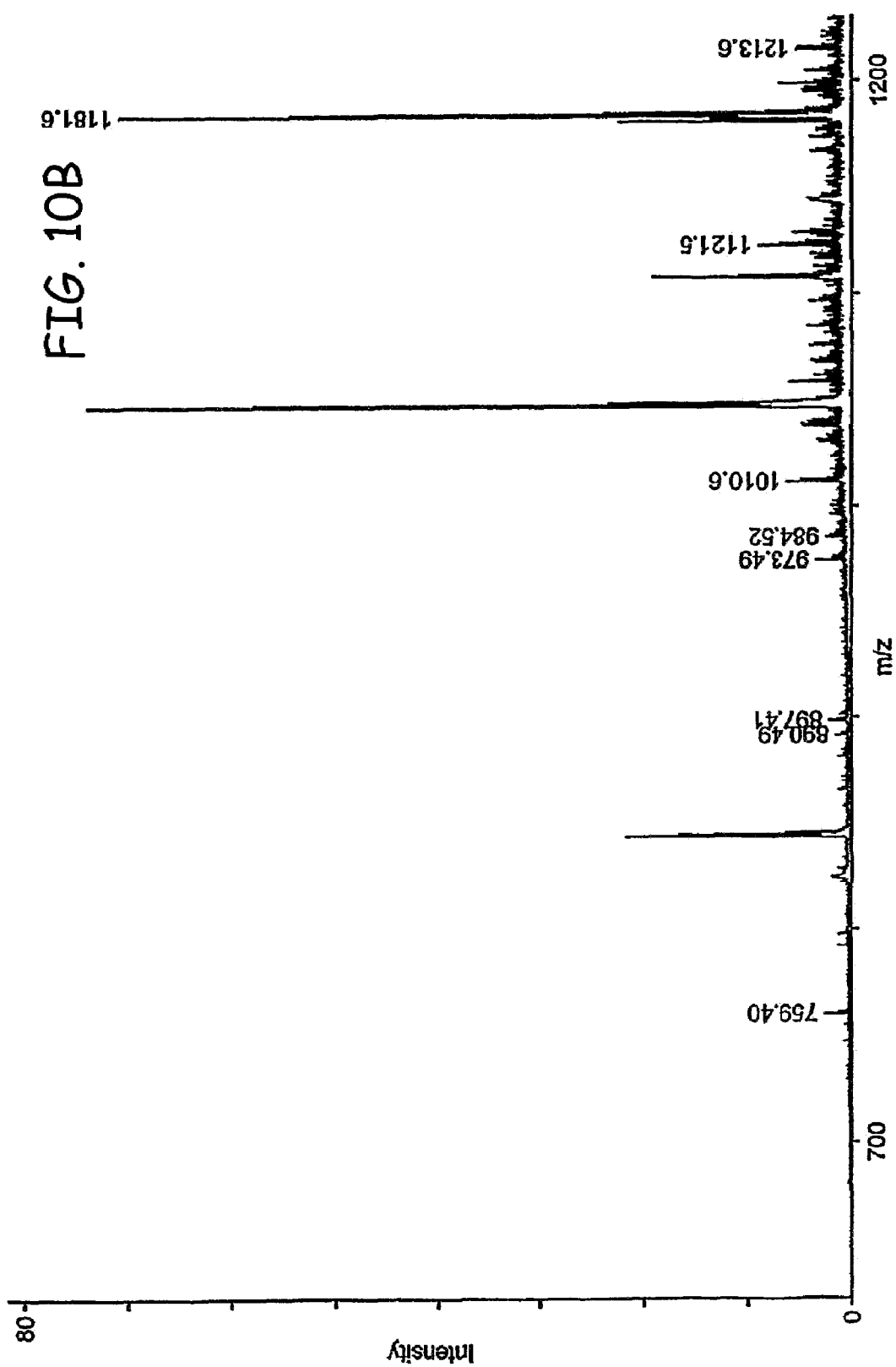
FIGS. 10B-10E represent enlarged regions of FIG. 10A for protein I 961 such that particular peaks may be readily identified.
Figure 10C:
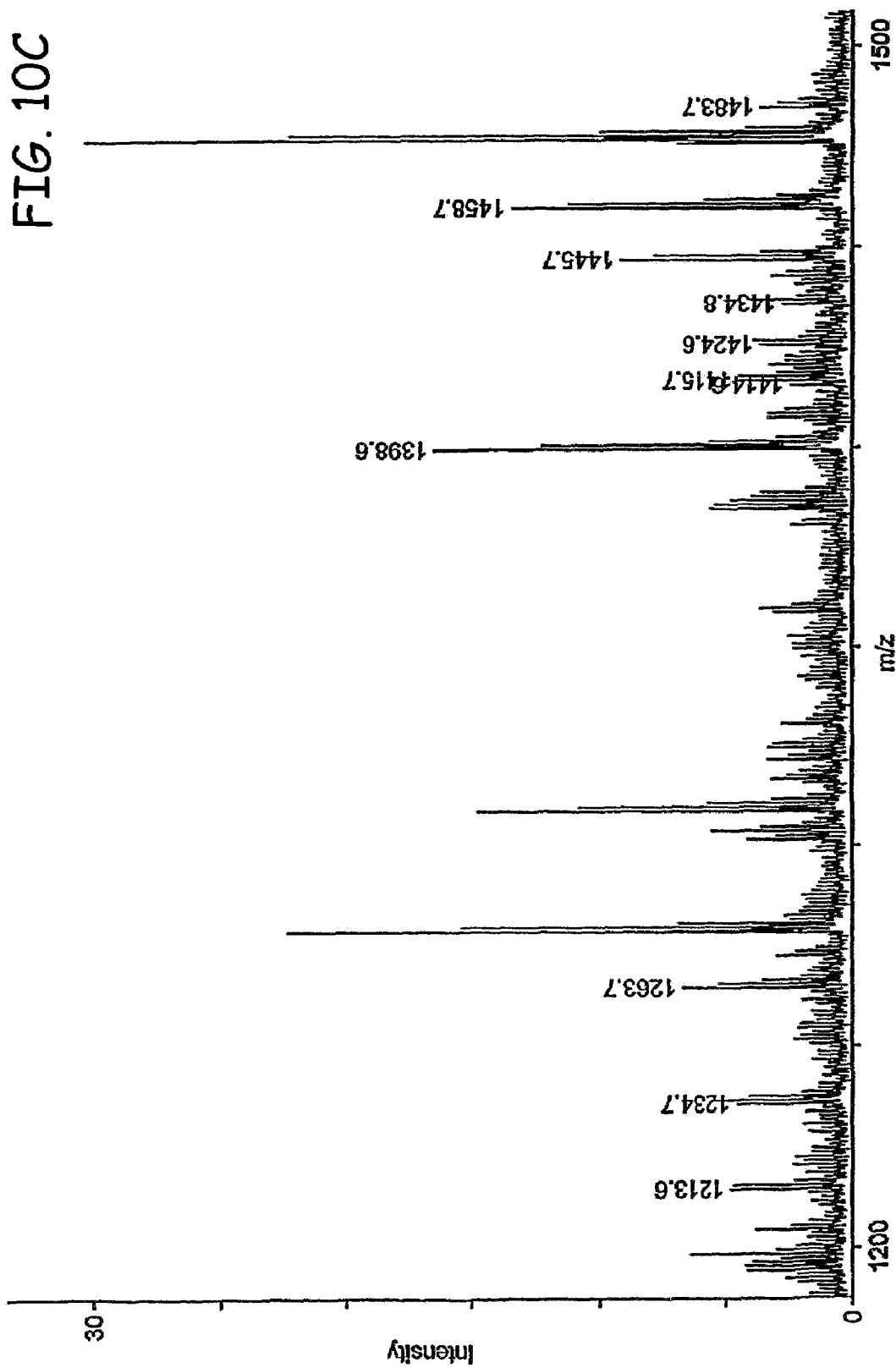
Figure 10D:
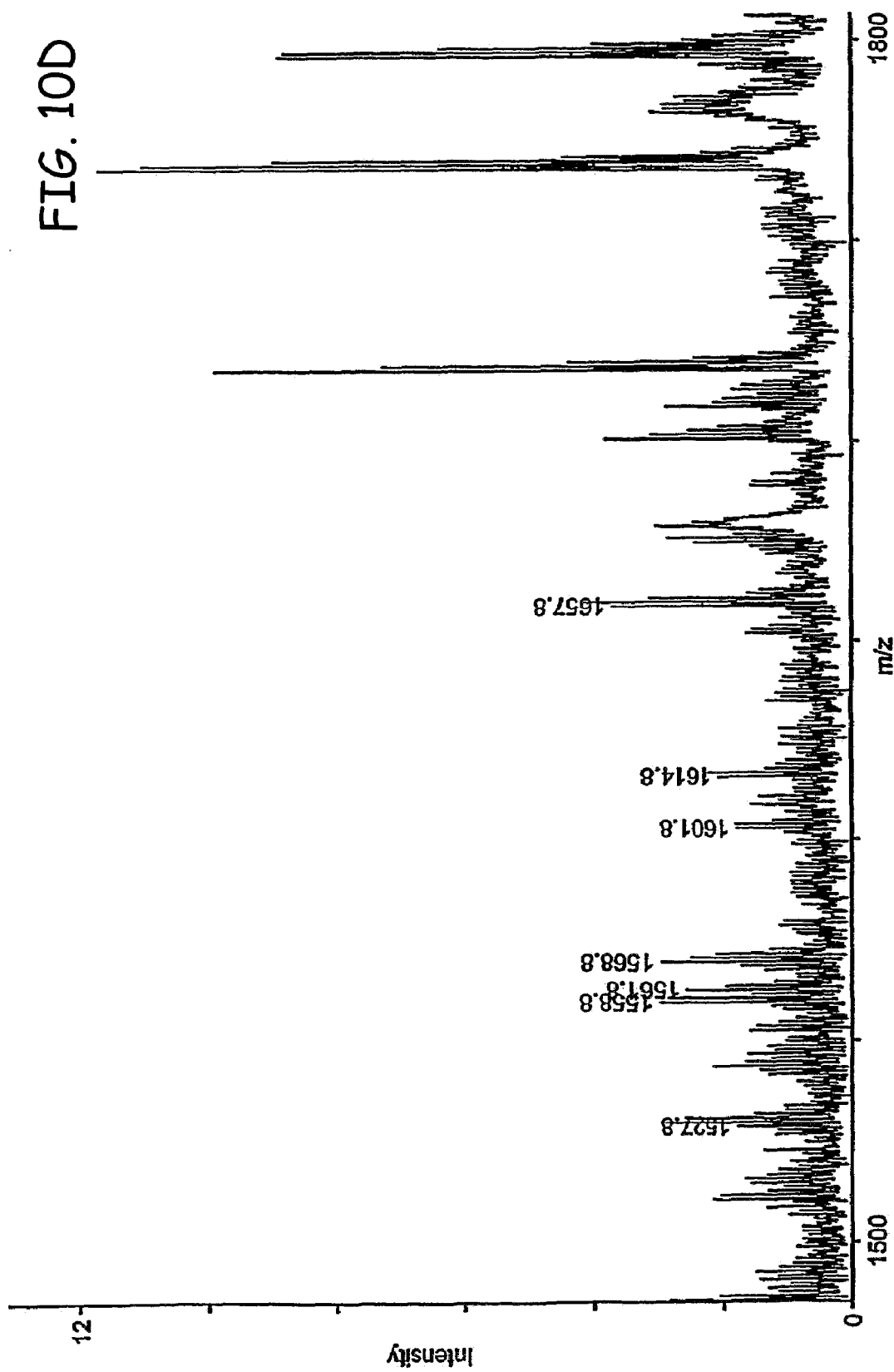
Figure 10E:
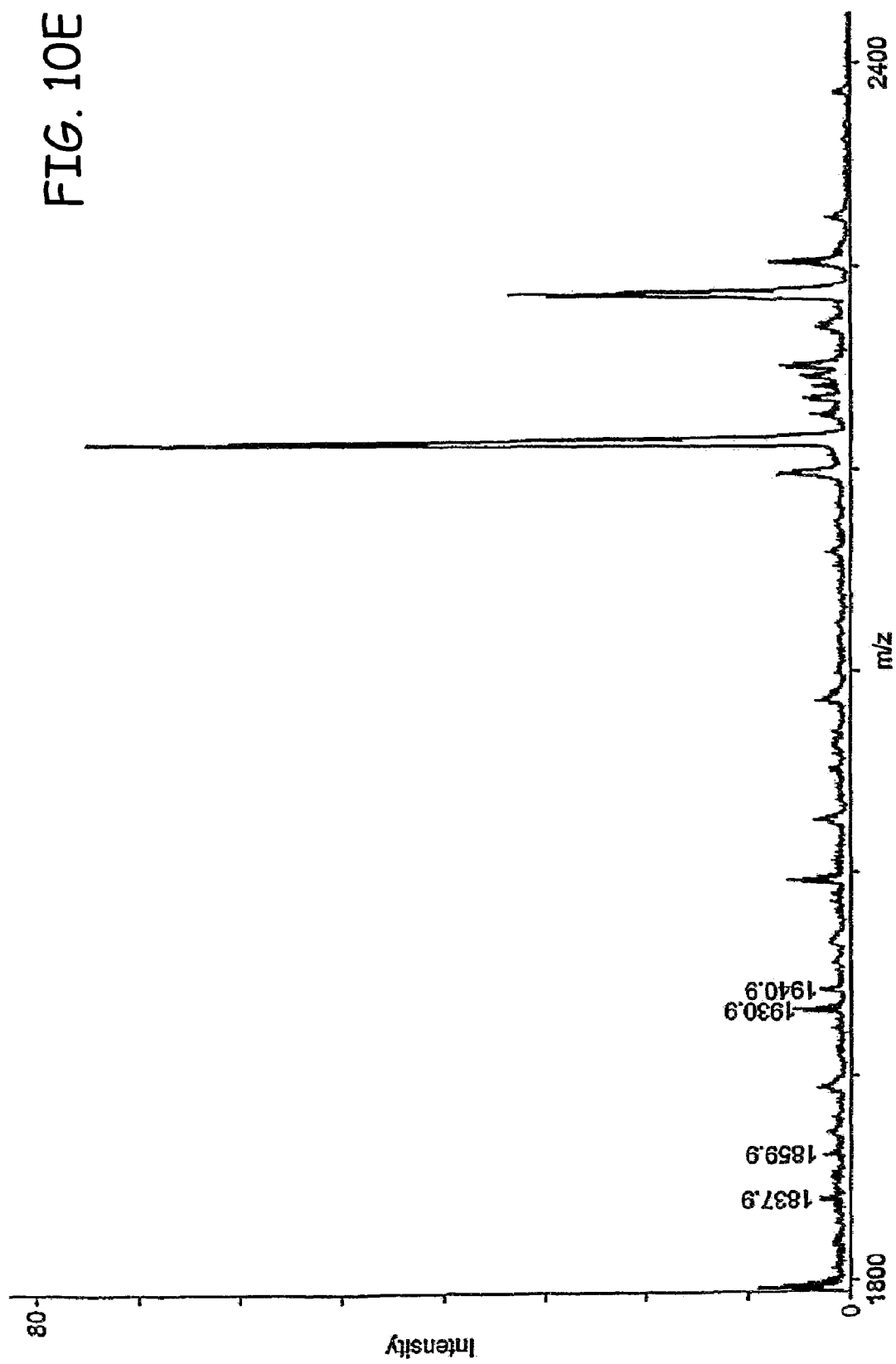
Figure 11A:
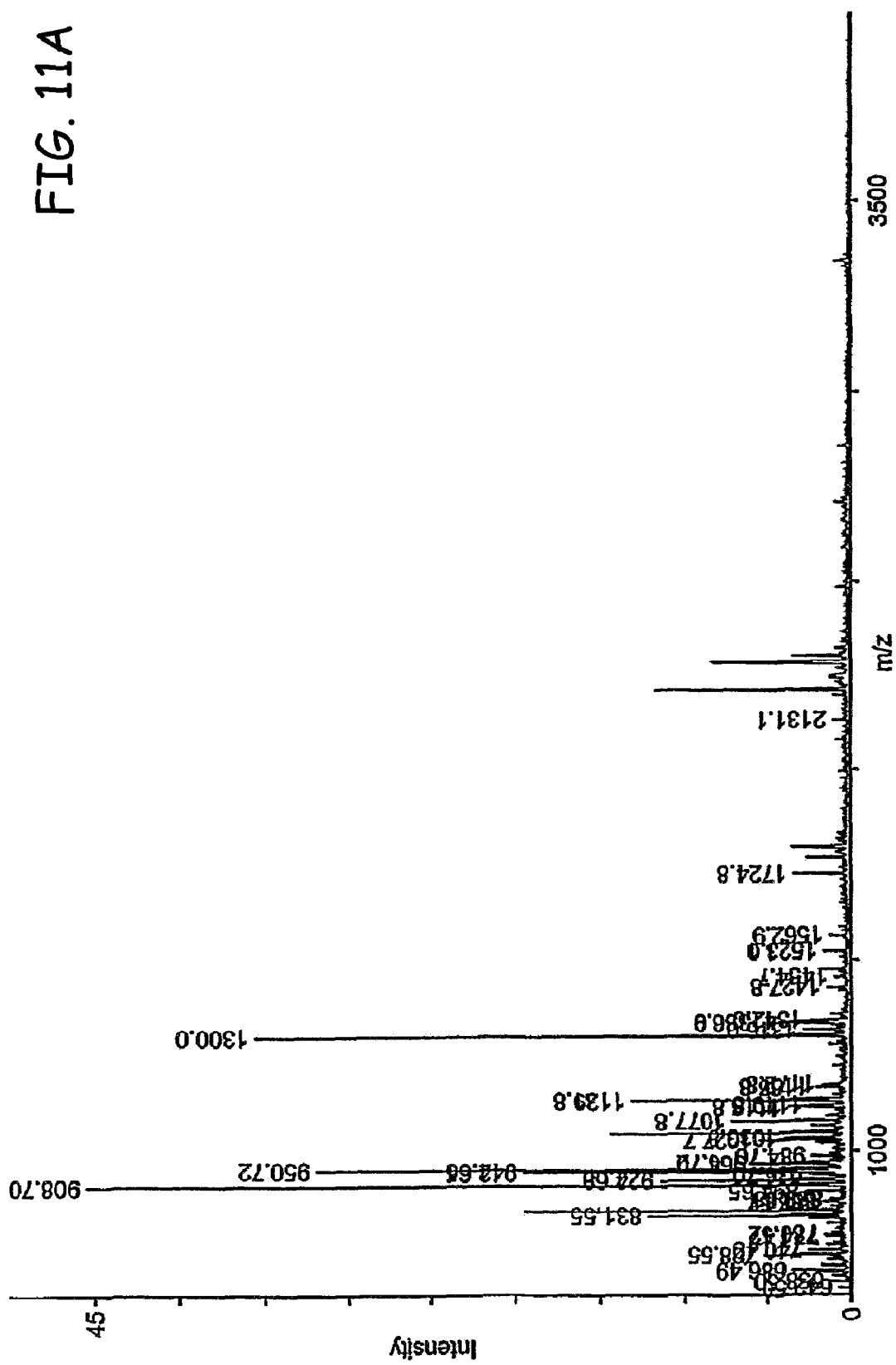
FIG. 11A is a total mass spectrometric graph with peak molecular weights noted in Daltons for IEF protein I 8264 prepared from tryptic peptide fragments.
Figure 11B:
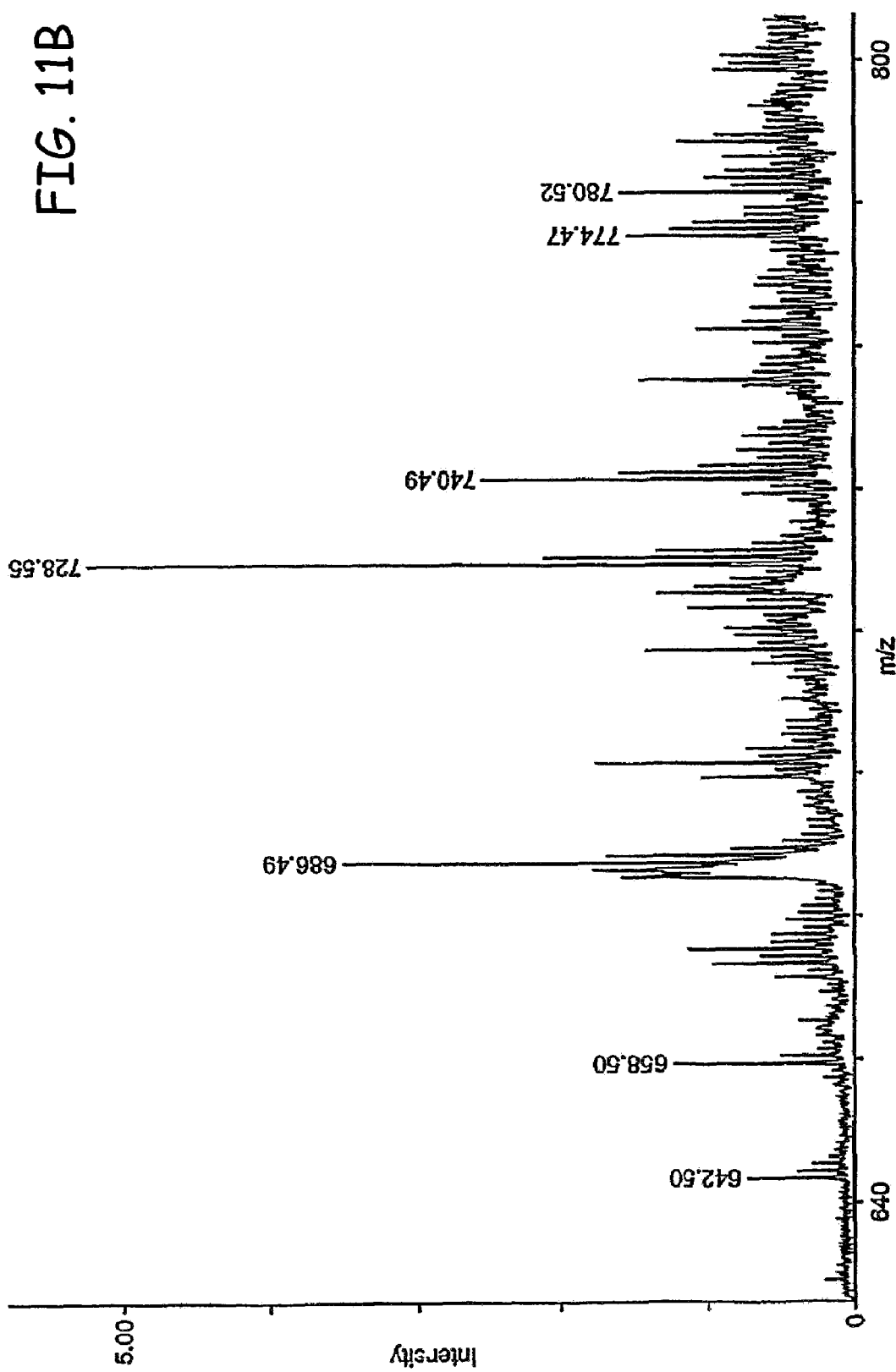
Figure 11C:
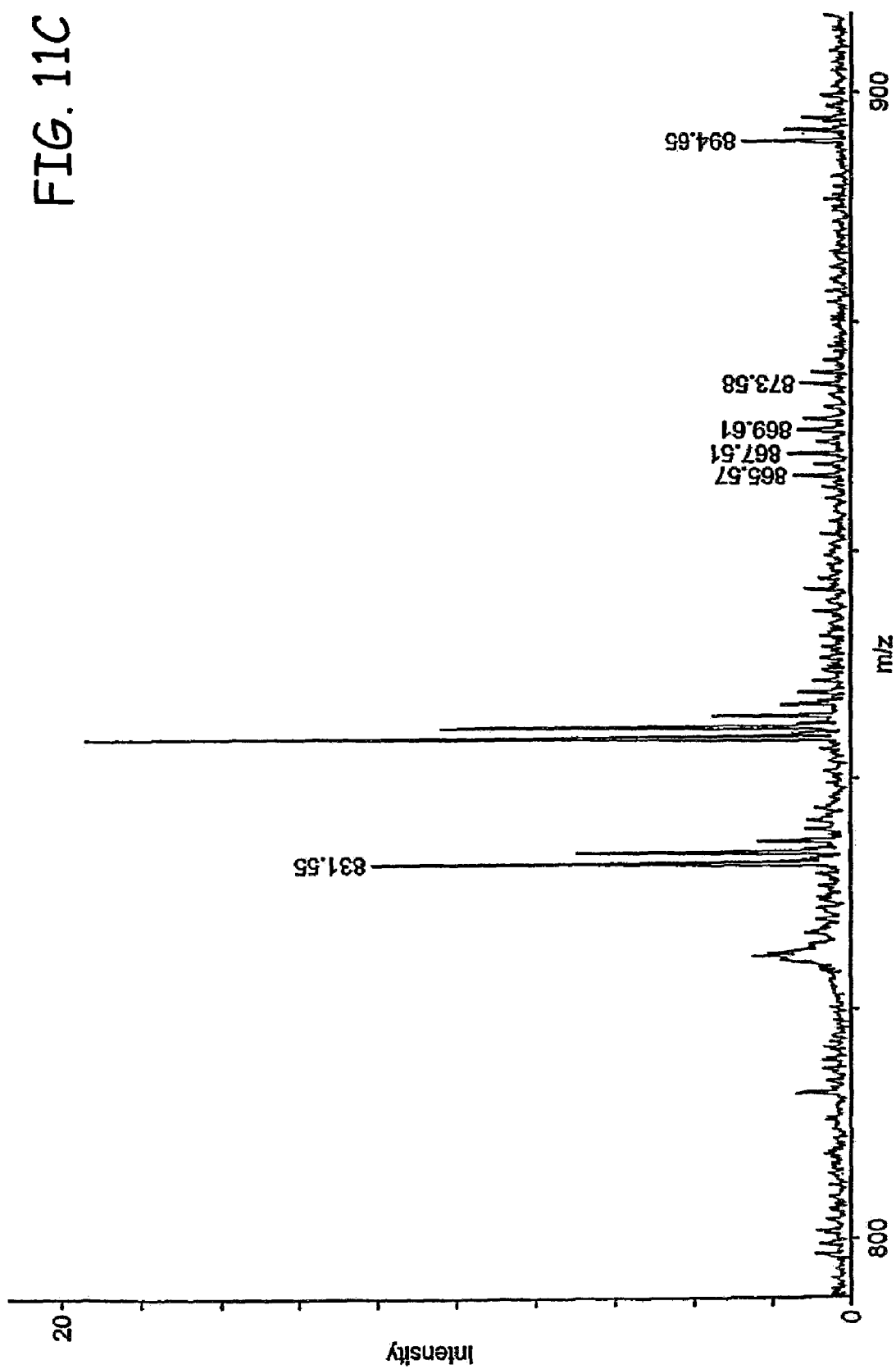
Figure 11D:
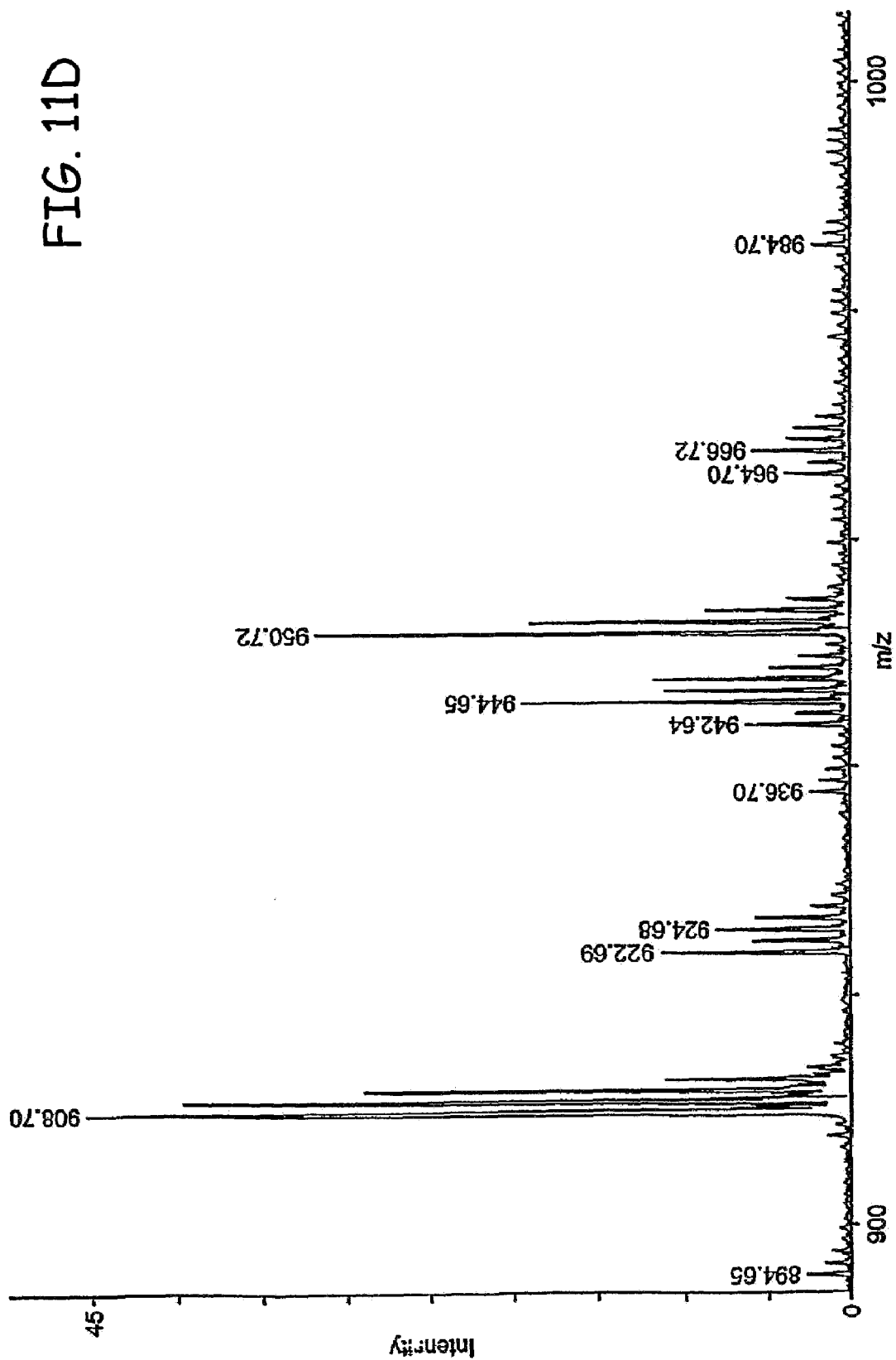
Figure 11E:
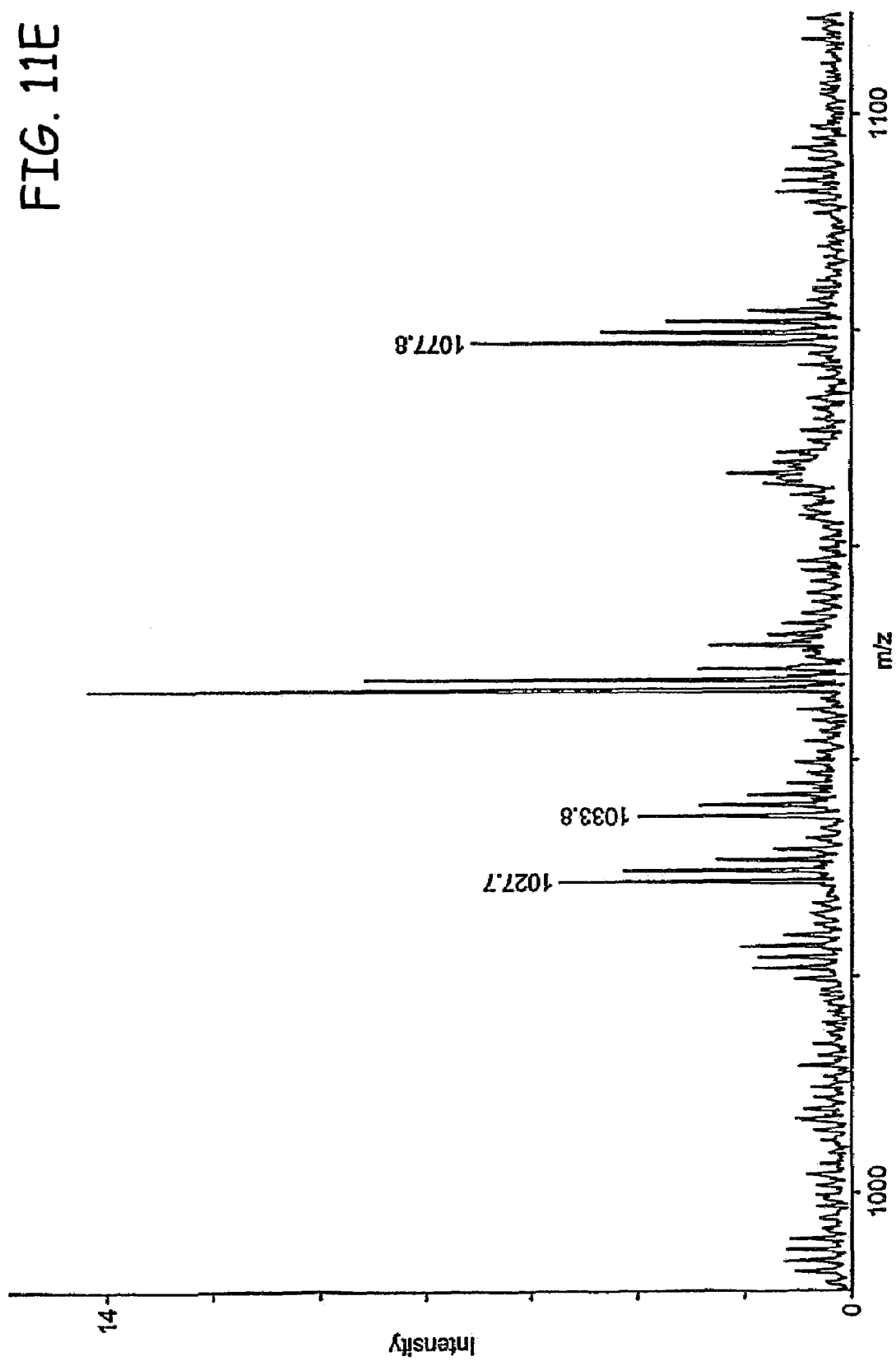
Figure 11F:
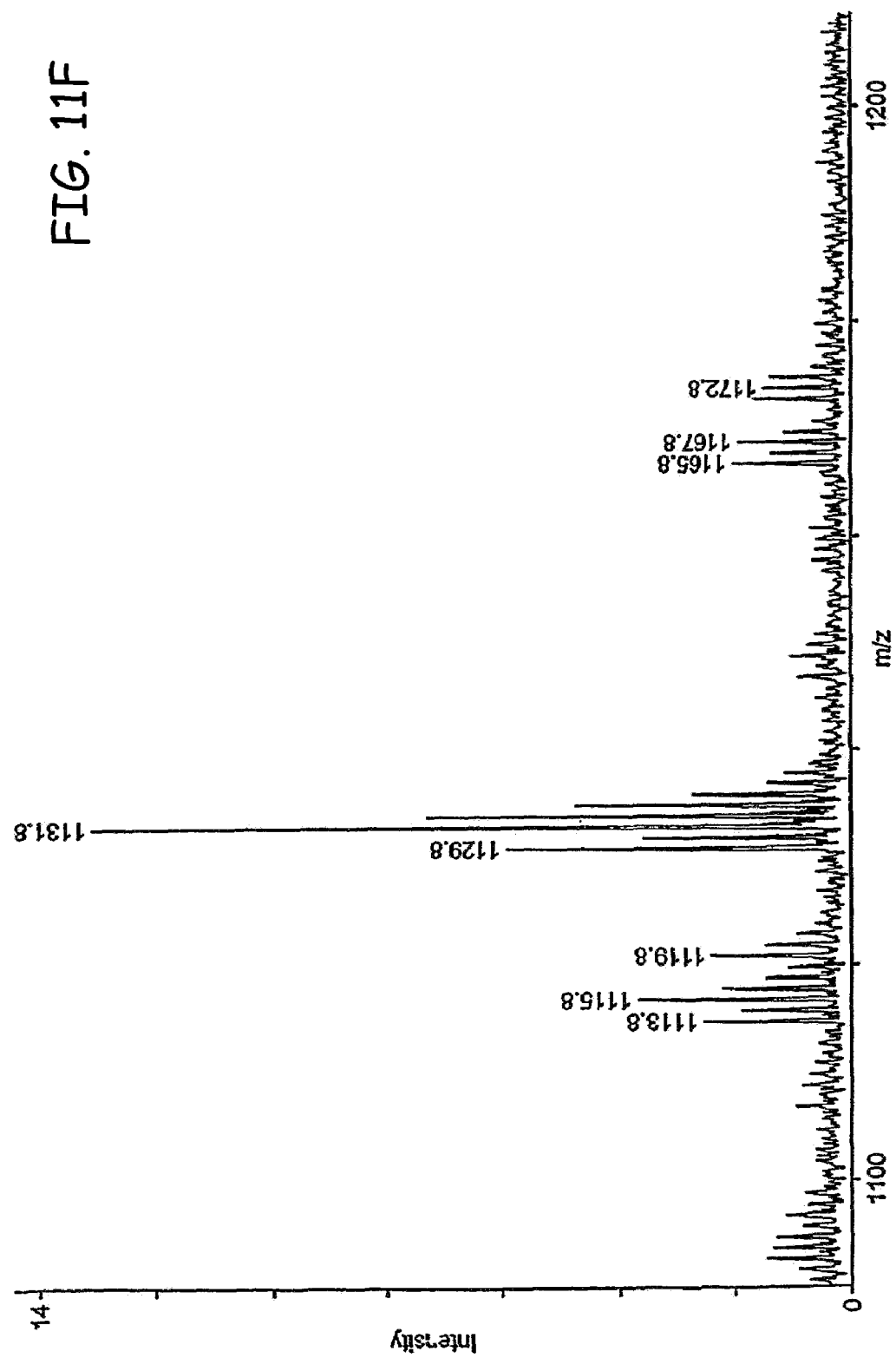
Figure 116:
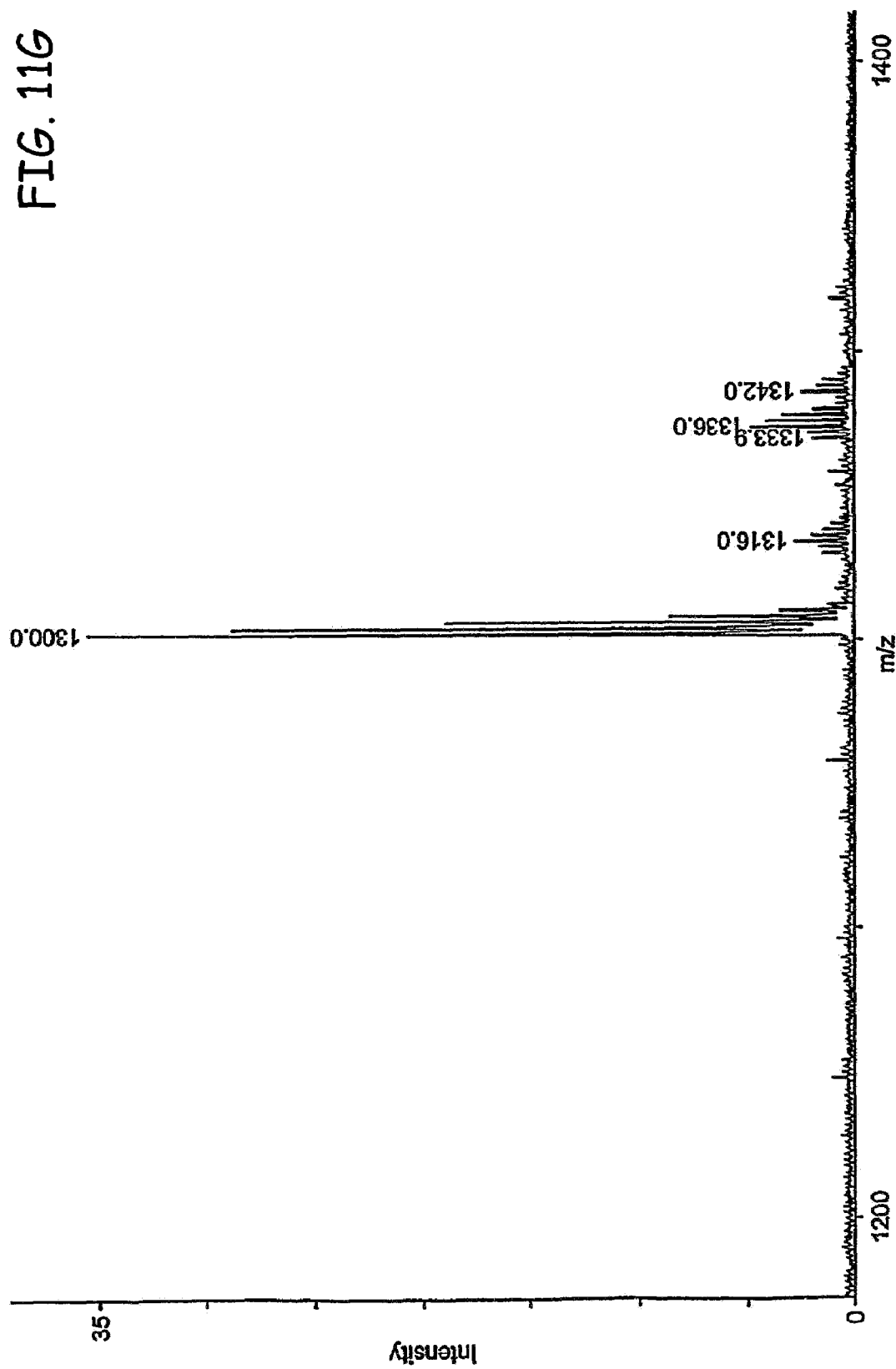
Figure 11H:
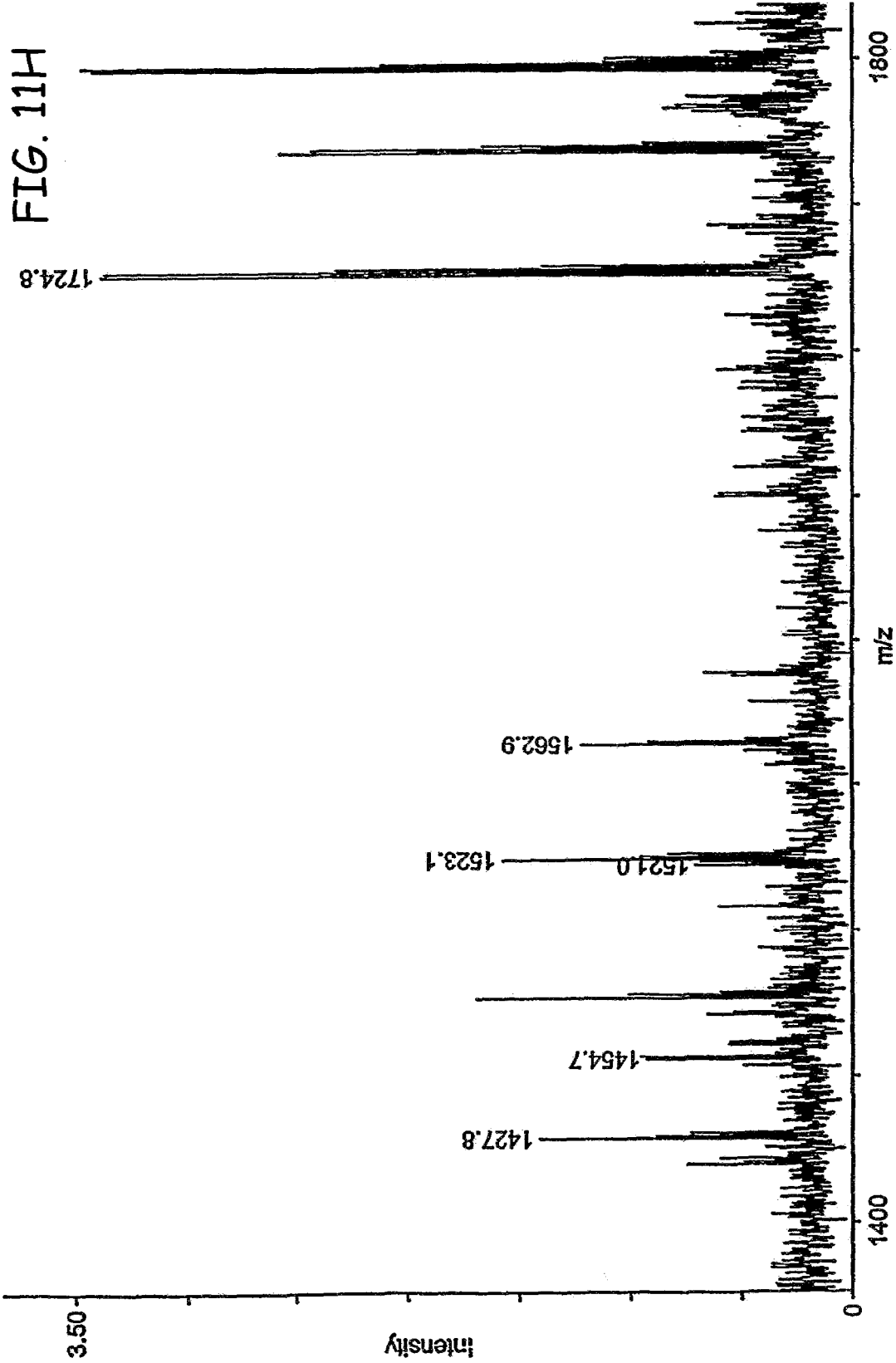
Figure 12A:
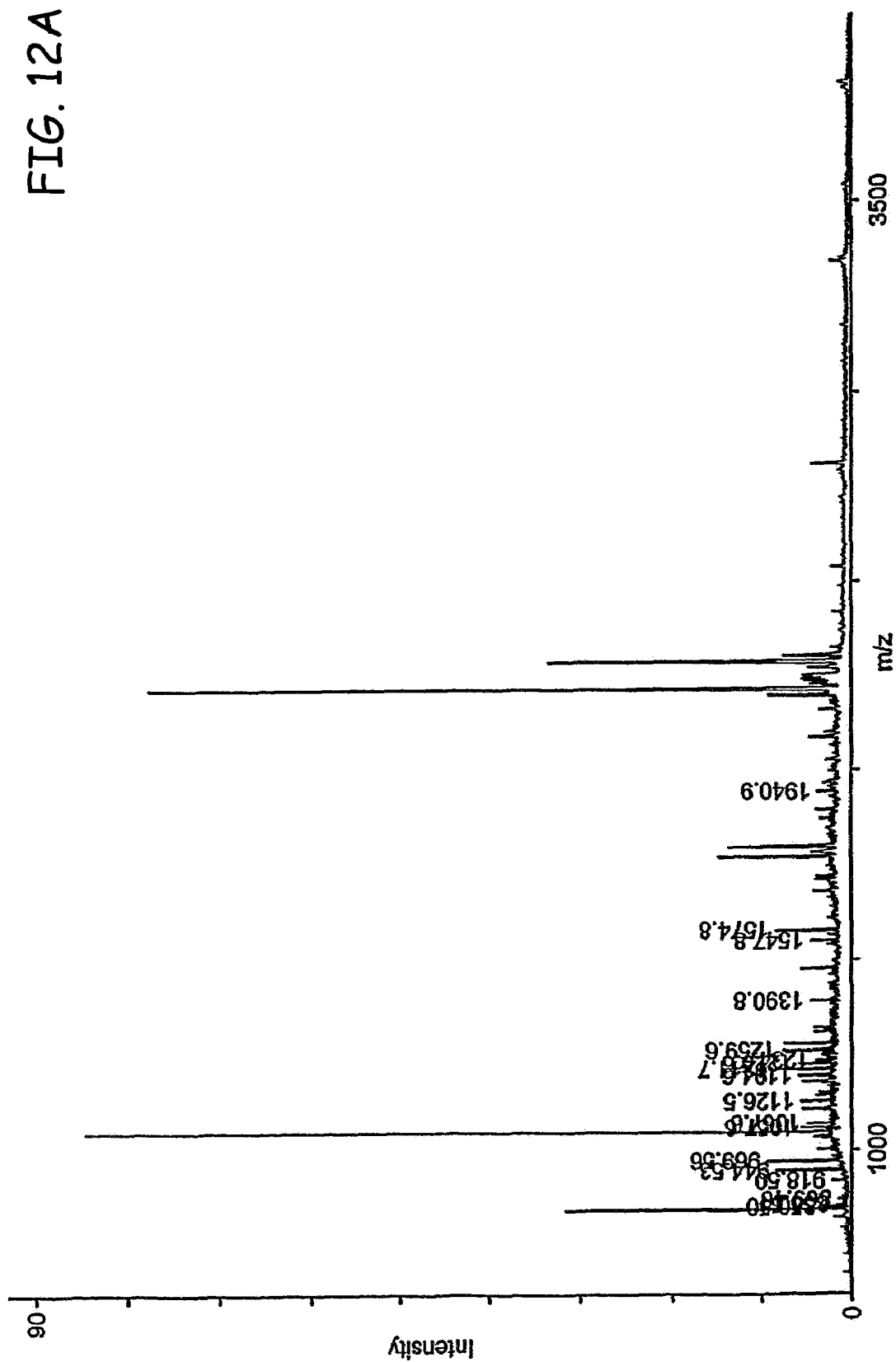
FIG. 12A is a total mass spectrometric graph with peak molecular weights noted in Daltons for IEF protein I 8311 prepared from tryptic peptide fragments.
Figure 12B:
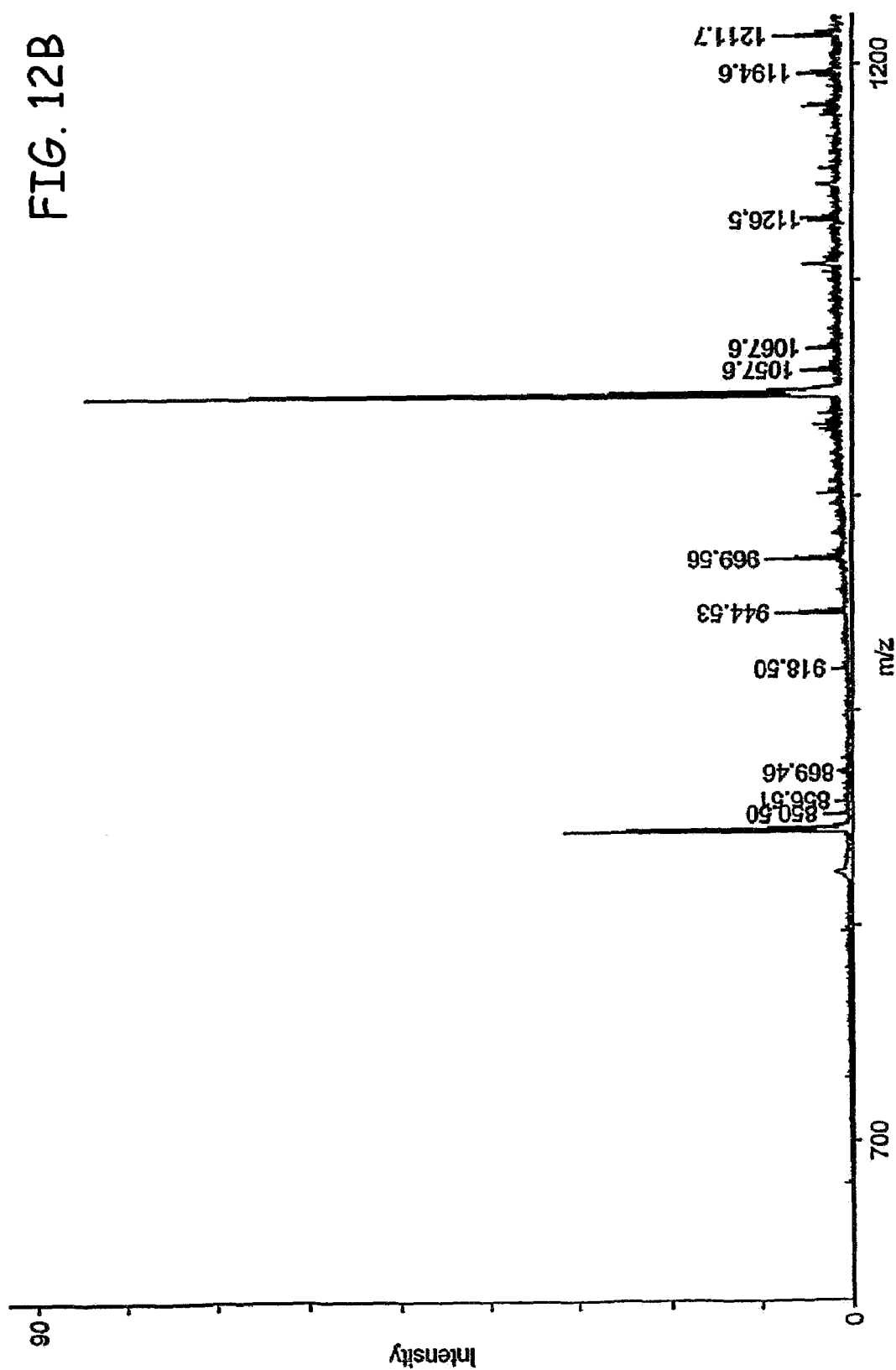
FIGS. 12B-12C represent enlarged regions of FIG. 12A for protein I 8311 such that particular peaks may be readily identified.
Figure 12C:
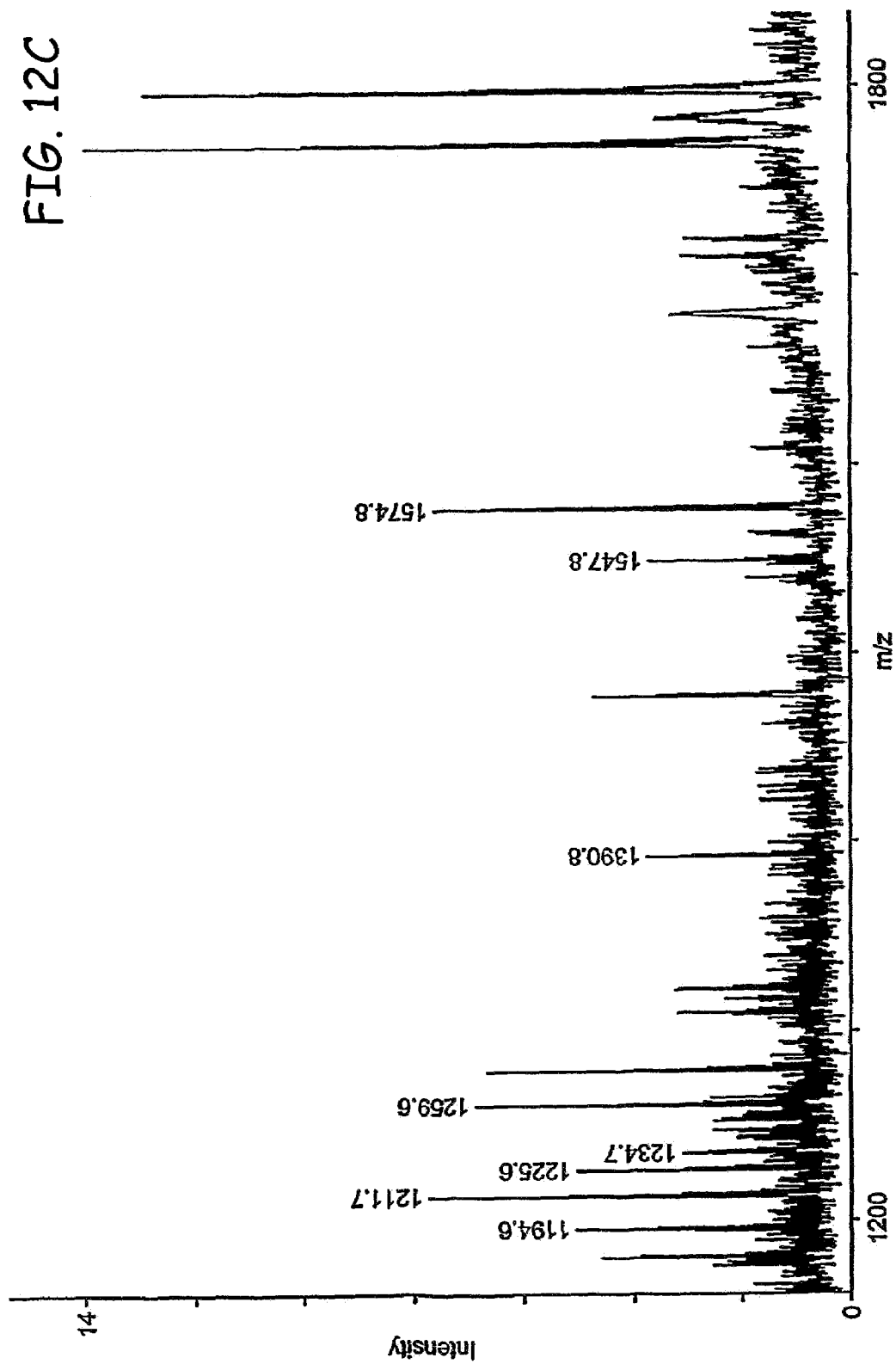
Figure 13A:
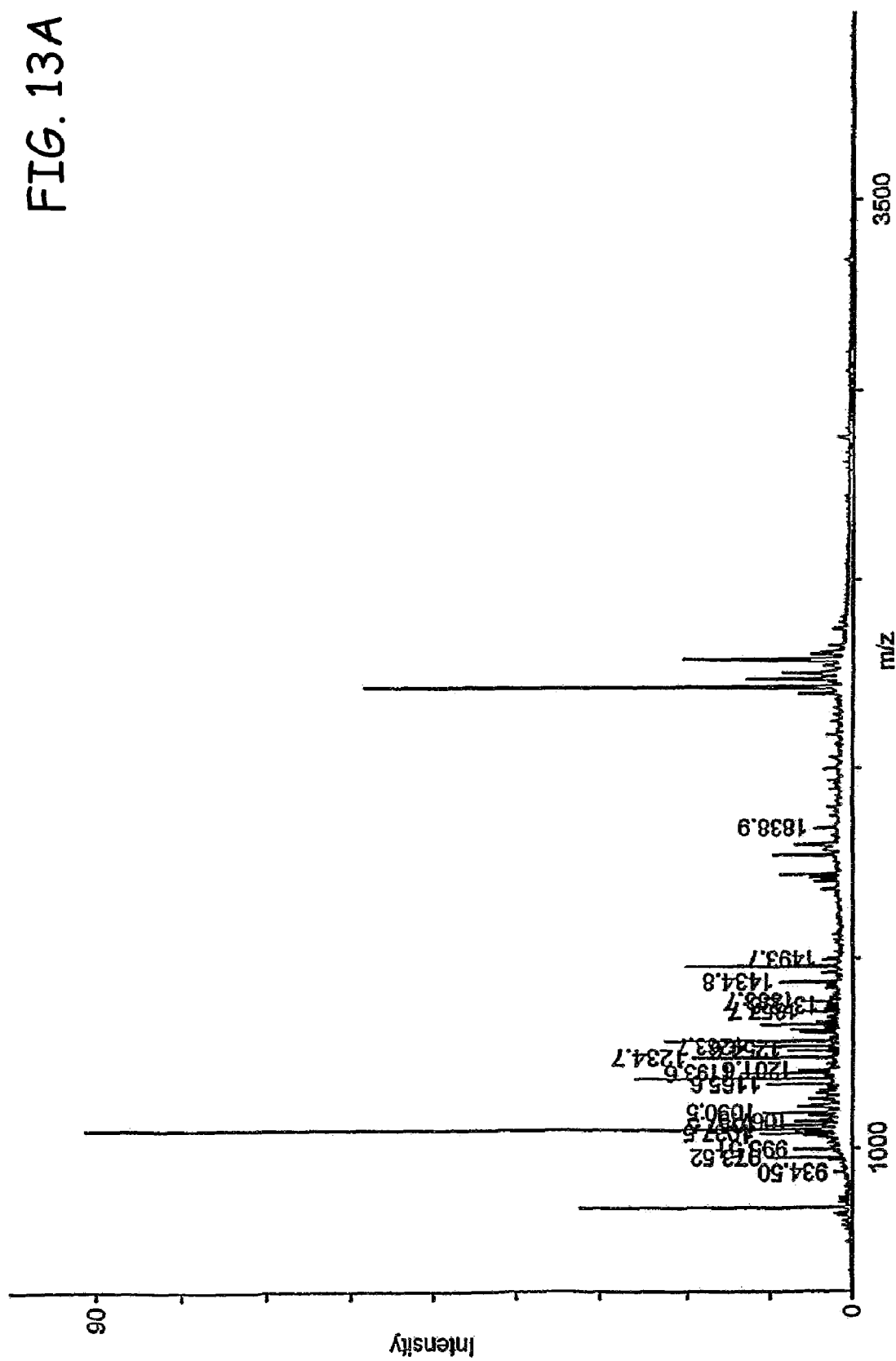
FIG. 13A is a total mass spectrometric graph with peak molecular weights noted in Daltons for NEPHGE protein N 68 prepared from tryptic peptide fragments.
Figure 13B:
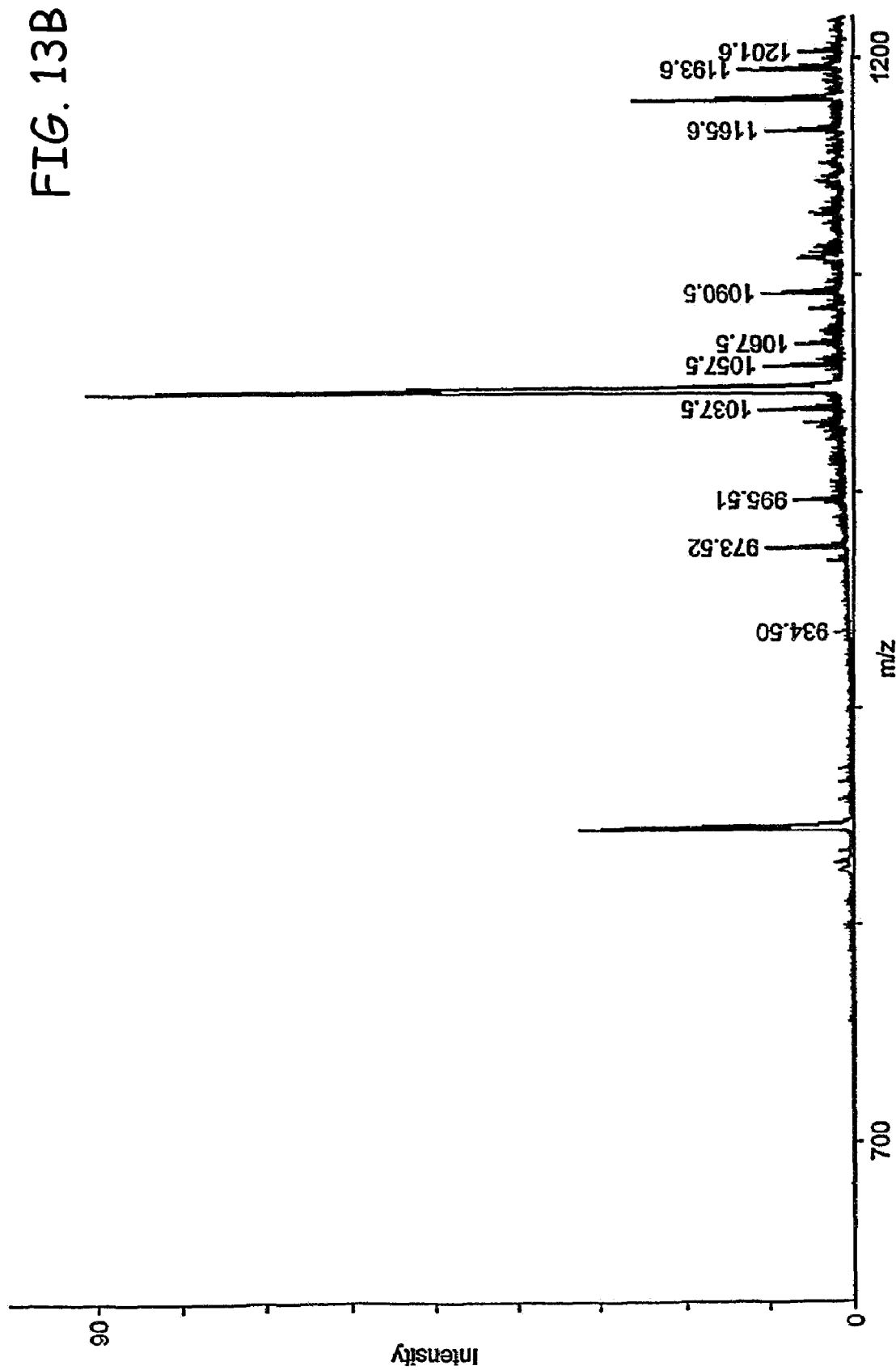
FIGS. 13B-13C represent enlarged regions of FIG. 13A for protein N 68 such that particular peaks may be readily identified.
Figure 13C:
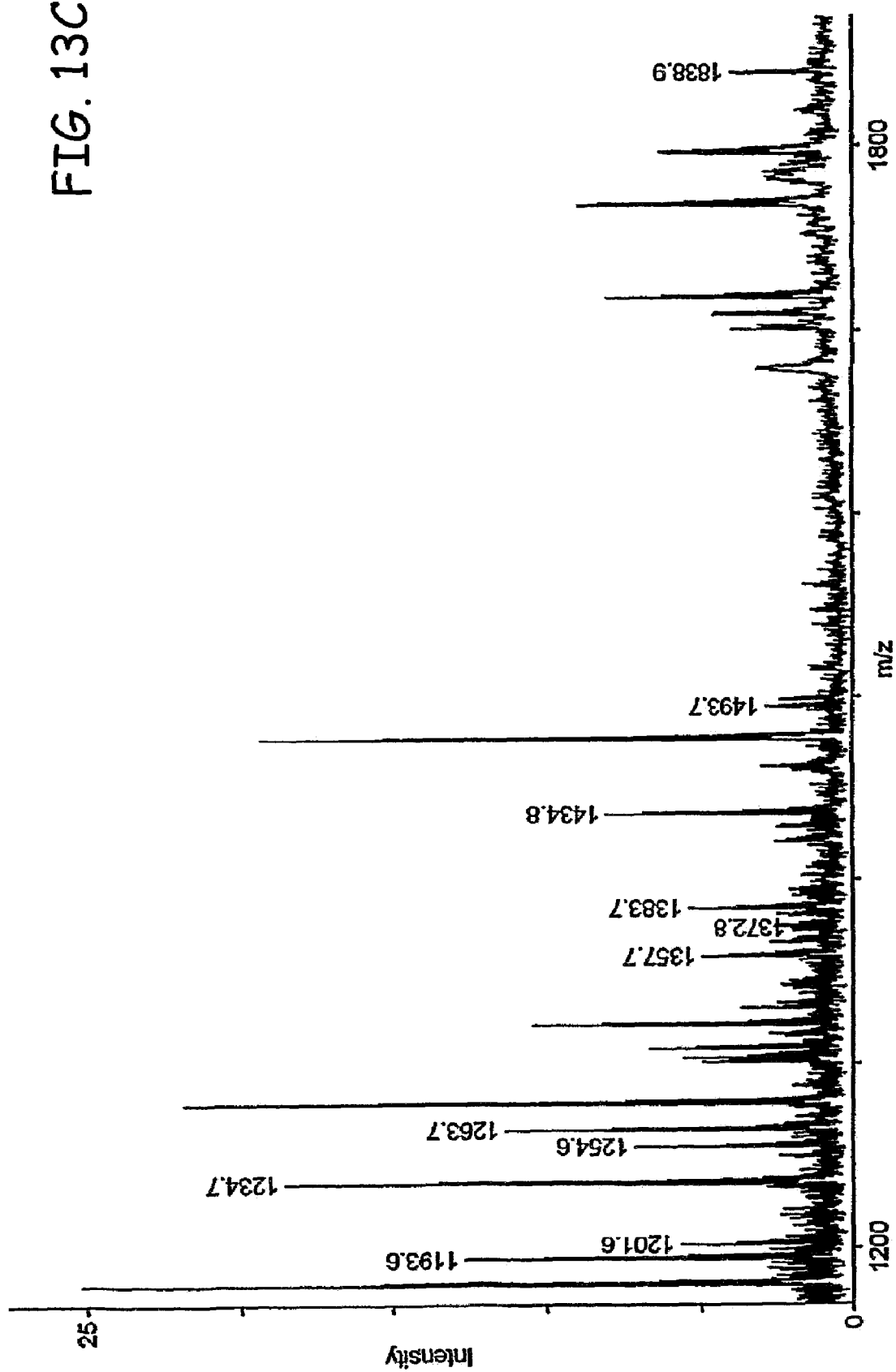
Figure 14A:
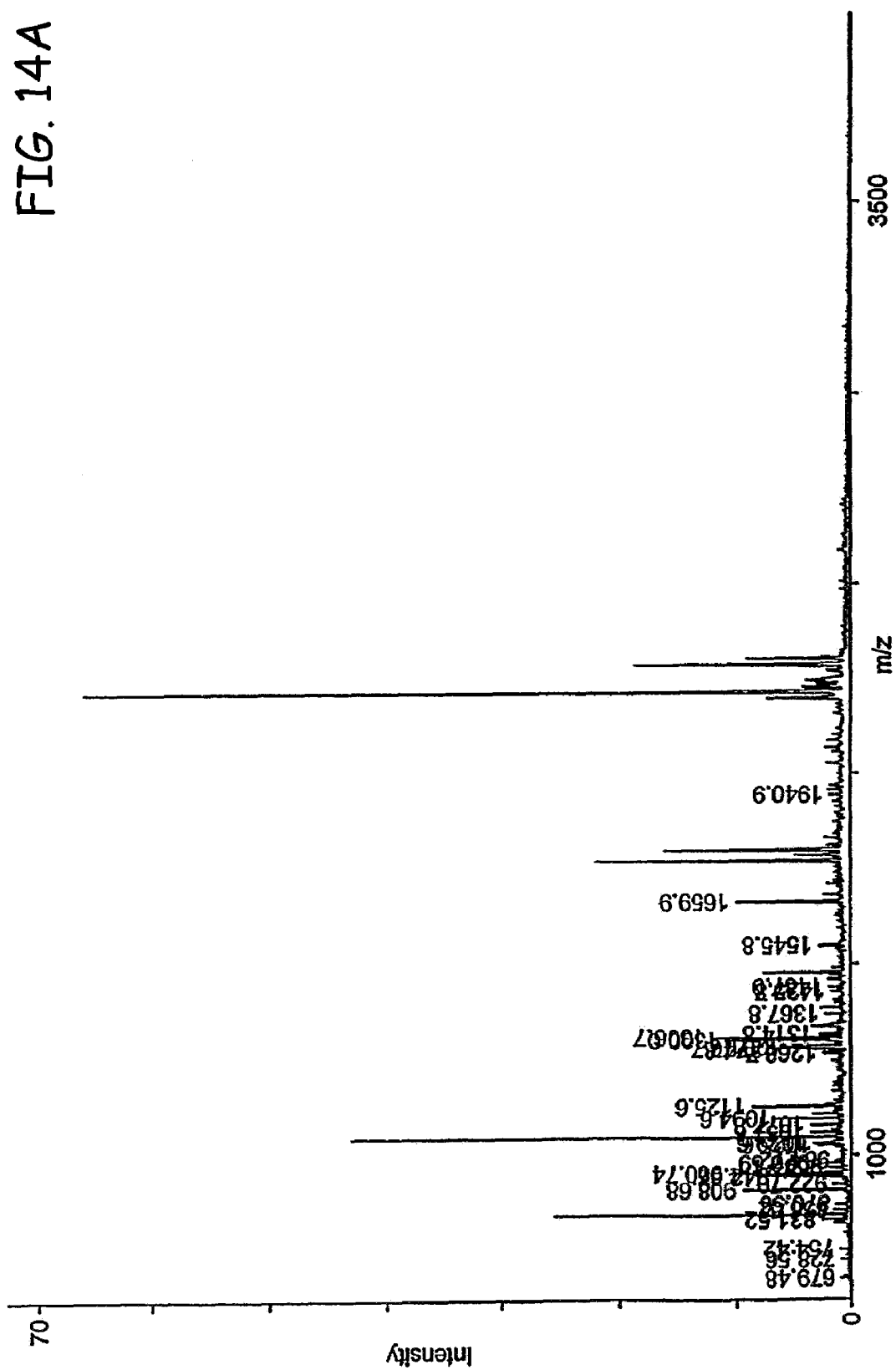
FIG. 14A is a total mass spectrometric graph with peak molecular weights noted in Daltons for NEPHGE protein N 212 prepared from tryptic peptide fragments.
Figure 14B:
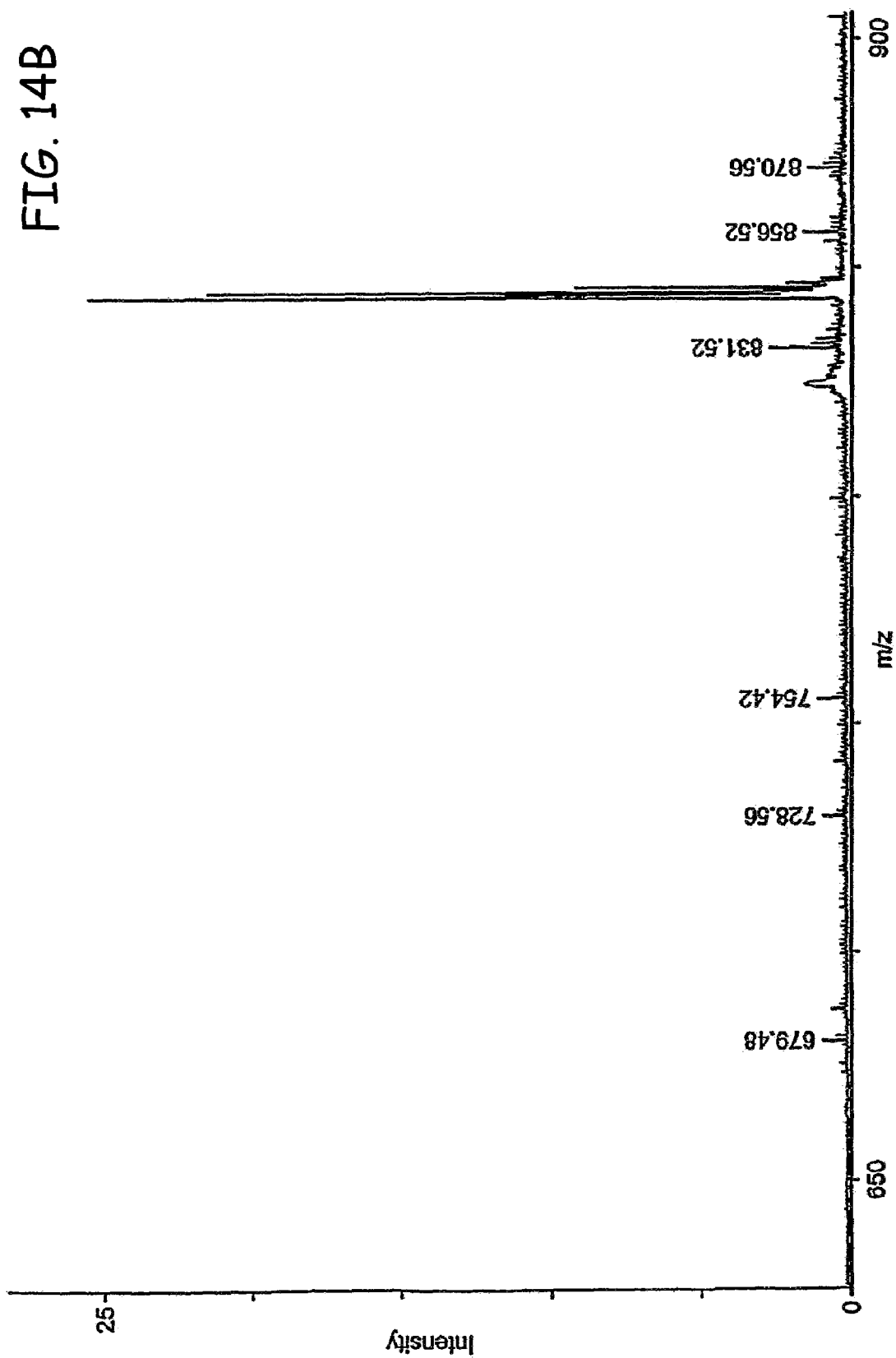
FIGS. 14B-14E represent enlarged regions of FIG. 14A for protein N 212 such that particular peaks may be readily identified.
Figure 14C:
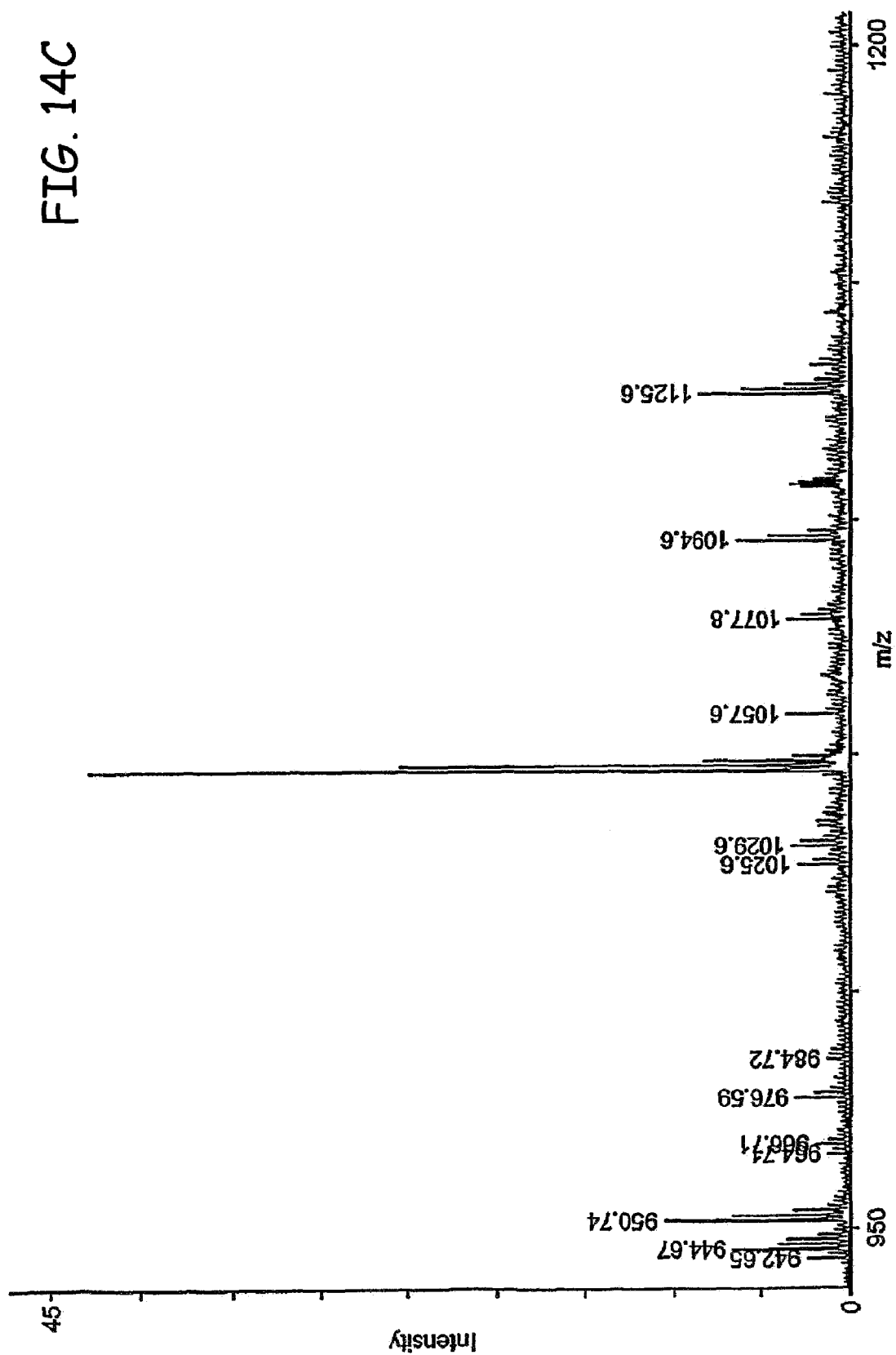
Figure 14D:
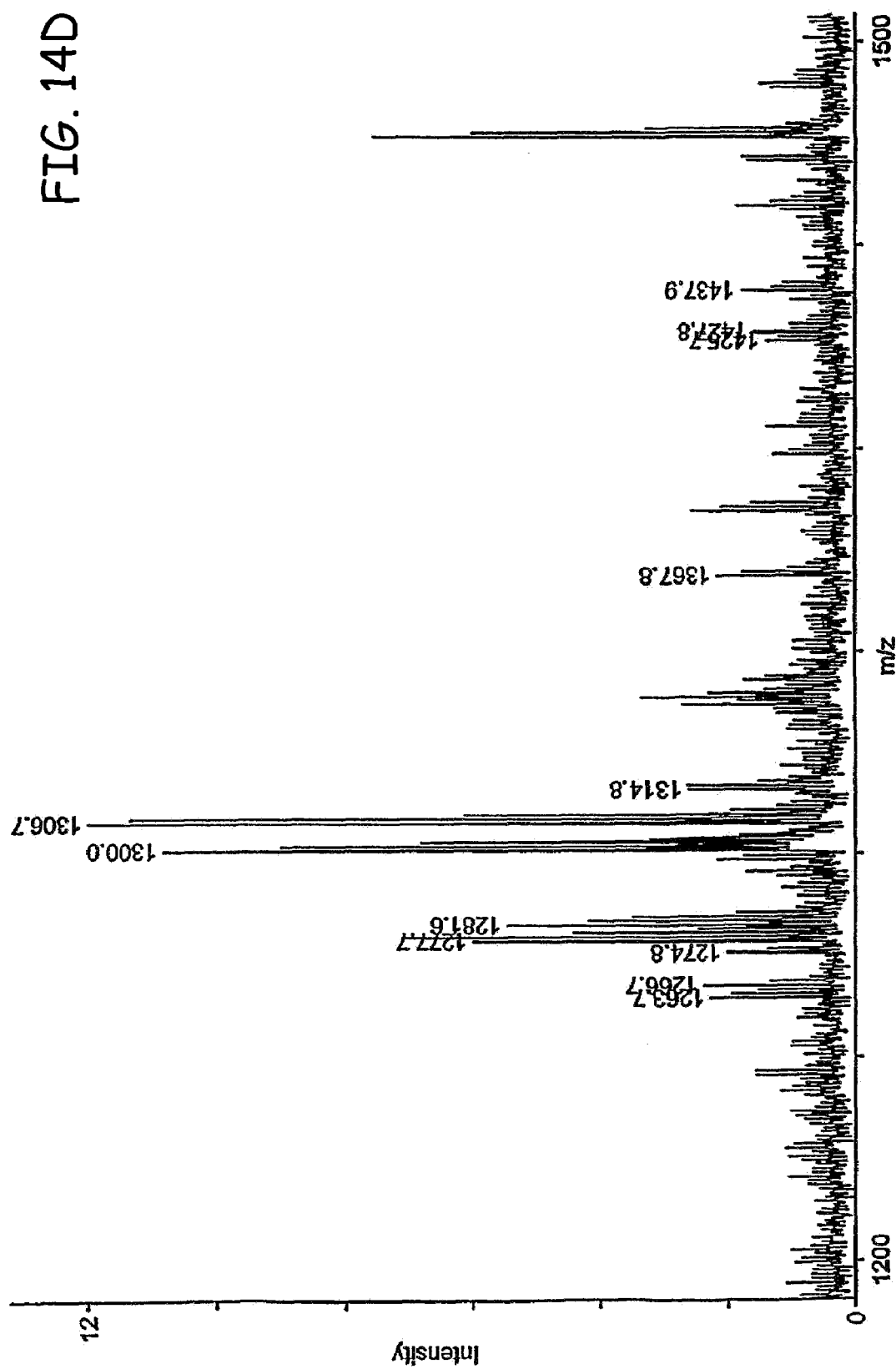
Figure 14E:
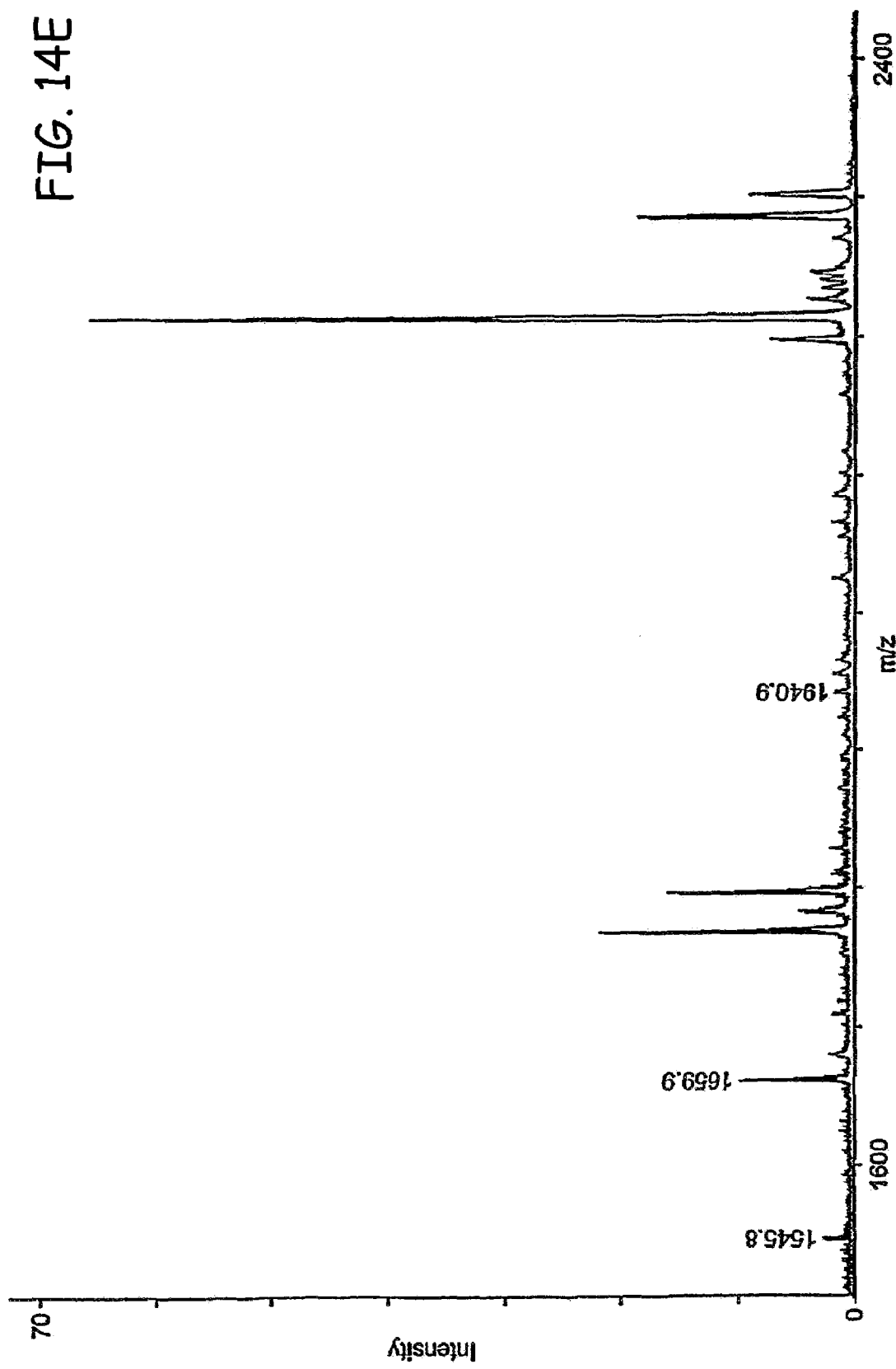
Figure 15A:
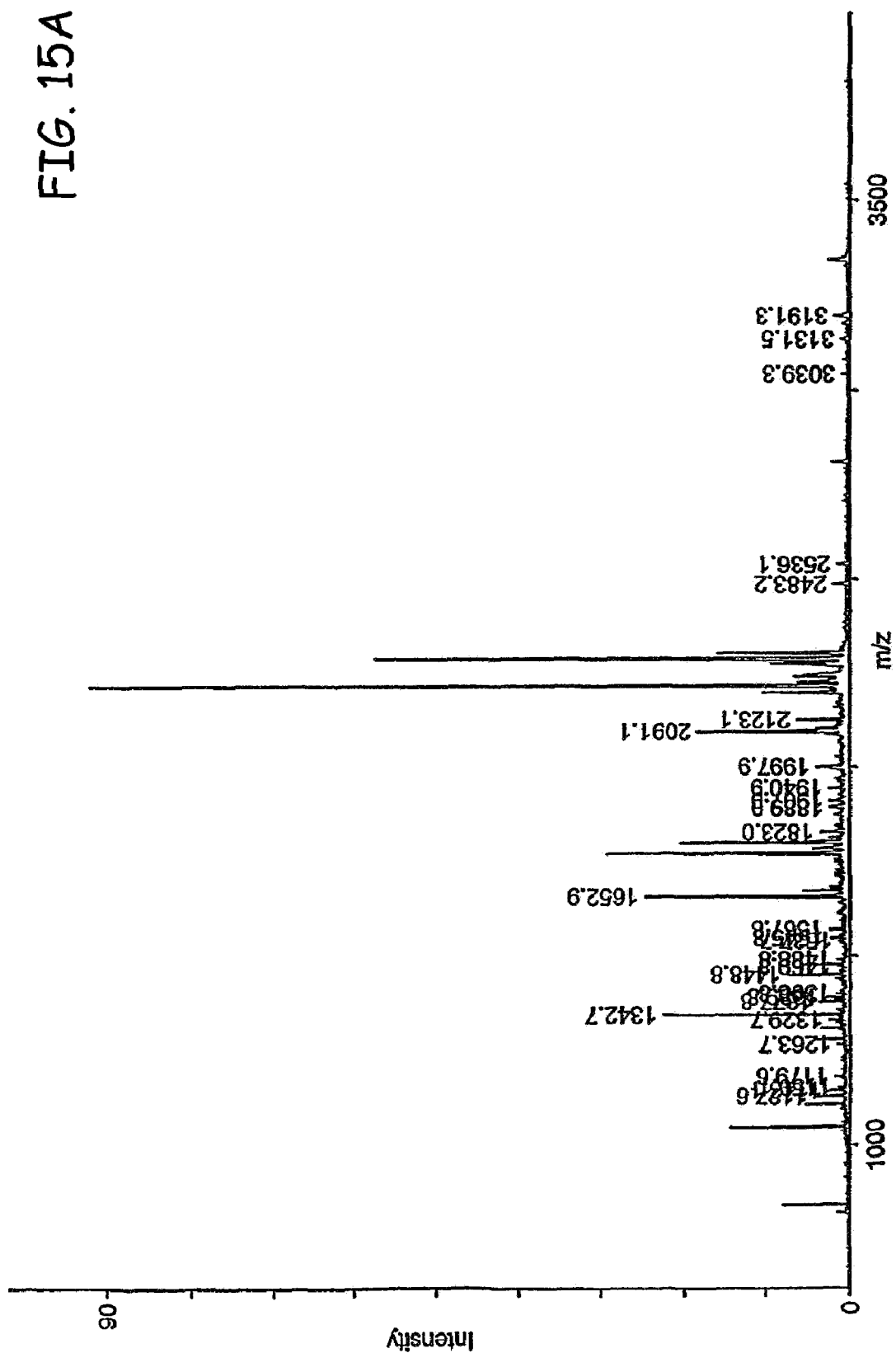
FIG. 15A is a total mass spectrometric graph with peak molecular weights noted in Daltons for NEPHGE protein N 268 prepared from tryptic peptide fragments.
Figure 15B:
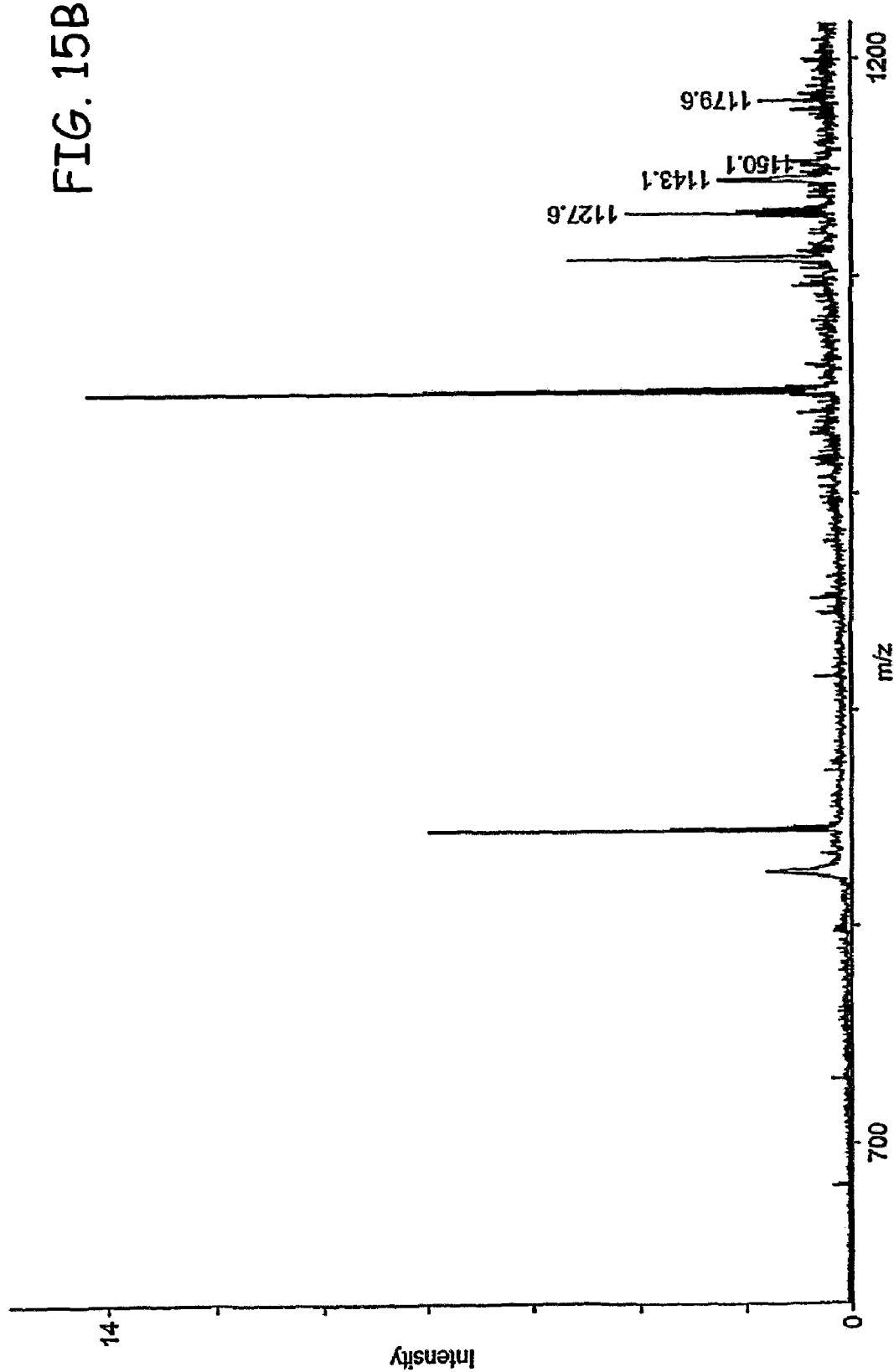
FIGS. 15B-15E represent enlarged regions of FIG. 15A for protein N 268 such that particular peaks may be readily identified.
Figure 15C:
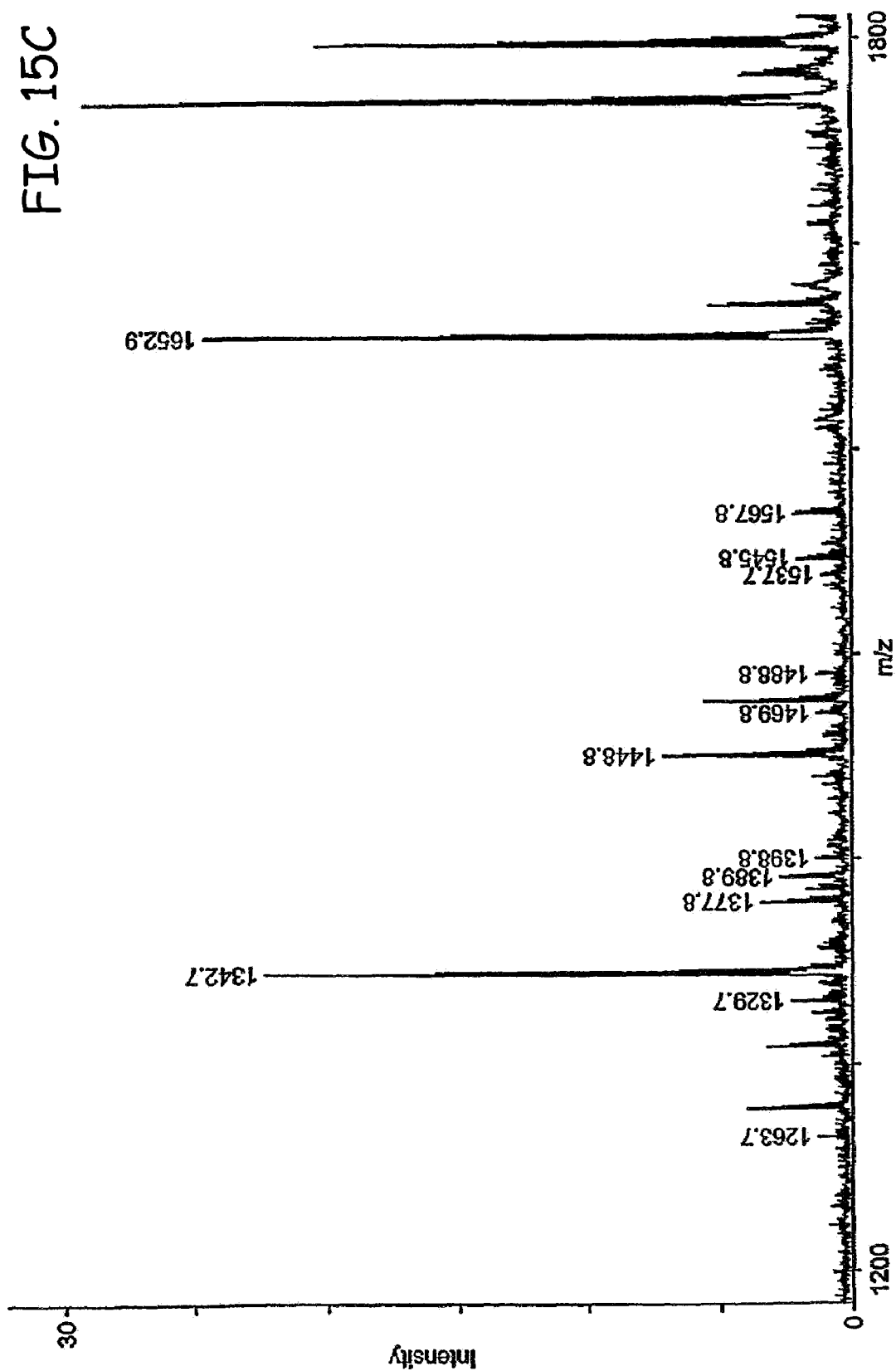
Figure 15D:
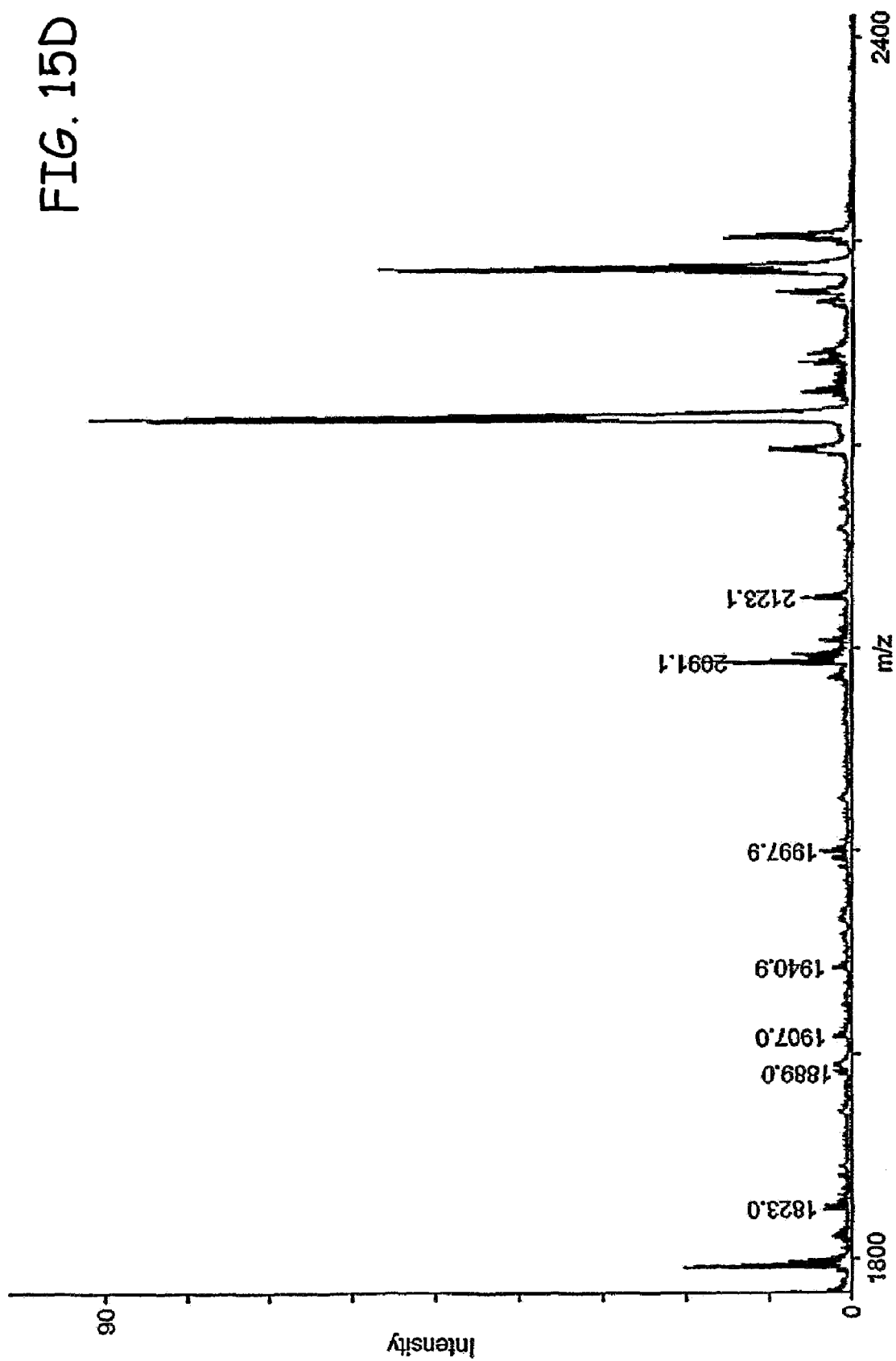
Figure 15E:
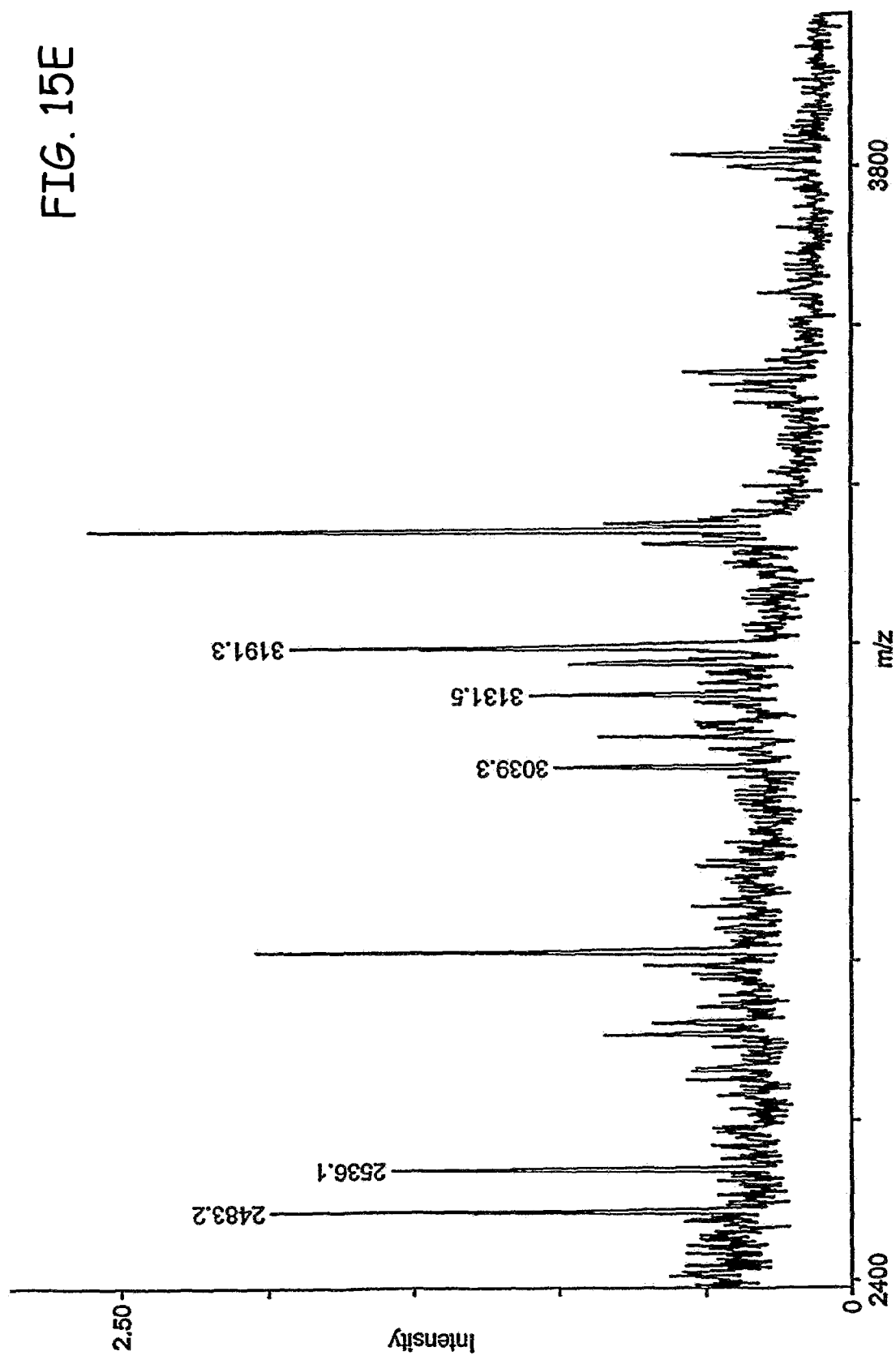
Figure 16A:
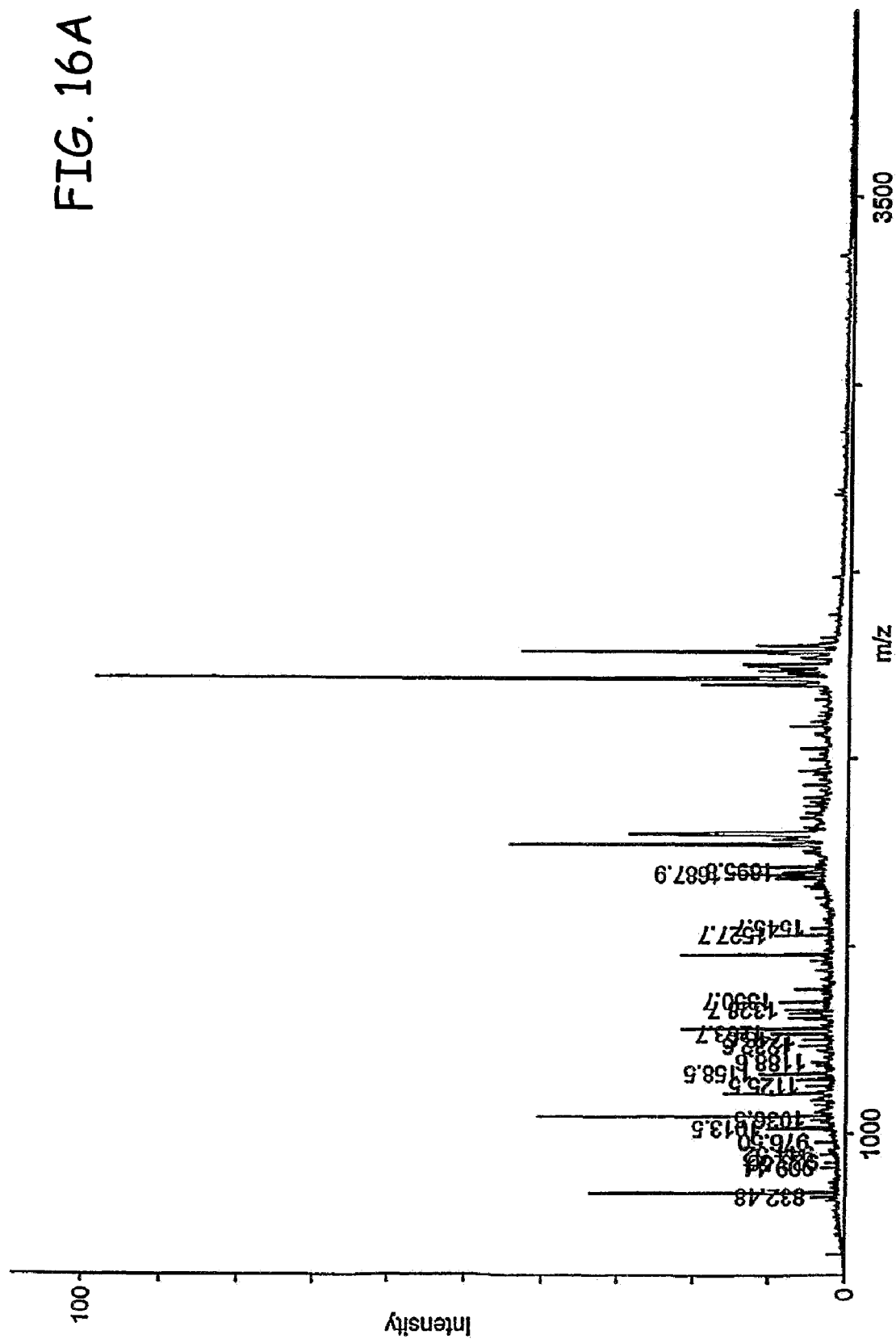
FIG. 16A is a total mass spectrometric graph with peak molecular weights noted in Daltons for NEPHGE protein N 403 prepared from tryptic peptide fragments.
Figure 16B:
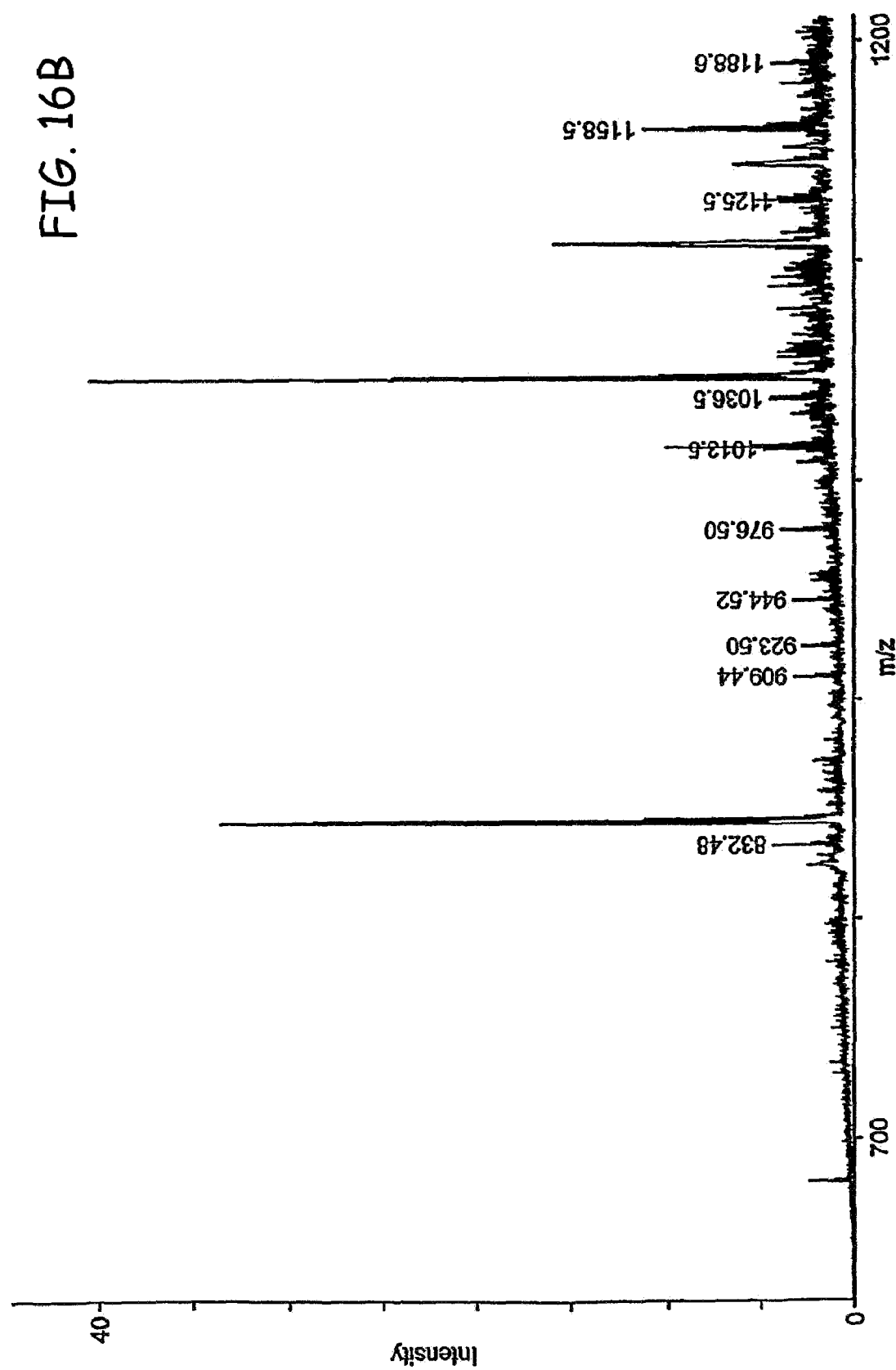
FIGS. 16B-16C represent enlarged regions of FIG. 16A for protein N 403 such that particular peaks may be readily identified.
Figure 16C:
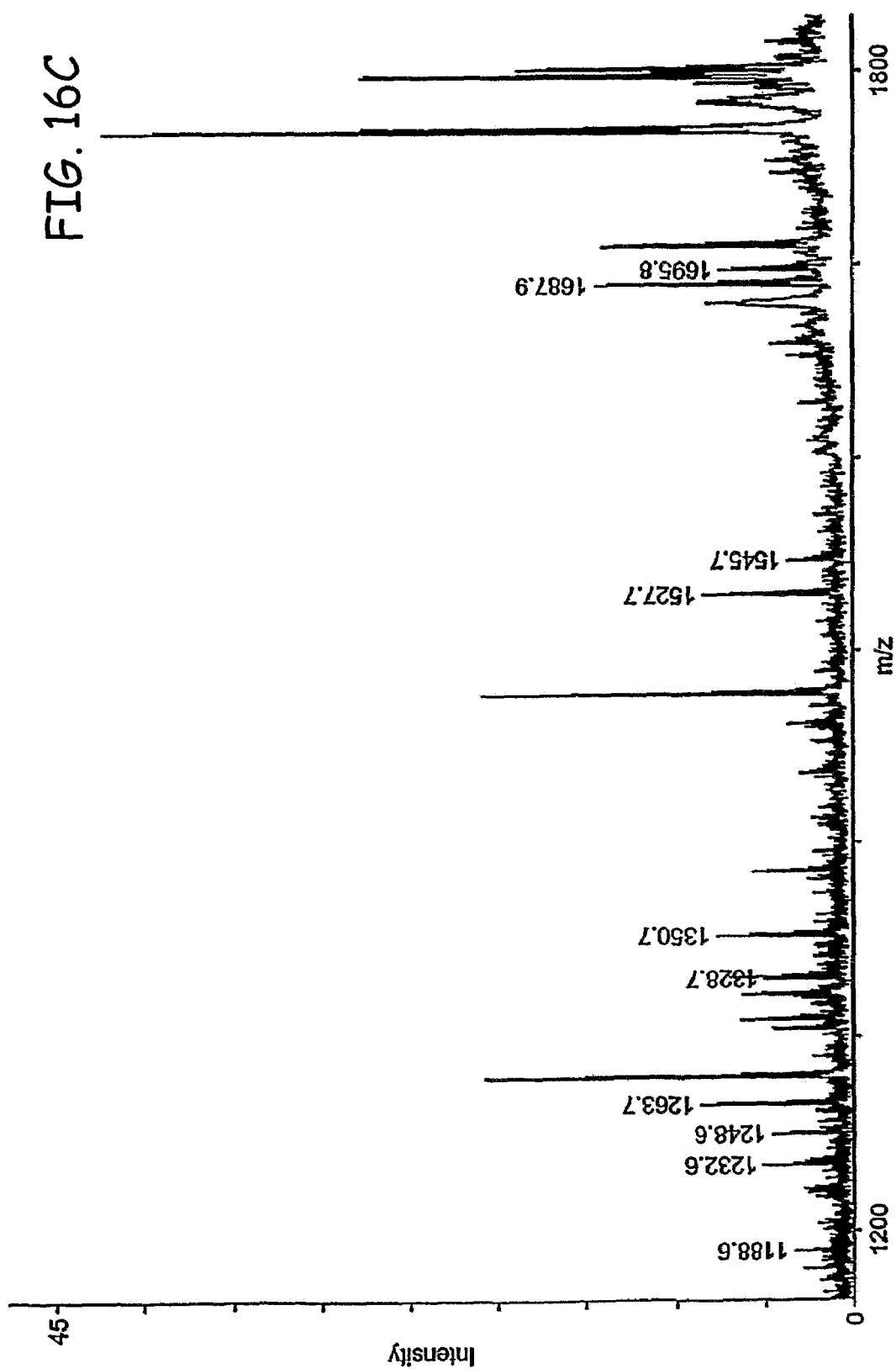
Figure 17A:
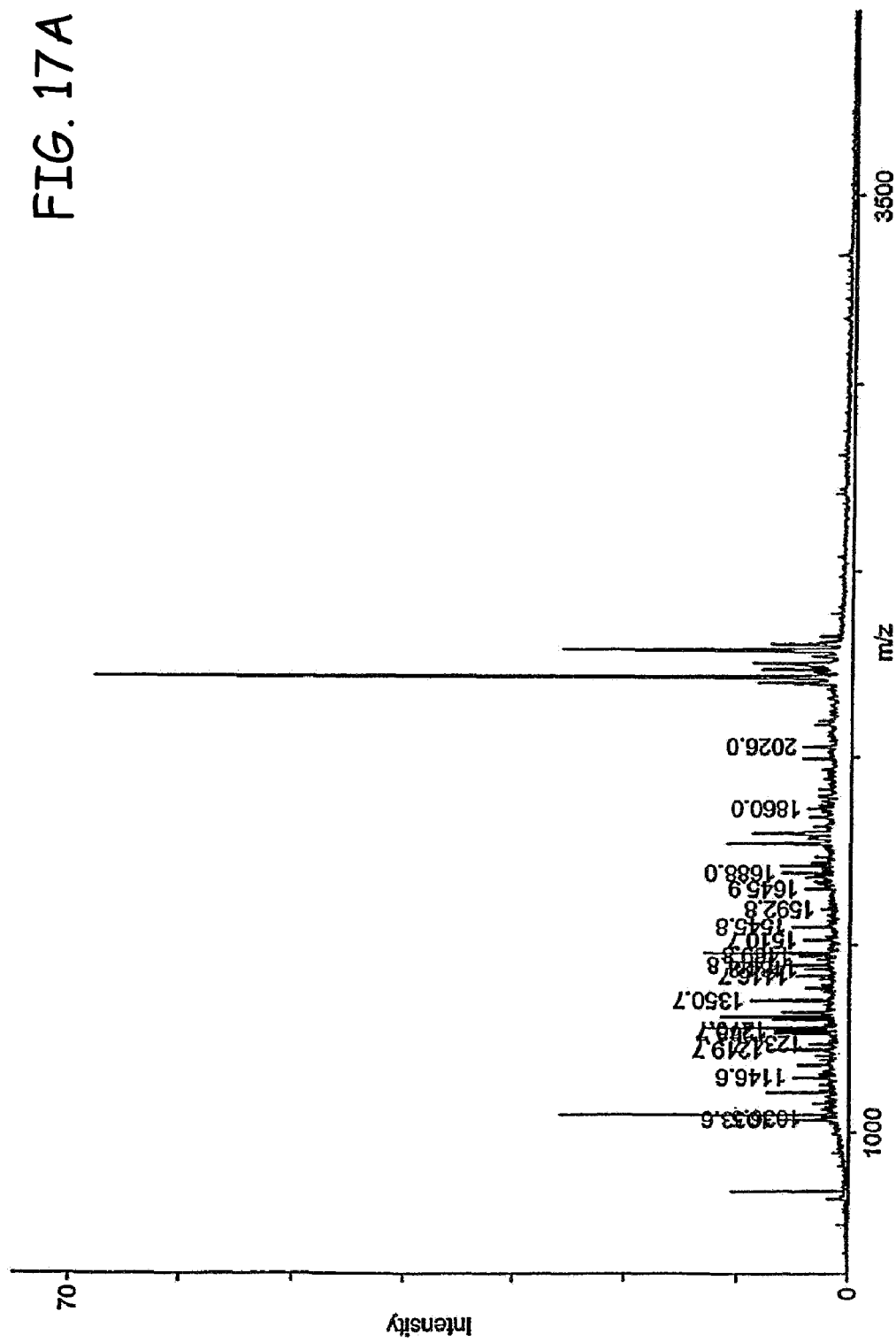
FIG. 17A is a total mass spectrometric graph with peak molecular weights noted in Daltons for NEPHGE protein N 435 prepared from tryptic peptide fragments.
Figure 17B:
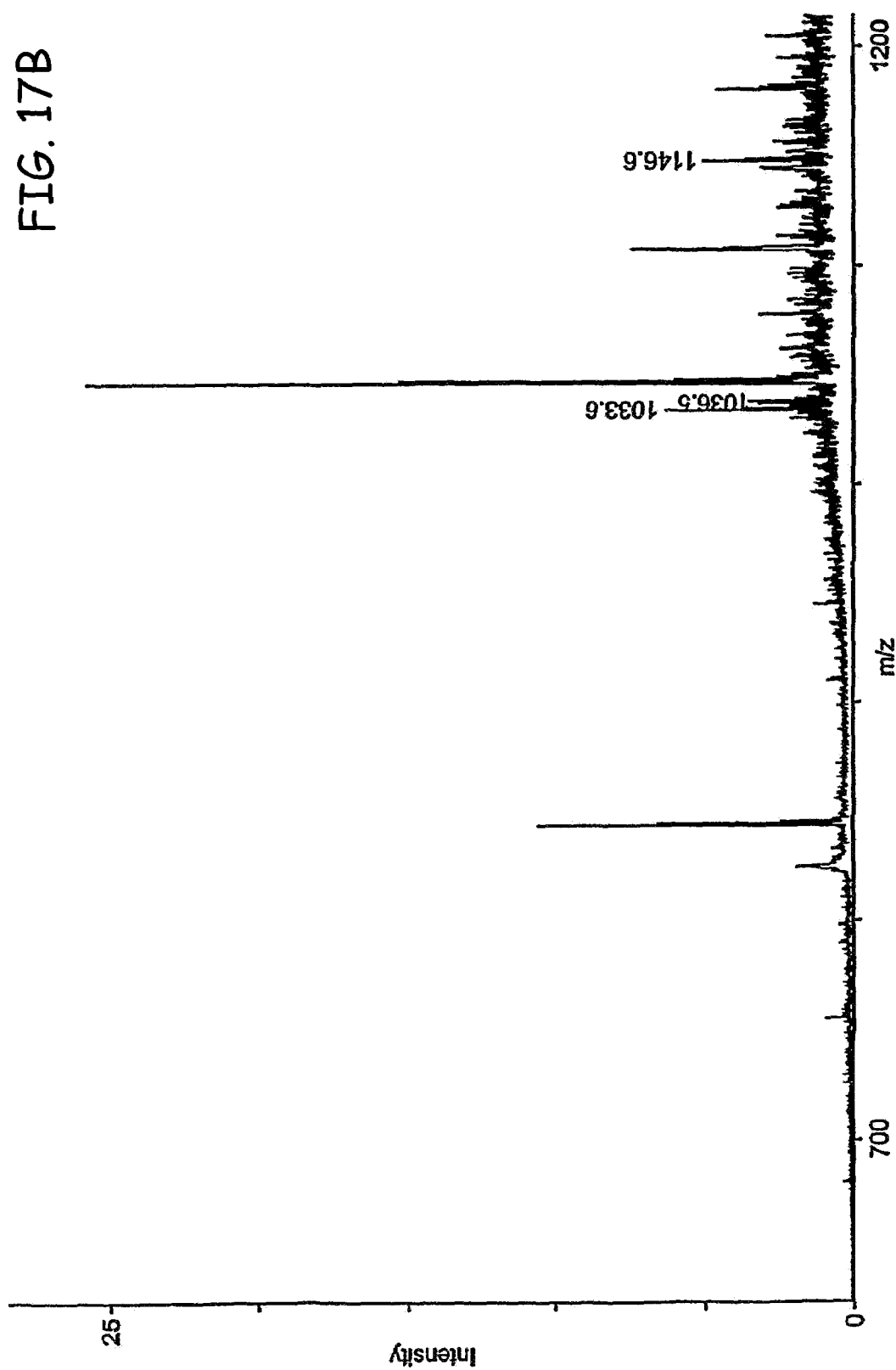
FIGS. 17B-17C represent enlarged regions of FIG. 17A for protein N 435 such that particular peaks may be readily identified.
Figure 17C:
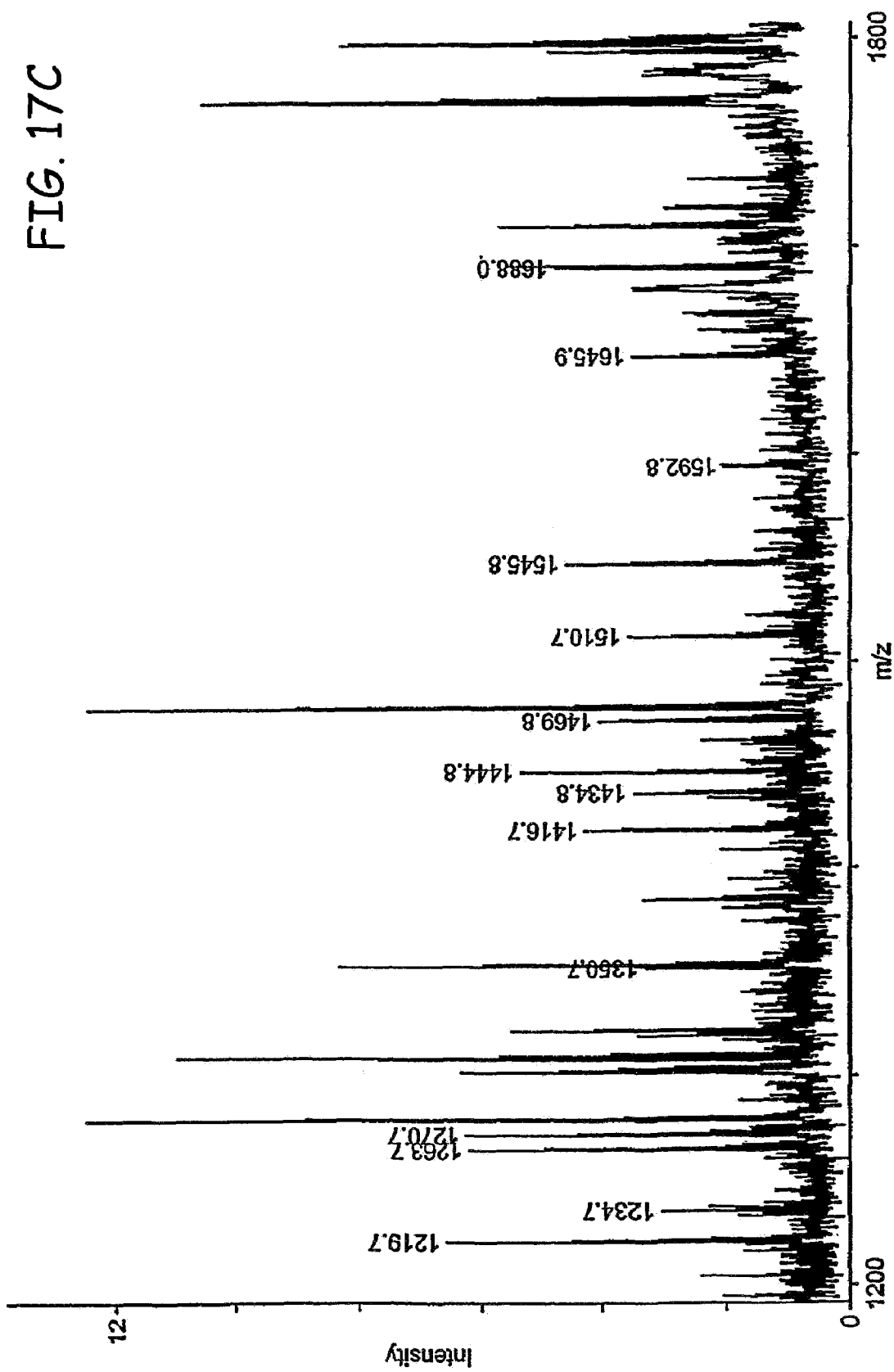
Figure 18A:
FIG. 18A is a total mass spectrometric graph with peak molecular weights noted in Daltons for NEPHGE protein N 509 prepared from tryptic peptide fragments.
Figure 18B:
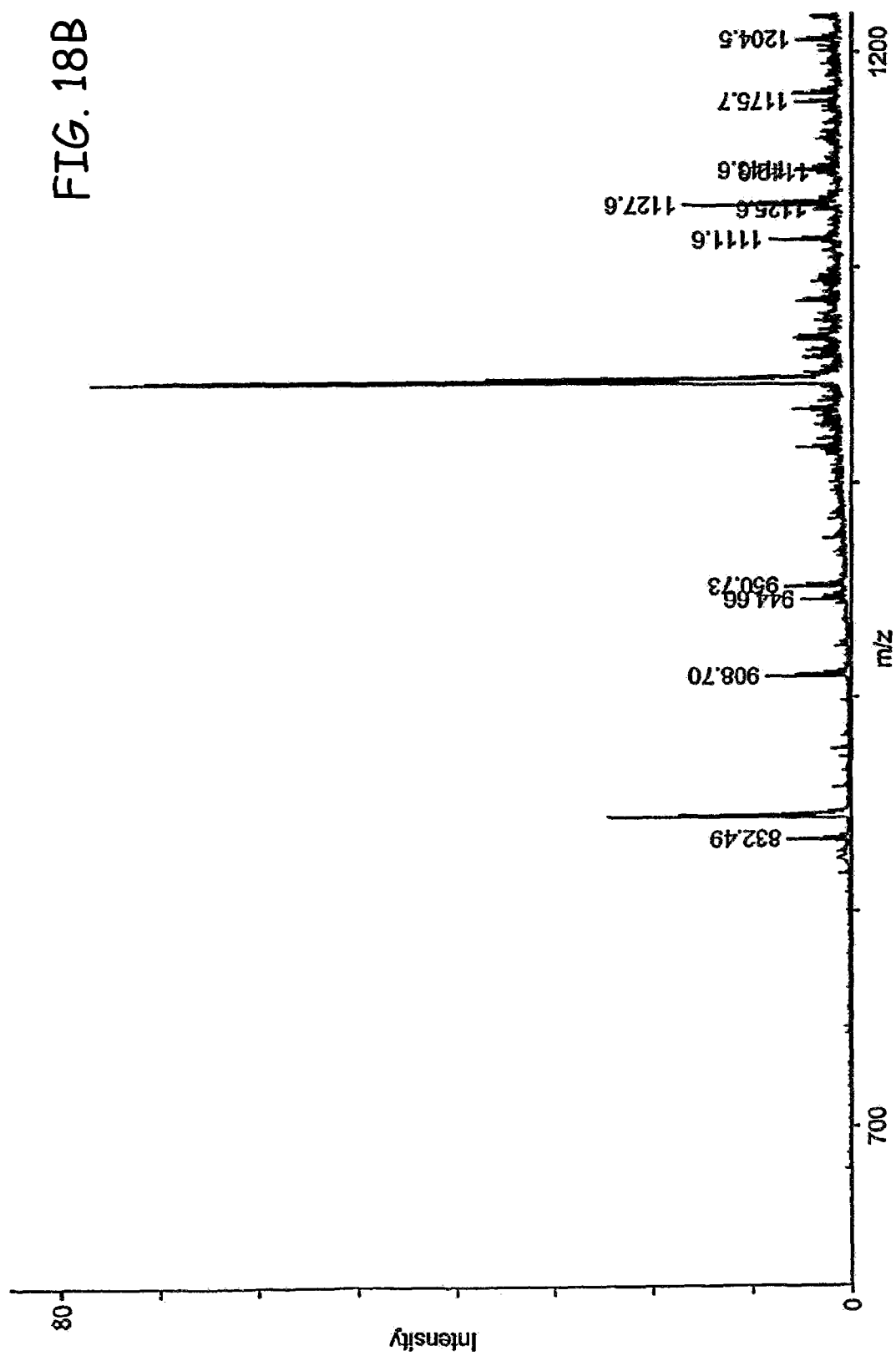
FIGS. 18B-18C represent enlarged regions of FIG. 18A for protein N 509 such that particular peaks may be readily identified.
Figure 18C:
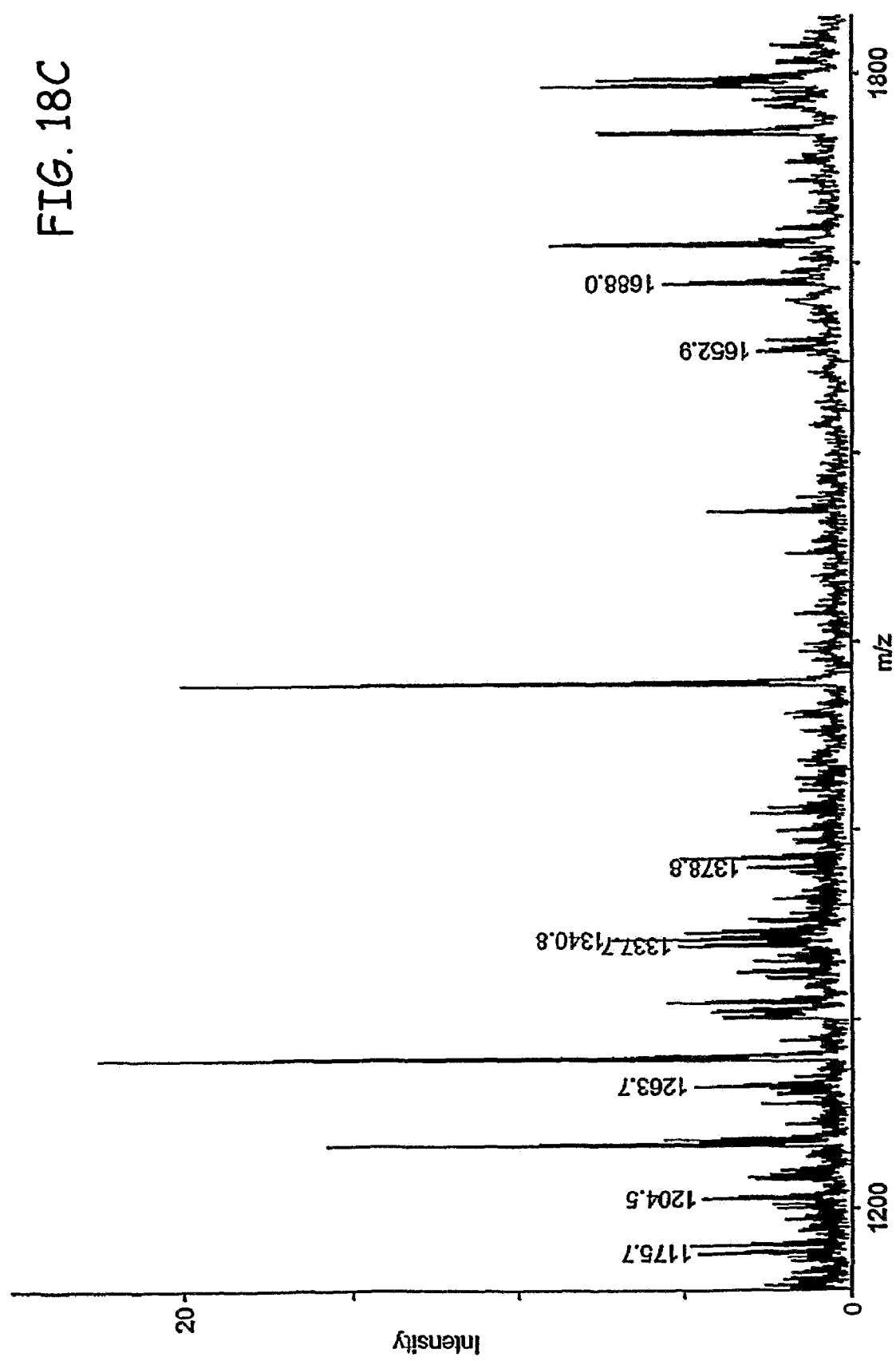
Figure 19A:
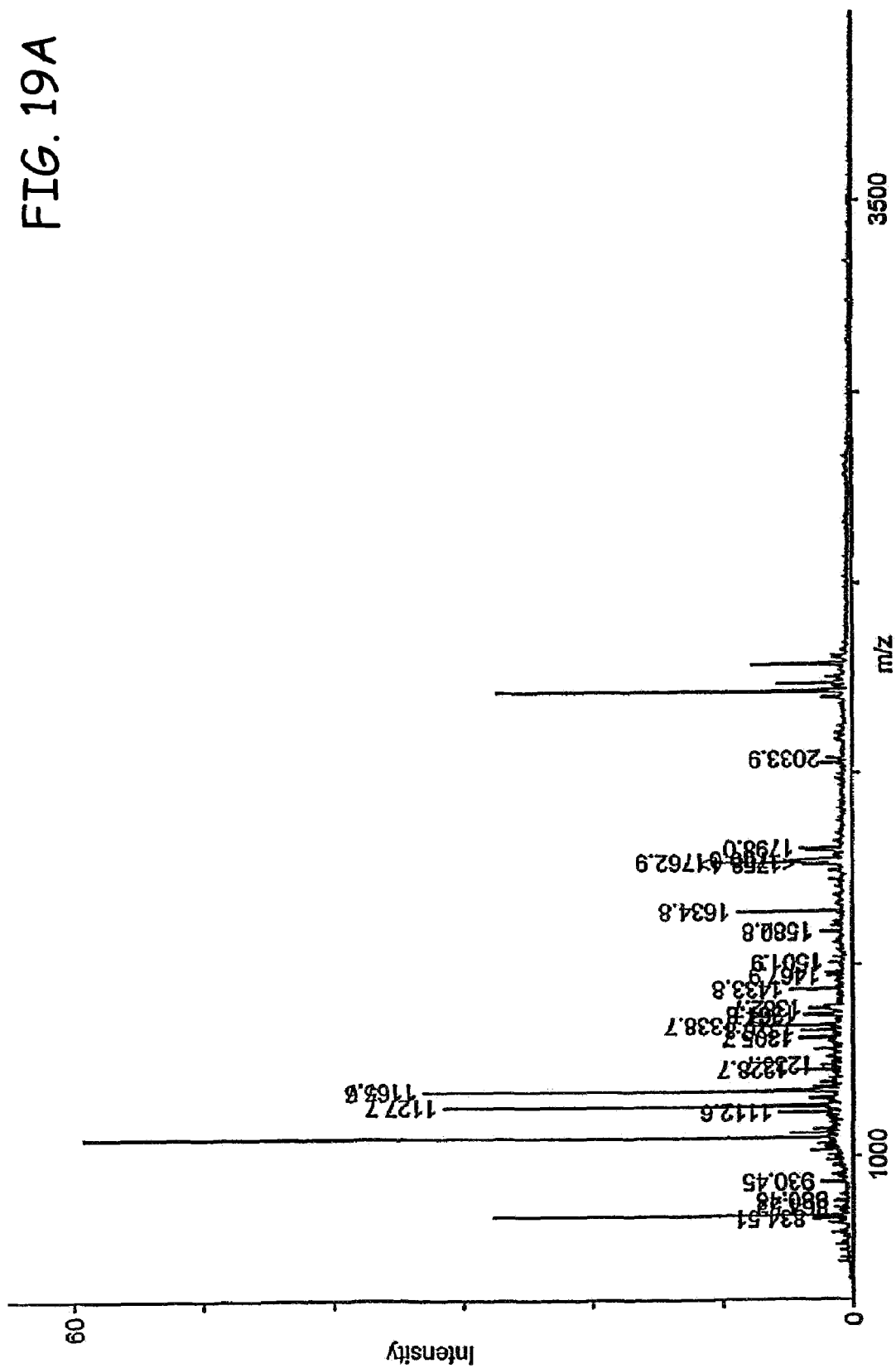
FIG. 19A is a total mass spectrometric graph with peak molecular weights noted in Daltons for NEPHGE protein N 1355 prepared from tryptic peptide fragments.
Figure 19B:
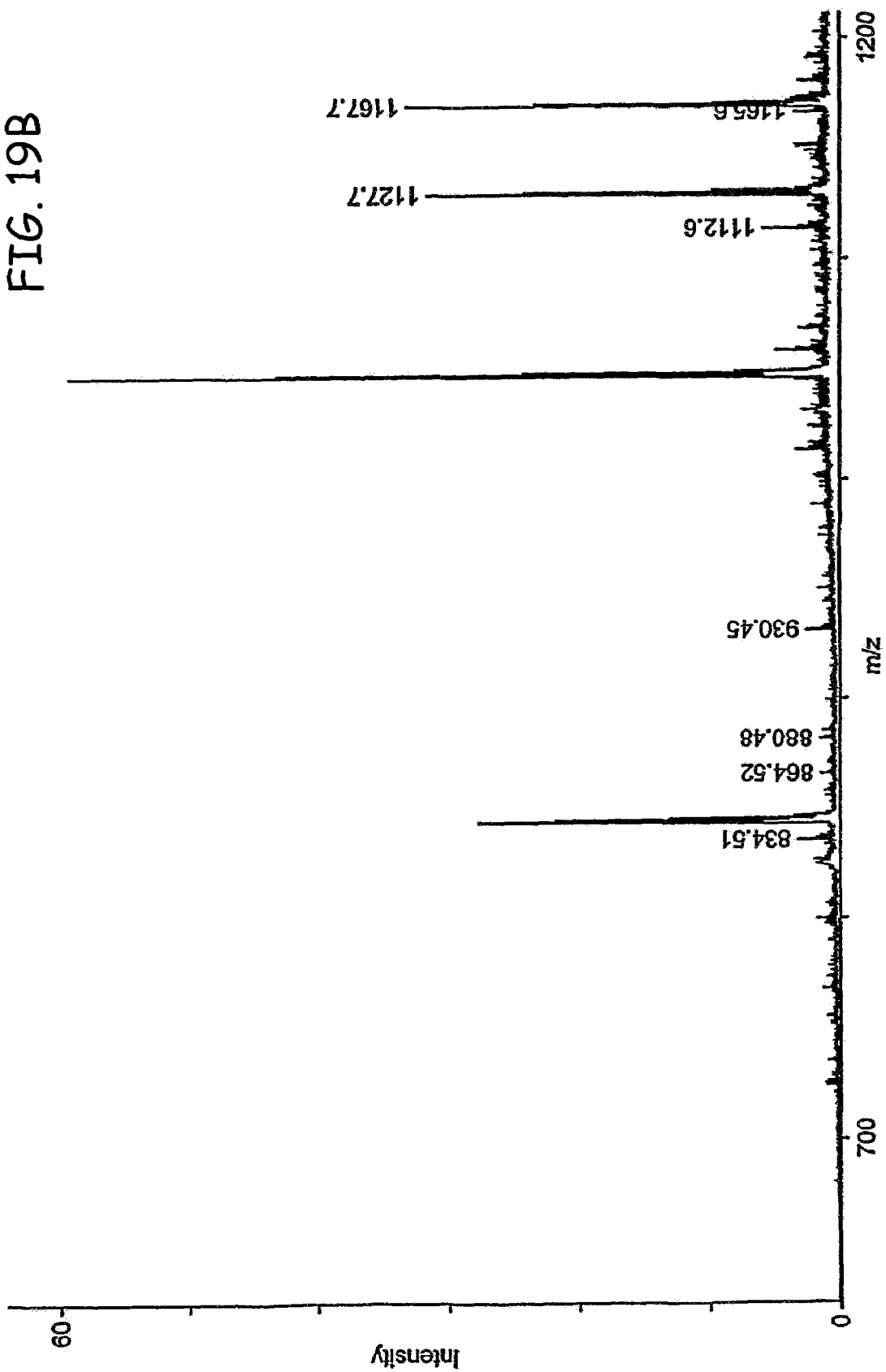
FIGS. 19B-19D represent enlarged regions of FIG. 19A for protein N 1355 such that particular peaks may be readily identified.
Figure 19C:
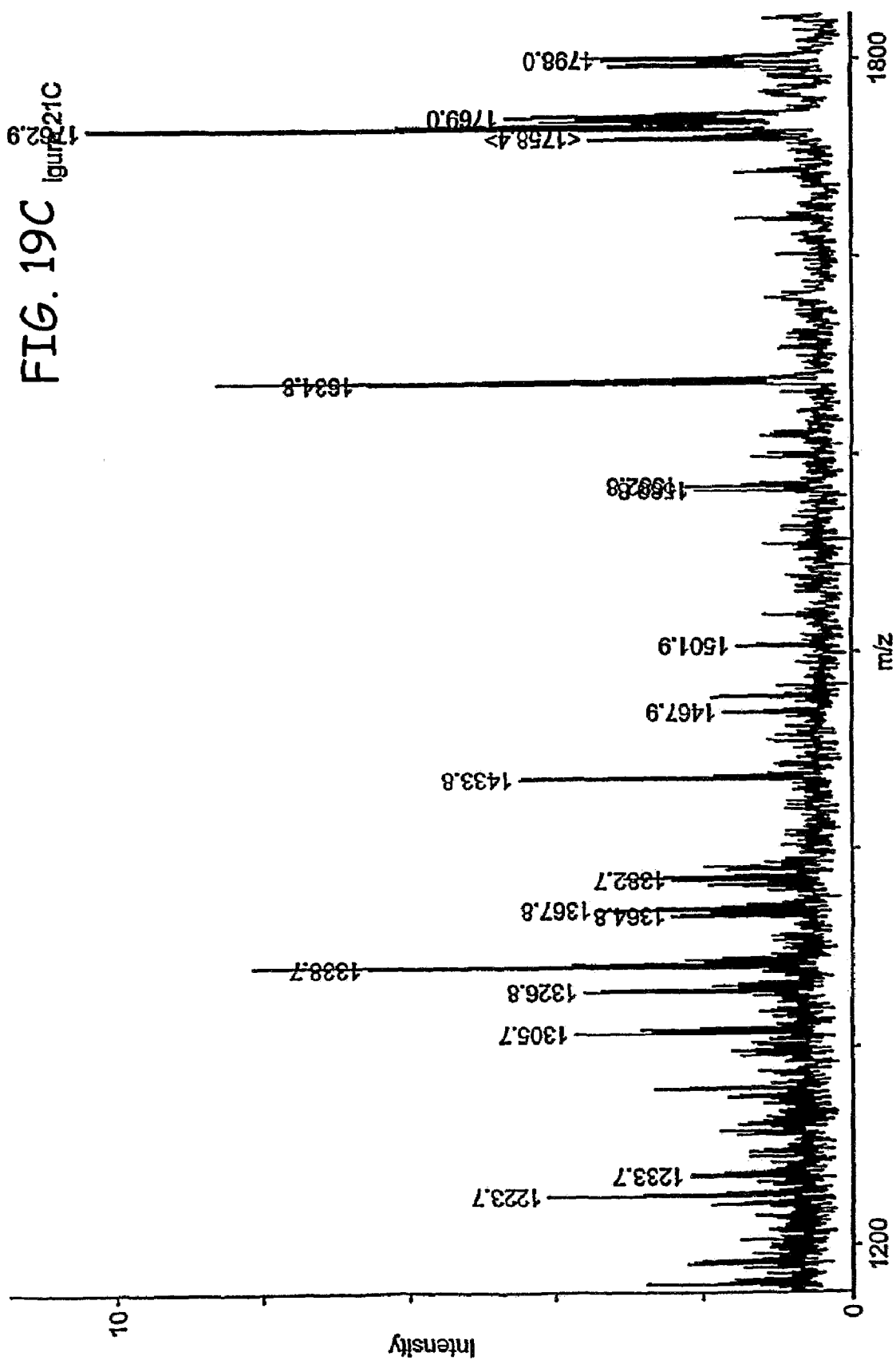
Figure 19D:
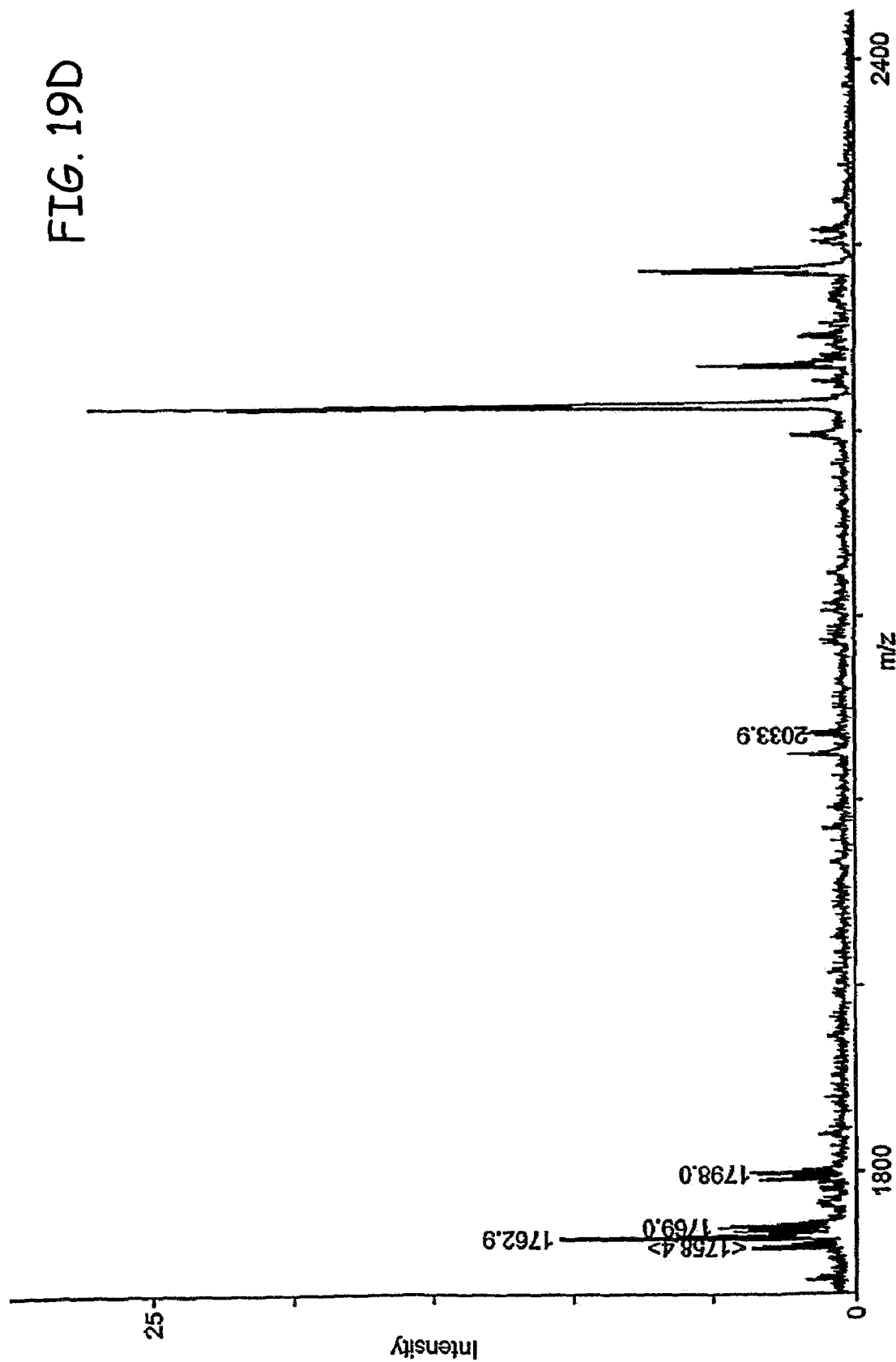

The present invention relates in a first aspect to the novel proteins identified by proteome analysis and mass spectrometry.

A further aspect relates to the use of novel proteins and proteins of table 1 or table 2 or the tables of the mass spectra MWts for the previously unidentified proteins as markers or indicators for diabetes as well as to the use of known proteins whose presence, absence or prevalence has previously not been associated with diabetes. The changes in protein expression and patterns of protein expression are considered to be important markers for diagnosis, prognosis and therapeutic applications and targets.

To identify diabetes marker proteins, IL-1β induced protein changes in BB-DP islets from neonatal BB-DP rats islets were investigated by incubating BB-DP rats islets for 24 hours with or without recombinant human IL-1β. The medium was sampled for nitrite and insulin measurements [13]. Two dimensional gel analysis of the islets was performed and fluorographs of the islets were computer analysed. Protein spots that significantly changed expression level after exposure to IL-1β were cut out of preparatory gels and attempted identified by mass spectrometry.

Proteome analysis, by 2-dimensional gel electrophoresis, mass spectrometry and bio-informatics, offered the opportunity to identify different pathways involved in IL-1β induced 1β-cell destruction. Significantly changed proteins in BB-DP rat islets after IL-1β exposure was obtained.

Similar result were obtained from WF rat islets exposed to IL-1β where 60 protein spots were identified out of 105 significantly changed protein spots. These 60 identifications correspond to 57 different proteins. Comparing the identified proteins in the BB-DP rat with the identified proteins in the WF rat, 13 proteins were identical (NEPHGE (N) 223, 231, 370, 146, 381 (3 spots), IEF (I) 1127, 955, 552, 138 (3 spots), 1136, 8580, 68, 62).

Interestingly, fewer protein spot changed expression levels upon IL-1β exposure in the BB-DP islets (82 spots) compared to WF islets (105 spots). Parts of the difference could be explained by difference in concentration of acrylamide in second dimension gels (Wistar islets were run on 10 and 15% gels whereas BB-DP islets were run on 12.5% acrylamide gels). 33 proteins were changed only in BB-DP islet responses to IL-1β in vitro and 44 proteins "specific" for WF rat islets, although many reflect similar pathways and functions in the two strains studied.

The cytotoxic effect of cytokines on islets is inhibited by inhibitors of protein synthesis indicating that β-cell destruction, is an active intracellular process requiring de novo synthesis of proteins. The protein INOS has previously been reported to change expression level after IL-1β exposure. Heat shock protein 70, 90 and MnSOD others are has been referred to oxidative stress-proteins in connection to their protective response. The proteins of the invention are involved in a variety of different pathways involved in β-cell destruction and may be classified according to the pathway. The proteins of the invention may a) be involved in energy transduction and redox potentials and glycolytic enzymes (14 proteins); b) be involved in purine/pyrimidine synthesis, DNA/RNA synthesis, RNA processing, amino add metabolism and protein synthesis (7 proteins); c) act as chaperones (5 proteins); d) be involved in differentiation, apoptosis, regulation and signal transduction; e) be involved in cellular defence; f) be involved in cellular structure; g) be involved in hormone/neurotransmitter metabolism; h) or have other functions.

A. Energy Transduction and Redox Potentials and Glycolytic Enzymes (14 Different Proteins)

The following proteins of the invention are involved in energy transduction and redox potentials and glycolytic enzymes (14 different proteins):

Malate dehydrogenase precursor;

Aconitate hydratase;

Glyceraldehyde-3-phosphate dehydrogenase;

Pyruvate kinase M2 isozyme;

Isocitrate dehydrogenase;

Glucose-6-phosphate dehydrogenase;

ATP synthase;

ATP synthase alpha chain;

L-3-hydroxy-CoA dehydrogenase precursor;

NADH dehydrogenase;

Carbonyl reductase;

Vacuolar ATP synthase subunit B;

Alcohol dehydrogenase; and

Creatine kinase B chain was identified together with cytokeratine 8 polypeptide are each diabetes marker proteins of the present invention.

IL-1β induces NO production in the 1β-cells which in turn nitrosylates the Fe—S complex in enzymes [31] and inactivates mitochondrial aconitase [32] whereby the oxidation of glucose in the Krebs Cycle is inhibited which results in decreased ATP production.

The malate dehydrogenase precursor has been found down-regulated in three spots, Aconitate hydratase, glyceralaldehyde-3-phosphate dehydrogenase, pyruvate kinase M2 isozyme and isocitrate dehydrogenase precursor are all down-regulated and involved in energy production in the Krebs Cycle.

Glucose-6-phosphate dehydrogenase, the first step in the pentose phosphate pathway is up-regulated, which could be to compensate for the decreased energy production through the Krebs Cycle.

Furthermore several proteins involved in energy transduction and redox potentials are down-regulated in response to IL-1β exposure. The proteins are H+ transporting ATP synthase, ATP synthase alpha chain, L-3-hydroxy-CoA dehydrogenase precursor, NADH dehydrogenase, carbonyl reductase, vacuolar ATP synthase subunit B and alcohol dehydrogenase.

Taken together this strongly suggest that energy production in islets is inhibited by IL-1β in BB-DP rat islets.

Creatine kinase B chain was identified together with cytokeratine 8 polypeptide in an up-regulated spot. Creatine kinase was found down-regulated in WF islets [7]indicating that creatine kinase-could also be involved here.

B. Purine/Pyrimidine Synthesis, DNA/RNA Synthesis, RNA Processing, Amino acid Metabolism and Protein Synthesis (8 Proteins)

The following proteins of the invention are involved in purine/pyrimidine synthesis, DNA/RNA synthesis, RNA processing, or amino acid metabolism and protein synthesis (8 different proteins:

5-aminoimidazole-4-carboxamide ribonucleotide formyltranferase;

UMP-CMP kinase;

Adenine phosphoribosyltransferase;

Heterogeneous nuclear ribonucleoprotein A2/1311;

Heterogeneous nuclear ribonucleoprotein M (M4 protein deletion mutant);

Aspartate aminotransferase (cytosolic);

Aspartate aminotransferase (mitochondrial); and

Ribosomal protein L11 are each further diabetes marker proteins of the present invention.

Three of the identified proteins, 5-aminoimidazole-4-carboxamide ribonucleotide formyltranferase, UMP-CMP kinase and adenine phosphoribosyltransferase, involved in the synthesis of purine and pyrimidine, were down-regulated after exposure to IL-1β.

Heterogeneous nuclear ribonucleoprotein A2/1311 and M4 protein deletion mutant (heterogeneous nuclear ribonucleoprotein M) are both involved in processing of pre-RNA [33, 34] and were both down-regulated too. Aspartate aminotransferase, both the cytosolic and the mitochondrial form, involved in amino add metabolism were down-regulated after exposure to IL-1β. The down-regulation of all these proteins support that the β-cells focus their efforts in protecting themselves against the deleterious effects of IL-1β and down-regulate functions that are not involved in protection.

C. Chaperones (7 Different Proteins)

Endoplasmin;

GRP 78 [39] 78 kDa glucose regulated protein (GRP78);

Protein disulfide isomerase;

Probable disulfide isomerase P5;

Calreticulin;

Endoplasmic reticulum protein ERP 29; and

HSP70 are each further diabetes marker proteins of the present invention.

Endoplasmin, one of two proteins in a down-regulated spot, belongs to the HSP 90 family which is involved in protein folding [38] and has been shown to have serine kinase activity which is enhanced by association with 78 kDa glucose regulated protein (GRP78) [39].

GRP78, was found in three spots, one up-regulated, one down-regulated and together with endoplasmin in one down-regulated spot (demonstrating complex differential regulation of post-anslational modifications). It is a member of the HSP 70 family involved in the folding and assembly of proteins in the endoplasmatic reticulum [40]. Endoplasmic reticulum protein ERP 29 is a member of the ER protein-processing machinery and is involved in protein secretory events. IL-1β exposure down-regulates this protein.

Protein disulfide isomerase, involved in molecular chaperone of glycoprotein biosynthesis [41]is down-regulated by IL-1β together with probable disulfide isomerase P5. Both are involved in the formation and rearrangement of disulfide bonds in proteins. Interestingly, all these proteins are able to bind calcium like calreticulin [42] and may also be involved in signal transduction.

Up-regulated HSP70 expression has been demonstrated to diminish the inhibitory effect of IL-1β on islet insulin secretion and NO-induced mitochondrial impairment [43, 44]. In the diabetes prone BB rat, insufficient HSP70 expression in islets has been correlated to sensitivity to NO. and oxygen radical toxicity [12].

D. Differentiation, Apoptosis, Regulation and Signal Transduction (7 Different Proteins)

Galectin-3;

Eukaryotic initiation factor 4A;

Toad 64;

Secretagogin;

Calreticulin;

Craniofacial development protein 1; and

The Voltage dependent anion channel protein are each further diabetes marker proteins of the present invention.

IL-1β induces cell death through different pathways, among them gene controlled apoptosis [45-47]. Galectin-3, a protein involved in cell survival by inhibiting apoptosis [48-50] is up-regulated and present in 2 spots.

Eukaryotic initiation factor 4A, like NUK 34, is involved in transcriptional/translational regulation [51] is up-regulated indicating specific activation of protein synthesis.

Toad 64, a protein up-regulated over the course of neurogenesis and playing a role in signal transduction processes involved in axon growing [52]is up-regulated after IL-1β exposure.

The calcium binding protein, calreticulin, found up-regulated in two spots, can act as an important modulator of the regulation of gene transcription by nuclear hormone receptors (glucocorticoid and androgen receptors) [55] [56]. Taken together the changes in expression level of these proteins indicate that proteins potentially involved in apoptosis is changed by IL-1β exposure.

Another calcium binding protein, secretagogin, specific for neuroendocrine cells and related to calbindin D-28k, is involved in cell growth and maturation [53] and is down-regulated. Calbindin D-28k has been shown to be involved in protection from cytokine induced apoptosis in 13-β cells [54].

Voltage dependent anion channel is identified in a down-regulated spot together with L-3-hydroxyacyl-CoA dehydrogenase precursor. The Voltage dependent anion channel protein is able to form small pores in the outer mitochondrial membrane allowing movements of adenine nucleotides. Bcl2 proteins binds to the channel in order to regulate the mitochondrial membrane potential and release of cytochrome c during apoptosis [57].

E. Cellular Defence (2 Proteins)

Catalase; and

Glutathione synthetase are each further diabetes marker proteins of the present invention.

Free radicals (e.g. nitric oxide and hydrogen peroxide) are proposed to play a central role in the destruction of β-cells [3]. Catalase, which serves to protect cells from the toxic effects of hydrogen peroxide, is up-regulated in response to IL-1β exposure.

Overexpression of catalase, super oxide dismutase and glutathione peroxidase in Rinm5F cells protect against the toxicity of NO donors [58]. The increased expression of catalase in the BB-DP islets apparently is not sufficient to protect against the IL-1β induced free radicals. Hereditary catalase deficiencies are reported to increase the risk for T1DM in a Hungarian population [59].

Glutathione synthetase is important for a variety of biologic functions including protection of cells from oxidative damage by free radicals and detoxifications [58, 60 and 61] and is here reduced to one eighth of the normal concentration (down-regulated) suggesting a reduced potential for cellular defence against oxygen-derived free radicals.

F. Cellular Sure (3 Proteins)

Tubulin beta-5 chain;

Cytokeratin 8; and

Keratin 2a are each further diabetes marker proteins of the present invention.

Tubulin beta-5 chain, the major constituent of microtubules were present in 4 spots, possibly 4 different modifications, all down-regulated probably due to lower mitotic rate upon IL-1β exposure. Cytokeratin 8 was present in the same upregulated spot as creatine kinase-B. Cytokeratin 8 has been shown to play an essential role in regulation of growth and differentiation in the exocrine pancreas [62]. Furthermore keratin 2a is found together with tubulin beta-5 chain in a down-regulated spot.

G. Hormone/Neurotransmitter Metabolism (5 Different Proteins)

Membrane associated progesterone component (25-Dx);

Amyloid beta-peptide binding protein;

Neuroendocrine convertase 1;

Neuroendocrine convertase 2; and

Beta-alanine oxoglutarate aminotransferase (GABA-transaminase)

are each further diabetes marker proteins of the present invention.

Membrane associated progesterone component (25-Dx) is a receptor for progesterone which is massively down-regulated after IL-1β exposure. 25-Dx has 71% sequence homology with the transmembrane domain of the precursor for the IL-6 receptor and a conserved consensus sequence found in the cytokine/growth factor prolactin receptor superfamily [63].

Amyloid beta-peptide binding protein is involved in androgen metabolism and has been postulated to be involved in apoptosis and amyloid toxicity [64]. Here, it is down-regulated by IL-1β.

Beta-alanine oxoglutarate aminotransferase (GABA-transaminase) is responsible for the catabolism of the inhibitory neurotransmitter gamma-aminobutyric add (GABA) and is down-regulated in IL-β exposed islets. It probably has a different function in the β-cells.

H. Other Functions (2 Proteins)

5-aminolevulinate synthase precursor, and the cytomegalovirus protein immediate-early protein 1 are each further diabetes marker proteins of the present invention 5-aminolevulinate synthase precursor is a rate limiting nuclear-encoded mitchondrial enzyme in the heme biosynthetic pathway which serve as part of several heme containing proteins such as hemoglobin and catalase. IL-1β down-regulates the expression of 5-aminolevulinate synthase precursor and might then increase the β-cell susceptibility to IL-1β due to reduced levels of one of the substrates for catalase production.

Interestingly the cytomegalovirus protein immediate-early protein 1 has been identified in the BB-DP islets as down-regulated. This protein is able to transactivate heterologous promoters [65] in rat cytomegalovirus. The protein may come from a cytomegalovirus infection or may be a homologous rat protein.

Exposure of BB-DP rat islets of Langerhans to 150 pg/ml of human IL-1β for 24 hours induces significant changes in expression levels of 82 proteins. Positive protein identification has been obtained for most spots by mass spectrometry, which at present is the most powerful method and technique of choice to identify proteins from high resolution two-dimensional gels [66]. It is understood by the person skilled in the art that the effect of human IL-1β on rat islets is the same effect as that anticipated on human islets.

In Table 1, proteins common for BB-DP and WF are marked with #. From Table 1 it is evident that proteins involved in chaperoning, protein folding and translocation and proteins involved in energy transduction and redox potentials are common pathways affected in the two strains. For both groups most of the proteins are down regulated suggesting that similar mechanisms are affected by IL-1β exposure in the two rat strains. Another pattern is seen for the glycolytic enzymes. Here the outcome of the changes in expression levels of proteins, a lower energy production, although them is only overlap in 2 out of 8 proteins in the BB-DP rat [7]. This suggests that IL-1β affects the glycolytic enzymes differently in the two rat strains with the same final result, a lower energy production.

Two proteins involved in cellular defense, catalase and glutathione synthetase are both changed in expression levels by IL-1β in BB-DP rats but not in WF rat islets. The increased expression of catalase protects cells against the free radical hydrogen peroxide indicating that free radicals are present in the BB-DP islets after IL-1β exposure and that the islets are trying to protect themselves against the free radicals. The previously described strain differences in rat islets regarding IL-1β sensitivity and NO. production after IL-1β exposure might be explained by dent abilities to mount a free radical defense [10].

The other protein involved in cellular defense, glutathione synthetase involved in energy requiring synthesis (ATP is one of the substrates) of the free radical scavenger glutathione is decreased by more then seven fold. This indicates that the glutathione detoxifying pathway is impaired by IL-1β in BB-DP rats.

In the functional studies of the islets in vitro, IL-1β increased the NO. production over a 24 hour period, but INOS was not identified as one of the up-regulated proteins. This could be explained by absence of IL-β in the 4 hours labeling period after the IL-1β incubation or that the difference in expression level does not fulfil our criteria for significant difference or is not present in the gels. The same was seen in WF islets incubated with IL-1β [7]. Increased mRNA levels for INOS has been found in prediabetic NOD mice [67].

Taken together, the comparison of IL-1β exposed neonatal BB-DP islets and WF islets has revealed that IL-β induce significant changes in the expression level of, respectively, 82 and 105 protein spots. There is an overlap in 13 of the identified proteins, and involvement of the same pathways, suggesting that different proteins are expressed upon IL-1β exposure in BB-DP and WF rat islets although there is no difference in NO. and insulin and that the final result, apoptosis and β-cell destruction is the same.

Some proteins are seen in more than one spot, e.g. calreticulin and GRP 78, which indicate that the protein is present in more than one form presumably due to post-translational modifications. Post-translational modifications, such as phosphorylations, methylations or glycosylations are important for the function or activation of the protein. Proteins with known genes and chromosomal localisation close to known T1 DM loci in the human genome might be of particular interest and might identify primary changes.

A first aspect of the invention relates to marker proteins. The marker proteins are selected from the group consisting of:

a) a protein of table 1, a protein of table 2, a protein of table 3, a protein of FIG. 1 (such as a protein marked with a number) and a protein having a spectrum as shown in any one of the FIGS. 3A-19D; and b) a protein with at least 80% sequence homology with a protein in a).

Also, the marker protein can be selected from the group consisting of:

a) one or more proteins present in a significantly lower or significantly higher amount on a polyacrylamide gel of proteins from said biological sample in relation to a control;

b) one or more proteins present on a polyacrylamide gel of proteins from said biological sample and absent on polyacrylamide gel of proteins of a control; and c) one or more proteins absent on a polyacrylamide gel of proteins from said biological sample and present on polyacrylamide gel of proteins of a control.

The meaning of the term "control" is evident for a person skilled in the art of proteomics. Preferably, the control is an IOD % value of a spot (having the same position) from a gel of proteins from a sample originating from a human who is not predisposed for or having diabetes.

The term "marker protein" is meant to encompass the above mentioned proteins, as well as similar proteins from other species of mammals. The human forms of the proteins are of particular interest. For example, it is suggested that the human forms of the rat proteins can be used as markers for diabetes in human beings. Thus, the term "marker protein" encompasses the human form of the identified proteins in table 1 and the not yet identified proteins in table 2, as well as the proteins being up- or down-regulated in a mammalian tissue sample (e.g. human) as described elsewhere. Examples of the marker proteins of the invention are given below.

An other aspect of the invention relates a method for diagnosing or for determining the predisposition of diabetes in a mammal, e.g. in a human, the method comprising determining the presence, absence or level of expression of at least one marker protein in a biological sample from said mammal. The biological sample can be selected from the group consisting of urine, blood, saliva, lymphatic fluids, and tissue, presently pancreatic tissue is preferred.

A presently preferred method comprises establishing the increased expression of at least one marker protein (an up-regulated marker protein) selected from the group consisting of:

a) a protein which is defined in table 1 and/or 2, and marked as up-regulated; and b) a protein which is a modification or a derivative of a protein in a), so as to have at least 80% sequence homology with a protein in a), but of course the invention also relates to a method establishing the decreased expression of at least one down-regulated marker protein.

In another embodiment, the invention relates to a method for determining the predisposition for diabetes in a human, the method comprising:

a) determining the increased expression of at least one marker protein in a biological sample originating from the human, said marker protein being selected from the group consisting of: I) an up regulated protein defined in table 1, 2 and/or 3, and II) a protein which is a modification or a derivative of a protein in I), so as to have at least 80% sequence homology with a protein in I);

b) determining the decreased expression in a biological sample from the human of at least one marker protein, said marker protein being selected from the group consisting of: I) a down-regulated protein defined in table 1, 2 and/or 3 and II) a protein which is a modification or a derivative of a protein in I), so as to have at least 80% sequence homology with a protein in I); or c) combinations of the determinations in a) and b).

Thus, the determination of whether a protein is up-regulated or down-regulated serves as useful indicators of diabetes susceptibility. The pattern of up and down regulation may also serve as an indicator. That is to say that the level of expression of more than one protein is established and the pattern of expression of a grouping of proteins is used as an indicator.

In a suitably embodiment, at least one marker protein is selected from the group consisting of one or more proteins present in a significantly lower or significantly higher amount on a polyacrylamide gel of proteins from said biological sample in relation to a control, one or more proteins present on a polyacrylamide gel of proteins from said biological sample and absent on polyacrylamide gel of proteins of a control, one or more proteins absent on a polyacrylamide gel of proteins from said biological sample and present on polyacrylamide gel of proteins of a control.

In another embodiment, the invention relates to a method of treating diabetes, or preventing or delaying the onset or of diabetes, in a mammal, e.g. in a human, comprising altering the expressing of a least one marker protein.

The method preferably comprises administering a compound selected from the group consisting of:

a) a protein which is defined in table 1, 2 and/or 3;

b) a protein which is a modification or a derivative of a protein of table 1, 2 or 3, so as to have at least 80% sequence homology with a protein of table 1, 2 or 3;

c) a protein having the same function as a protein in a) and/or b);

d) a nucleotide sequence coding for a protein in a), b) or c);

e) an antibody for a protein of a), b) or c);

f) a nucleic add fragment capable of binding to a protein of a) b) or c); and g) a compound capable of binding to a protein of a), b) or c) to said human.

Also, the invention relates to the use of such a compound for the manufacture of a medicament for the treatment or prophylaxis of diabetes. The term "diabetes" comprises diseases associated with diabetes, especially with type 1 diabetes mellitus.

With regard to a method of treating diabetes, a single protein may be targeted for therapy or a grouping of proteins may be targeted. The level of expression of these targeted proteins may be altered or the proteins themselves may be interfered with in order to alter their activity. Thus, an interesting embodiment of a method of treating diabetes in a human comprises altering the expressing of a marker protein.

In another embodiment, the invention relates to a method of determining the likelihood of an agent having a therapeutic effect in the treatment of diabetes comprising determining the relative level of expression of one or more marker proteins before and after exposing a test model to said agent.

Also, the invention relates to a method of determining the effect of a compound in the treatment of diabetes comprising determining the level of expression of proteins of one or more marker proteins.

In a further embodiment, the invention relates to a method of determining the level of effect of a compound used in the treatment of diabetes comprising determining the level of expression of one or more marker proteins before and after exposing a test model to said agent.

Also, the invention relates to a method of determining the nature or cause of diabetes in a mammal, e.g. in a human, having or susceptible to said disease comprising establishing the level of expression of a at least one marker protein in relation to a model.

An other embodiment of the invention relates to a nucleic add fragment comprising a nucleotide sequence which codes for a marker protein, or to a nucleic add fragment which hybridizes with a such a nucleic add fragment or a part thereof or with its complementary strand.

The invention relates to the use of the above mentioned nucleic add fragments for detecting the presence of a marker protein.

In yet another embodiment, the invention relates to an antibody able to bind to a marker protein. Such an antibody can be a polyclonal antibody or a monoclonal antibody. The invention also relates to the use of such an antibody for detecting the presence of a marker protein.

In a further embodiment, the invention relates to a test kit for diagnosing diabetes or a genetic predisposition for diabetes in a mammal, e.g. in a human, comprising:

a) a binding means which specifically binds to at least one marker protein; or which binding means is an antibody for at least one said marker protein, a nucleic add fragment capable of binding to at least one said marker protein, or a compound capable of binding to at least one said marker protein;

b) a means for detecting binding, if any, or the level of binding, of the binding means to at least one of the marker proteins or to at least one of the nucleic add fragments, and c) a means for correlating whether binding, if any, or the level of binding, to said binding means is indicative of the individual mammal having a significantly higher likelihood of having diabetes or a genetic predisposition for having diabetes.

In an other embodiment, the invention relates to a method for determining the effect of a substance, the method comprising using a mammal, e.g. a human, which has been established to be an individual having a high likelihood of having diabetes or a genetic predisposition for having diabetes by use of a method of the invention, the method comprising administering the substance to the individual and determining the effect of the substance.

The present investigators anticipate that a method of determining the nature or cause of diabetes in a human having or susceptible to said disease comprising establishing the level of expression of a protein of Table 1 in relation to a model serves for understanding the disease and potential therapies.

In the testing of compounds, knowledge about the activity or target of an agent is useful for understanding the therapeutic activity of said agent and may assist in improving the desired therapy. The developments of the present investigators allows for a method of determining the effect of a compound in the treatment of diabetes comprising determining the level of expression of one or more marker proteins and to a method of determining the level of effect or level of activity of a compound used in the treatment of diabetes comprising determining the level of expression of one or more marker proteins before and after exposing a test model to said agent.

A very important embodiment of the invention relates to a pharmaceutical composition which comprises:

a) a substance which is capable of regulating the expression of a nucleic acid fragment coding for at least part of a marker protein;

b) a marker protein;

c) a derivative, homologue or mimic of a marker protein;

d) an antibody for a marker protein;

e) a nucleic acid fragment capable of binding to a marker protein; and/or f) a compound capable of binding to a marker protein.

The pharmaceutical composition can be used as a medicament, such as for treatment or prophylaxis of diabetes.

It should be noted that the detection of any combination of more than one of the markers would be expected to make the analysis an even more reliable indicator for the disease related to diabetes. Thus, a method for diagnosing or determining the predisposition of at least one disease related to diabetes comprising determining the presence, activity, concentration and/or level of expression of a combination of two markers would be preferred and three or more markers (e.g. at least 4, 5, 6 or 7 markers) would be strongly preferred. It is analogously suggested that treatment with more than one compound (e.g. at least 2, 3, 4, 5, 6 or 7 compounds) according to the invention (e.g. more than one compound chosen from the group consisting of: a polypeptide, a nucleic add fragment or an antibody according to the invention), said compounds combined being able to affect the level of more than one marker protein, would make the treatment of the disease even more efficient.

The term "polypeptide" in the present invention should have its usual meaning. That is an amino add chain of any length, including a full-length protein, oligopeptides, short peptides and fragments thereof, wherein the amino add residues are linked by covalent peptide bonds. The terms "polypeptide", "peptide", "amino acid sequence" and "protein" are used interchangeably.

The protein may be chemically or biochemically modified by being phosphorylated, methylated, sulphylated, glycosylated or by the addition of any form of lipid or fatty add, ubiquitin or any other large side groups or by containing additional amino adds or any other forms of modification (of which there are over 200 known). These modifications occur at specific sites on the protein and a particular modification at one site can have different effects as the same modification at a different site on the same protein. They can be reversible in the cell where they are used for example to turn on and off enzymes and so the proteins can exist in a variety of forms—each with an associated activity level for each of the proteins functions. Furthermore the polypeptide may be cleaved e.g. by processing at its N- or C-termini to remove signal peptides or be spliced to remove an internal sequence. Examples of many of these can be found in the protein databases like EXPASY and there exist an ever growing range of tools to predict these modifications and their function (see http://www.expasy.ch/). Since it is estimated that each protein in man is modified on average 10 times, it is expected that the majority of the proteins identified here are modified in some way or another. Their apparent isoelectric point and molecular weight has thus been given in tables 1, 2 and 3 so that they can be compared to the theoretical values to indicate what effects the modification has had on the protein.

Each polypeptide may thus be characterized by specific amino adds and be encoded by specific nucleic add sequences. It will be understood that such sequences include analogues and variants produced by recombinant or synthetic methods wherein such polypeptide sequences have been modified by substitution, insertion, addition or deletion of one or more amino add residues in the recombinant polypeptide and still be immunogenic in any of the biological assays described herein. Substitutions are preferably "conservative". Conservative substitutions are known to a person skilled in the art preferably, amino adds belonging to the same grouping (non-polar (G, A, P, I, L and V), polar-uncharged (C, S, T, M, N and Q), polar-charged (D, E, K and R) and aromatic (H, F, W and Y)). Within these groups, amino adds may be substituted for each other, but other substitutions are of course possible.

Each polypeptide is encoded by a specific nucleic add sequence. It will be understood that such sequences include analogues and variants hereof wherein such nucleic add sequences have been modified by substitution, insertion, addition or deletion of one or more nucleic add residues (including the insertion of one or more introns (small or large)). Substitutions are preferably silent substitutions in the codon usage, which will not lead to any change in the amino add sequence, but may be introduced to enhance the expression of the protein.

In the present context the term "substantially pure polypeptide" means a polypeptide preparation which contains at most 5% by weight of other polypeptide material with which it is natively associated (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at last 99,25%, at least 99,5%, and at least 99,75%. It is especially preferred that the polypeptide fragment is in "essentially pure form", i.e. that the polypeptide fragment is essentially free of any other protein with which it is natively associated, i.e. free of any other protein from a mammal. This can be accomplished by preparing the polypeptide of the invention by means of recombinant methods in a host cell as known to a person skilled in the art, or by synthesizing the polypeptide fragment by the well-known methods of solid or liquid phase peptide synthesis, e.g. by the method described by Merrifield (Merrifield, R. B. Fed. Proc. Am. Soc. Ex. Biol. 21: 412, 1962 and J. Am. Chem. Soc. 85: 2149, 1963) or variations thereof, or by means of recovery from electrophoretic gels.

The term "protein" also encompasses derivatives, analogues and mimetics of the above mentioned polypeptides. Such a derivative, analogue and mimetic preferably have the same activity, e.g. the same kind of enzymatic activity, as the polypeptide which it is derived from. The derivative, analogue or mimetic can have a lower level activity, the same level or preferably, a higher level of activity than the parent polypeptide.

The term "a least one" (e.g. at least one compound or at least one marker protein) encompasses the integers 1, 2, 3, 4, 5, 6, 7, 8, 9, 10, 11, 12, 13, 14, 15, 16, 17, 18, 19 etc. It should be understood that a single marker protein can be used, but it can be advantageous to use more than one marker protein in methods of the invention. That is to say that the level of expression of more than one protein is established and the pattern of expression of a grouping of proteins is used as an indicator. Obviously the reliability of identification increases as the number in the group increase.

A "peptide mimetic" is a molecule that mimics the biological activity of a peptide but is no longer peptidic in chemical nature. By strict definition, a peptidomimetic is a molecule that no longer contains any peptide bonds (that is, amide bonds between amino acids). However, the term peptide mimetic is sometimes used to describe molecules that are no longer completely peptidic in nature, such as pseudo-peptides, semi-peptides and peptoids. Whether completely or partially non peptide, peptidomimetics according to this invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems, which are similar to the biological activity of the peptide. The present invention encompasses peptidomimetic compositions which are analogs that mimic the activity of biologically active peptides according to the invention, i.e. the peptidomimetics can be used for treatment of diabetes related diseases. The peptidomimetic of this invention are preferably substantially similar in both three dimensional shape and biological activity to the peptides or active sites of such as set forth above.

Alternatively, the mimetic can be an 'antimimetic'. In other words, a molecule that can fit into and block the active site of the protein, or bind to binding sites or sites of interaction with other biological molecules and so interfere with the function of the protein. Most current drugs are of this type. Such antimimetics that are capable of interacting with the polypeptides of the invention are encompassed by the present invention.

There are dear advantages for using a mimetic of a given peptide rather than the peptide itself, because peptides commonly exhibit two undesirable properties: (1) poor bioavailability; and (2) short duration of action. Peptide mimetics offer an obvious route around these two major obstacles, since the molecules concerned are small enough to be both orally active and have a long duration of action. There are also considerable cost savings and improved patient compliance associated with peptide mimetics, since they can be administered orally compared with parenteral or transmucosal administration for peptides. Furthermore, peptide mimetics are much cheaper to produce than peptides. Finally, there are problems associated with stability, storage and immunoreactivity for peptides that are not experienced with peptide mimetics.

Thus peptides described above have utility in the development of such small chemical compounds with similar biological activities and therefore with similar therapeutic utilities. The techniques of developing peptidomimetics are conventional. Thus, peptide bonds can be replaced by non-peptide bonds that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide by NMR spectroscopy, crystallography and/or computer-aided molecular modelling. These techniques aid in the development of novel compositions of higher potency and/or greater bioavailability and/or greater stability than the original peptide [Dean (1994), BioEssays, 16: 683-687; Cohen and Shatzmiller (1993), J. Mol. Graph. 11: 166-173; Wiley and Rich (1993), Med. Res. Rev., 13: 327-384; Moore (1994), Trends Pharmacol. Sci., 15: 124-129; Hruby (1993), Biopolymers, 33: 1073-1082; Bugg et al. (1993), Sci. Am., 269: 92-98, all incorporated herein by reference]. Once a potential peptidomimetic compound is identified, it may be synthesized and assayed using the diagnostic assay described herein or an appropriate disease suppressor assay [see, Finlay et al. (1983), Cell, 57: 1083-1093 and Fujiwara et al. (1993), Cancer Res., 53: 4129-4133, both incorporated herein by reference], to assess its activity.

Thus, through use of the methods described above, the present invention provides compounds exhibiting enhanced therapeutic activity in comparison to the polypeptides described above. The peptidomimetic compounds obtainable by the above methods, having the biological activity of the above named peptides and similar three dimensional structure, are encompassed by this invention. It will be readily apparent to one skilled in the art that a peptidomimetic can be generated from any of the modified peptides described previously or from a peptide bearing more than one of the modifications described previously. It will furthermore be apparent that the peptidomimetics of this invention can be further used for the development of even more potent non-peptidic compounds, in addition to their utility as therapeutic compounds.

By the terms "nucleic acidd fragment" and "nucleic acid sequence" and the like are understood any nucleic acid molecule including DNA, RNA, LNA (locked nucleic acids), PNA, RNA, dsRNA and RNA-DNA-hybrids. Also included are nucleic acid molecules comprising non-naturally occurring nucleosides. The term includes nucleic acid molecules of any length, e.g. from 10 to 10000 nucleotides, depending on the use. When the nucleic acid molecule is for use as a pharmaceutical, e.g. In DNA therapy, or for use in a method for producing a polypeptide according to the invention, a molecule encoding at least a part of the polypeptide is preferably used, having a length from about 18 to about 1000 nucleotides, the molecule being optionally inserted into a vector. When the nucleic acid molecule is used as a probe, as a primer or in antisense therapy, a molecule having a length of 10-100 is preferably used. According to the invention, other molecule lengths can be used, for instance a molecule having at least 12, 15, 21, 24, 27, 30, 33, 36, 39, 42, 50, 60, 70, 80, 90, 100, 200, 300, 400, 500 or 1000 nucleotides (or nucleotide derivatives), or a molecule having at most 10000, 5000, 4000, 3000, 2000, 1000, 700, 500, 400, 300, 200, 100, 50, 40, 30 or 20 nucleotides (or nucleotide derivatives). It should be understood that these numbers can be freely combined to produce ranges.

The term "stringent" when used in conjunction with hybridization conditions is as defined in the art, i.e. the hybridization is performed at a temperature not more than 15-20° C. under the melting point (Tm) of the nucleic acid fragment, d. Sambrook et al Molecular Cloning; A laboratory manual, Cold Spring Harbor Laboratories, NY, 1989, pages 11.45-11.49. Preferably, the conditions are "highly stringent", i.e. 5-10° C. under the melting point (Tm). In the present invention, the hybridisation conditions are preferably stringent.

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

The term "sequence identity" (or "sequence homology") indicates a quantitative measure of the degree of homology between two amino acid sequences of equal length or between two nucleotide sequences of equal length. If the two sequences to be compared are not of equal length, they must be aligned to best possible fit possible with the insertion of gaps or alternatively truncation at the ends of the protein sequences. The sequence identity can be calculated as $(N_{ref}-N_{dif})100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$). Sequence identity can alternatively be calculated by the BLAST program e.g. the BLASTP program (Pearson W. R and D. J. Upman (1988) PNAS USA 85:2444-2448) (www.ncbi.nlm.nih.gov/cgi-bin/BLAST). In one aspect of the invention, alignment is performed with the sequence alignment method ClustalW with default parameters as described by Thompson J., et al Nucleic Acids Res 1994 22:4673-4680, available at http://www2.ebi.ac.uk/clustalw/. Alternatively, the degree of homology between two nucleic acid sequences is determined by using GAP version 8 from the GCG package with standard penalties for DNA: GAP weight 5.00, length weight 0.300, Matrix described in Gribskov and Burgess, Nucl. Acids Res. 14(16); 6745-6763 (1986), and the degree of homology between two amino acid sequences is determined by using GAP version 8 from the GCG package (Genetics Computer Group, 575 Science Drive, Madison, Wis. 53711, USA) with standard penalties for proteins: GAP weight 3.00, length weight 0.100, Matrix described in Gribskov and Burgess, Nucl. Adds Res. 14(16); 6745-6763 (1986).

A preferred minimum percentage of sequence homology is at least 70%, such as at least 80%, at least 85%, at least 90%, at least 91%, at least 92%, at least 93%, at least 94%, at least 95%, at least 96%, at least 97%, at least 98%, at least 99%, and at least 99.5%.

The invention also relates to the use of a polypeptide or nucleic acid of the invention for use as therapeutic vaccines as have been described in the literature exemplified by Lowry, D. B. et al 1999, Nature 400: 269-71.

A monoclonal or polyclonal antibody, which is specifically reacting with a polypeptide of the invention in an immuno assay, or a specific binding fragment of said antibody, is also a part of the invention. The antibodies can be produced by methods known to a person skilled in the art. The polyclonal antibodies can be raised in a mammal, for example, by one or more injections of a polypeptide according to the present invention and, if desired, an adjuvant. The monoclonal antibodies according to the present invention may, for example, be produced by the hybridoma method first described by Kohler and Milstein, Nature, 256:495 (1975), or may be produced by recombinant DNA methods such as described in U.S. Pat. No. 4,816,567. The monoclonal antibodies may also be isolated from phage libraries generated using the techniques described by McCafferty et al, Nature, 348:552-554 (1990), for example. Methods for producing antibodies are described in the literature, e.g. In U.S. Pat. No. 6,136,958.

In diagnostics, treatment or testing, an antibody, a nucleic acid fragment and/or a polypeptide of the invention can be used either alone, or as a constituent in a composition. Such compositions are known in the art, and comprise compositions in which the antibody, the nucleic acid fragment or the polypeptide of the invention is coupled, preferably covalently, to at least one other molecule, e.g. a label (e.g. radioactive or fluorescent) or a carrier molecule.

The present invention is further directed to methods for using the compounds described above to therapeutically and/or prophylactically treat a patient for a diabetes related disease.

The methods of the present invention include the steps of: a) incorporating one or more of the compounds of the present invention in a suitable pharmaceutical carrier; and b) administering either a therapeutically effective dosage or a prophylactically effective dosage of the compound or compounds incorporated in the carrier to a patient The term "suitable pharmaceutical carrier" refers to any carrier known in the pharmaceutical arts for administration of compounds to a patient. Any suitable pharmaceutical carrier can be used according to the present invention, so long as compatibility problems do not arise.

Administration of an effective dosage to a patient can be accomplished by parenteral injection, such as intravenously, intrathecally, intramuscularly or intra-arterially. The compounds can also be administered orally or transdermally, or by any other means known to those skilled in the art, e.g. by means of an inhalator or a nasal spray. Oral administration is presently preferred.

As used herein, the term "therapeutically effective amount" refers to that amount of one or more of the compounds of the present invention required to therapeutically treating a patient. Such treatment is appropriate for subjects having a diagnosed diabetes related disease. Similarly, the term "prophylactically effective amount" refers to that amount of one or more of the compounds of the present invention needed to prophylactically treat a patient. Such treatment is appropriate for subjects who, for example, have not yet established any clinical symptoms of a diabetes related disease. It could be advantageous to start a prophylactic treatment as soon it is determined that the subject is in risk for developing a diabetes related disease, e.g. by means of a determination of a predisposition for diabetes by having an altered level of markers.

As will be appreciated by a person skilled in the art, the dosage of compound given, the route of administration and the duration of therapy will be dependent not only the type of compound and its effectiveness in treating the disease but also upon the individual being treated, taking into consideration such factors as the body weight of the patient, other therapies being employed to treat the patient, and the condition, clinical response and tolerance of the patient. Dosage, administration, and duration of therapy can be determined by one skilled in the art upon evaluation of these and other relevant factors.

EXAMPLES

Example 1

The aim was to describe PIPP induced by 24 hours of incubation with 150 pg/ml recombinant human IL-1β (specific activity was 400 U/ng, Novo Nordisk, Bagsvaerd, Denmark) in neonatal BB-DP rat islets identified by 2-DGE of labelled islets (n=3 for each group) [Christensen, 2000] [13]. Protein spots that significantly changed expression levels after exposure to IL-1β were cut out of preparative gels and subjected to MS.

Preparatory 2D-gels were produced from a pod of approximately 200.000 neonatal WF islets isolated, prepared and separated on gels as described above. For localization of the spots, radioactively labelled tracer islets were mixed with the non-labelled islets. Neonatal WF rat islets were used for preparatory gets because of the price and number of islets isolated per animal. The pattern seen on 2D-gels of respectively BB-DP and WF rat islets are similar. The cost of one WF rat is approximately one tenth of the price of a BB-DP rat (approximately 100 US$ each). From each rat is it possible to isolate in the range of 150-200 islets.

Reagents

RPMI 1640, Hanks' balanced salt solution (HBSS) and Dulbecco's modified Eagle's medium (DMEM) (Gibco, Paisley, Scotland). RPMI 1640 contained 11 mmol D-glucose and was supplemented with 20 mM HEPES buffer, 100,000 IU/l penicillin and 100 mg/l streptomycin. Other reagents: 2-mercaptoethanol, foetal calf serum (BSA), normal human serum (NHS), Tris HCl, Tris base, glycine, (Sigma, St. Louis, USA); trichloracetic acid (TCA), phosphoric acid, NaOH, glycerol, n-butanol, bromophenol blue, H3PO4 and NaNO2 (Merck, Darmstadt, Germany); filters (HAWP 0.25 mm pore size) (Millipore, Boston, USA); RNA'se A, DNA'se I (Worthington, Freehold, N.J., USA); [35S]-methionine (SJ 204, specific activity: >1.000 Cl/mmol, containing 0.1% 2-mercaptoethanol), Amplify® (Amersham International, Amersham, UK); urea (ultra pure) (Schwarz/Mann, Cambridge, Mass., USA); acrylamide, bisacrylamide, 4N-tetra-methyl-ethylene-diamine (TEMED), ammonium persulphate (BioRad, Richmond, Calif., USA); ampholytes: pH 5-7, pH 3.5-10, pH 7-9, pH 8-9.5 (Amasham Biotech, Sweden); Nonidet P-40 (BDH, Poole, UK); ampholytes: pH 5-7 and sodium dodecyl sulphate (Serva, Heidelberg, Germany); agarose (Litex, Copenhagen, Denmark); ethanol (absolute 96%) (Danish Distillers, Aalborg, Denmark); methanol (Prolabo, Brione Le Blanc, France); acetic acid (technical quality, 99% glacial) (Ble & Berntsen, Århus, Denmark) and X-ray film (Curix RP-2) (AGFA).

Animals

Pregnant inbred WF rats were purchased from M&B, Li. Skensved, Denmark. Four to five day-old BB/Wor/Mol-BB2 (BB-DP) rats were also purchased from M&B. The rats were picked up at M&B in the morning on the day of islet isolation, and transported in animal transport boxes. At M&B the BB-DP rats were housed separately in a specific pathogen-free environment Isolation, Culture and Labelling of Islets for Preparative Gels Islets were isolated by collagenase digestion of the pancreata from 4-5 day old WF rats [Brunstedt, 1984] [15]. After 4 days of preculture in RPMI 1640+10% fetal calf serum, islets were incubated for 24 h in 37° C. humidified atmospheric air in 300 µl or 3000 µl RPMI 1640+0.5% normal human serum. Next islets were washed twice in HBSS and labelled for 4 h at 37° C. in 200 µl or 2000 µl home made methionine-free Dulbecco's modified Eagle's medium (DMEM) with 10% dialysed NHS, and 200 µCl [35S]-methionine. To eliminate 2-mercaptoethanol, [35S]-methionine was freeze-dried for at least 4 h before labelling. A labelling, the isles were washed thrice in HBSS, the supernatant was removed and islets were immediately frozen at −80° C. Unlabelled islets for preparative gels were washed twice in HBSS and snapfrozen. For localization of the spots, radioactively labelled tracer islets were mixed with the non-labelled islets.

Sample Preparation

The frozen islets were re-suspended in 100 µl DNAseI/RNAse A solution and lysed by freeze-thawing twice. After the second thawing, the samples were left on ice for 30 min. for the digestion of nucleic acids and then freeze dried overnight. The samples were dissolved by shaking in 120 µl lysis buffer (8.5 M urea, 2% Nonidet P-40, 5% 2-mercaptoethanol and 2% ampholytes, pH range 7-9) for a minimum of 4 hours.

Determination of [35S]-methionine Incorporation

The amount of [35S]-methionine incorporation was quantified by adding 10 µl FCS (0.2 µg/ml H2O) as a protein-carrier to 5 µl of a 1:10 dilution of each sample in duplicate, followed by 0.5 ml of 10% TCA. This was left to precipitate for 30 min at 4° C. before being filtered through 0.25 µm hydroxy appatit-WP (HAWP) filters. The filters were dried and placed into scintillation liquid for counting.

2-DGE and Preparative Gels

Preparative two dimensional gels (2-DG) were produced from a pool of approximately 200.000 neonatal WF rat islets isolated, cultured, labelled and separated on gels as described above. For localization of the spots, radioactively labelled tracer islets were mixed with the non-labelled islets.

The procedure has been described earlier [O'Farrell, 1977 [14]; Fey, 1984 [18]; Fey, 1997 [17]. Briefly, first dimension gels contained 4% acrylamide, 0.25% bisacrylamide, ampholytes and nonidet P-40. Equal amount of protein (175-200 µg for preparative gels) and counts per minute (106 cpm.) of each sample were applied to the gels. Both isoelectric focusing (IEF; pH 3.5-7) and non-equilibrium pH-gradient electrophoresis (NEPHGE; pH 6.5-10.5) gels were made. Second dimension gels contained 12,5% acrylamide and 0.063% bisacrylamide and were run overnight. After electrophoresis, the gels were fixed and treated for fluorography with Amplify® before being dried. The gels were placed in contact with X-ray films and exposed at −70° C. for 3 to 40 days. Each gel was exposed for at least 3 time periods to compensate for tile lack of dynamic range of X-ray films.

Neonatal WF rat islets were used for preparative gels because of the price and higher number of islets isolated per animal. The same protein spot pattern is seen on 2-DG of respectively BB-DP and WF rat islets and the BB-DP rat originates from the WF rat. The cost of one WF rat is approximately one tenth of the price of a BB-DP rat (approximately 100 US$ each). From each rat was it possible to isolate approximately 150-200 islets.

Determination of Mr and pI

Mr and pI for individual proteins on the gels were interpolated from landmark proteins. Landmark proteins were determined by use of internal standards and pI calibration kits [Fey, 1984] [18]. Theoretical Mr and pI were calculated using the Compute pI/Mw tool at the ExPASy Molecular Biology Server (www.expasy.ch/tools/pi_tool.html).

Computer Analysis of Fluorographs

Computer analysis was performed using the BioImage® program 2D-Analyzer (version 6.1) [Christensen, 2000] [13]. Briefly, computer analysis was performed using the BioImage® program 2D-Analyzer (version 6.1) on a Sun Ultra 1 computer. First, the fluorographs were scanned and spots identified and quantified by the 2D-Analyzer. Next, anchor points were placed on the gel (same spot in each gel was assigned the same anchor-point), and an initial computer based match of the gels was performed. After computer matching, manual editing was performed to ensure correct matching of computer found spots as well as matching and quantification of spots not found by the initially computer matching. Approximately 30% of the spots were matched correct by the computer. Finally, data were extracted for calculations in the Quatro Pro® spreadsheet (Borland version 4.0). To avoid the presence of duplicate spots in the IEF and NEPHGE subgroups, overlapping spots in either the basic part of IEF gels or in the acidic part of NEPHGE gels were omitted from analysis.

Protein Identification by Matrix-Assisted Laser Desorption/Ionization (MALDI) MS Briefly, the 82 protein spots of interest were obtained by cutting them out of the dried gel using a scalpel. The proteins were enzymatically digested in the gel piece as described [Rosenfeid, 1992 [19]; Shevchenko, 1996 [20]] with minor modifications [Nawrocki, 1998] [21]. The excised gel pieces were washed in 50 mM NH4HCO3/acetonitrile (60/40) and dried by vacuum centrifugation. Modified porcine trypsin (12 ng/µL, Promega, sequencing grade) in digestion buffer (50 mM NH4HCO3) was added to the dry gel pieces and incubated on ice for 1 h for reswelling. After removing the supernatant, 20-40 µL digestion buffer was added and the digestion was continued at 37° C. for 4-18 hours. The peptides were extracted as described [Shevchenko, 1996] [20] and dried in a vacuum centrifuge. The residue was dissolved in 5% formic acid and analysed by MALDI MS. Delayed extraction MALDI mass spectra of the peptide mixtures were acquired using a Bruker Reflex time-of-flight mass spectrometer (Briker AG, Germany). Samples were prepared using a-cyano-4-hydroxy cinnamic acid as matrix [Kussmann, 1997][221]. Protein identification was performed by in silico comparison of the theoretical peptide-mass maps in the comprehensive, non-redundant protein sequence database (NRDB, European Bioinformatics Institute, Hinxton, UK http://www.ebi.ac.uk) using the PeptideSearch software ([Mann, 1993][23] further developed at EMBL (Heidelberg, Germany)), SWISS-PROT (http://www.expasy.ch), PIR (http://wwww.sanger.ac.uk/DataSearch), NIH and GENEBANK (http://www.ncbi.nim.nih.gov). The protein identifications were examined using the "second pass search" feature of the software and critical evaluation of the peptide mass map as described [Jensen, 19981][24].

Protein Information

Information about the identified proteins known and putative biological functions were found at The ExPASy Molecular Biology Server (http://www.exasy.ch) and at The National Centre for Biotechnology Information (NCBI) (http://www.ncbl.nim.nih.gov).

Statistical Analysis

Student's t-test was applied and $\rho<0.01$ was chosen as level of significance.

Results

All 82 significantly changed protein spots were re-identified in preparative gels of neonatal WF islets and could be excised from the gels for MS identification. Positive identification was obtained for a total of 45 different proteins from 51 of the 82 spots (table 1). Six spots contained 2 identifiable proteins (NEPHGE match no. 339, 370 and IEF 955, 248, 1136, 660). Some proteins were present in more than one spot: Three proteins were present in 2 spots (Heterogeneous nuclear ribonucleoproteins A2/B1, calreticulin and NADH dehydrogenase), 3 proteins were present in 3 spots (malate dehydrogenase precursor (mitochondrial), IgE binding protein and glucose-regulated protein 78 (GRP 78)) and one protein, tubulin beta-5 chain was present in 4 spots. The presence of the same protein in more than one spot suggests that the protein exists in different posttranslatory modified or degraded forms. Positive identification was not obtained for 31 protein spots either due to spectra with no data base match (n=16) or low abundance of peptides in the excised and digested spots (n=15) (table 2). Thus, success rate of positively identified protein spots was 62% (51 spots out 82). A similar result, 60 spots identified out of 105 (58%) were obtained from WF rat islets exposed to IL-1β, corresponding to 57 different proteins [Mose Larsen, 2001] [7]. Thirteen proteins identified in BB-DP and WF rat islets were identical (NEPHGE match no. 223, 231, 370, 146, 381 (2 spots), IEF match no. 1127, 955, 552, 138 (3 spots), 1136, 8580, 68, 62) (table 1).

In table 1, the protein Mr's and pI's observed on the gels are presented together with the computed theoretical Mr and pI values. Differences in observed and computed values of Mr and pI may be due to posttranslatory modifications, degradation or pro- or pre-pro forms of proteins since the theoretical values are based on the open reading fame only. For example calreticulin is present in 2 spots with a Mr of respectively 39.9 kDa and 120.7 kDa whereas the theoretical value is 48 kDa. Nevertheless for most proteins there are only minor differences between observed Mr/pI values and theoretical values (table 1).

In total, 45 different proteins and 12 modified forms of some of these proteins have been identified to change expression level after exposure to IL-1β. Based upon known or putative functions the 45 identified proteins (with modified forms 57) have been grouped as follows (in brackets, number of different proteins): proteins involved in a) energy transduction and redox potentials (n=8), b) glycolytic and Krebs cycle enzymes (n=6), c) protein synthesis (including purin/pyrimidine synthesis, DNA/RNA synthesis, RNA processing and amino add metabolism), chaperoning and protein folding (n=14), d) signal transduction, regulation, differentiation and apoptosis (n=6), e) cellular defence (n=2) and f) other functions (n=9) (table 1).

Legends

Table 1

Identified protein spots in neonatal BB-DP rats islets after exposure to IL-1β. Changes in protein expression level are expressed as % IOD in neonatal BB-DP islets after IL-1β incubation in vitro compared to BB-DP islets without IL-1β. Match numbers are arbitrary numbers given by the computer and corresponds to the number of the spot in the gel. % IOD refers to the integrated optic density on the control gels. % OD ratio refers to the ratio of integrated optical density between gels compared. Numbers below 1 indicate proteins down-regulated and numbers above 1 are up-regulated in islets exposed to IL-1β. The proteins spots are ordered according to functional groups and % IOD ratio. First spots on the NEPHGE (prefix N) side and next the IEF (prefix I) side. Protein name refers to the name found in the NCBI database (http://www.ncbi.nim.nih.aovg through the database accession number. Given is the Mr and pI obtained directly by the gel analysis and the calculated theoretical Mr and pI calculated from the amino acid sequence. In some spots more than one protein was identified. These proteins are marked with *. Proteins mentioned more than once are found in more than one spot. Proteins previously identified as changes in expression in WF rat islets exposed to IL-1β as well [Mose Larsen, 2001] [7] are marked with #. Proteins that have not previously been described or supposed to be present in islets are marked with $.

Table 2

In table 2, unidentified protein spots with significant change in expression level expressed as % IOD In neonatal BB-DP islets after IL-1β incubation in vitro are compared to BB-DP islets without IL-1β. Match numbers are arbitrary numbers given by the computer and corresponds to the number of the spot in the gel. % IOD ratio refers to the ratio of integrated optical density between gels compared. Numbers below 1 are downs-regulated and numbers above 1 are up-regulated in islets exposed to IL-1β. Protein spots are ordered numerically. First spots on the IEF (prefix I) side and next on the NEPHGE (prefix N) side. The Mr in kDa and pI obtained directly from the gels are given. Where spectra were obtained by tryptic digestion, their Mr of the peptides is given in table 3 and their spectra given in pairs of figures as shown.

FIG. 1

Fluorograph of a two-dimensional gel of neonatal BB-DP rat islets of Langerhans incubated for 24 hours in control medium followed by 4 hours labeling with [35S]-methionine. The gel shown is representative of 3 experiments. The marked proteins represents proteins changing level of expression during incubation with IL-1β. IEF gel (pH 3.5-7) on the right side and NEPHGE gel (pH6.5-10.5) on the left side. The numbers correspond to the proteins in table 1 and 2.

FIGS. 3A-19D Spectra of the proteins in table 3. Each spectrum is presented firstly as a total spectrum (e.g. FIG. 3A) and thereafter as enlarged regions so it is possible to read all the numbers and see the peak that they refer to (e.g. FIG. 3B, FIG. 3C, etc.). Thus, the spectra for the first protein in table 3 are called FIG. 3A, FIG. 3B, FIG. 3C and FIG. 3D.

TABLE 1

Identification of proteins induced by IL-1β in BB-DP rat islets

| Gel match No | % IOD | % IOD ratio | Protein name | Function | Database acc. no. | Mr. | Theoretical Mr. | pI | Theoretical pI |
|---|---|---|---|---|---|---|---|---|---|
| | | | | Energy transduction and redox potentials | | | | | |
| N 318 | 0.165 | 0.56 | Alcohol dehydrogenase | Redox potential | gi 1703237 | 42.4 | 36.4 | 7.8 | 6.8 |
| N 231# | 0.041 | 0.51 | ATP synthase alpha chain, mitochondrial precursor | Energy transduction | gi 114523 | 51.1 | 58.8 | 7.9 | 9.2 |
| N 370*# | 2.055 | 0.24 | L-3-hydroxyacyl-CoA dehydrogenase precursor | Energy transduction, redox potential | gi 5353512 | 36.5 | 34.3 | 8.4 | 8.9 |
| N 1247 | 0.084 | 0.20 | Carbonyl reductase | Redox potential | gi 1352258 | 37.7 | 30.4 | 8.2 | 8.2 |
| I 955*# | 0.104 | 2.41 | Creatine kinase-B | Energy transduction | gi 203476 | 49.3 | 42.7 | 5.4 | 5.3 |
| I 1136* | 0.405 | 0.45 | H+ transporting ATP synthase | Energy transduction | gi 92350 | 52.9 | 56.4 | 4.8 | 5.2 |
| I 706 | 0.086 | 0.43 | NADH dehydrogenase | Energy transduction | gi 4826856 | 86.7 | 79.6 | 5.3 | 5.8 |
| I 705 | 0.084 | 0.35 | NADH dehydrogenase | Energy transduction | gi 4826856 | 87.3 | 79.6 | 5.2 | 5.8 |
| I 552# | 0.132 | 0.07 | ATPase, H+ transporting, lysosomal (vacuolar proton pump), beta polypeptide, 56/58 kD, isoform 1 | Energy transduction, Intracellular environment | gi 4502309 | 57.6 | 57.0 | 5.3 | 5.5 |
| | | | | Glycolytic and Krebs Cycle enzymes | | | | | |
| I 629 | 0.065 | 2.15 | Glucose-6-phosphate dehydrogenase | Energy generation | gi 204197 | 61.8 | 59.2 | 6.0 | 6.0 |
| I 1127# | 0.067 | 0.29 | Glyceraldehyde-3-phosphate dehydrogenase | Energy generation | gi 203142 | 54.4 | 35.7 | 6.7 | 8.4 |
| N 223# | 0.379 | 0.52 | Pyruvate kinase M2 Isozyme | Energy generation | gi 1346398 | 55.6 | 57.6 | 8.0 | 7.4 |
| N 88 | 0.288 | 0.41 | Aconitate hydratase, mitochondriel precursor | Energy generation | gi 1351857 | 77.8 | 85.4 | 7.3 | 8.1 |
| N 272 | 0.433 | 0.48 | Isocitrate dehydrogenase 2, mitochondrial | Energy generation | gi 6680343 | 45.9 | 58.7 | 8.4 | 8.9 |
| N 1325 | 0.137 | 0.38 | Malate dehydrogenase precursor, mitochondrial | Energy generation | gi 319830 | 41.9 | 35.5 | 9.0 | 8.9 |
| N 336 | 0.118 | 0.36 | Malate dehydrogenase precursor, mitochondrial | Energy generation | gi 319830 | 42.7 | 35.5 | 9.0 | 8.9 |
| N 339* | 0.830 | 0.28 | Malate dehydrogenase precursor, mitochondrial | Energy generation | gi 319830 | 40.4 | 35.5 | 8.7 | 8.9 |
| | | | | Protein synthesis (incl. DNA/RNA processing and synthesis, purin/pyrimidine synthesis, amino acid metabolism) chaperones and protein folding | | | | | |
| N 146# | 0.590 | 0.44 | 5-aminoimidazole-4-carboxamide ribonucleotide formyltransferase | Purine/pyrimidine synthesis, DNA/RNA synthesis | gi 2541906 | 64.8 | 64.2 | 6.9 | 6.7 |
| I 248* | 0.030 | 0.48 | Adenosine phosphoribosyltrasferase | Purine/pyrimidine synthesis, DNA/RNA synthesis | gi 543829 | 21.5 | 19.5 | 5.7 | 6.2 |
| I 248* | 0.030 | 0.48 | UMP-CMP kinase | Purine/pyrimidine synthesis, DNA/RNA synthesis | gi 5730476 | 21.5 | 22.2 | 5.7 | 5.4 |
| N 1414 | 0.070 | 0.41 | Heterogeneous nuclear ribonucleoprotein A2/B1 | RNA-processing | gi 6647752 | 42.1 | 36.0 | 8.0 | 8.7 |
| N 339* | 0.830 | 0.28 | Heterogeneous nuclear ribonucleoprotein A2/B1 | RNA-processing | gi 6647752 | 40.4 | 36.0 | 8.7 | 8.7 |
| N 1401 | 0.482 | 0.17 | M4 protein deletion mutant | RNA-processing | gi 3126878 | 64.4 | 77.5 | 8.5 | 8.9 |
| N 317 | 0.071 | 0.35 | Aspartate transaminase, cytosolic | Amino acid metabolism | gi 91997 | 44.9 | 46.2 | 7.9 | 6.3 |
| N 1322 | 0.054 | 0.15 | Aspartate aminotransferase, mitochondrial precursor | Amino acid metabolism | gi 112987 | 47.6 | 47.3 | 9.1 | 9.1 |
| I 237 | 0.534 | 0.12 | 60 ribosomal protein L11 | Ribosome protein | gi 971761 | 20.9 | 18.8 | 4.4 | 9.9 |
| I 653 | 0.722 | 1.52 | Calreticulin | Chaperone, transcription factor | gi 6680836 | 120.7 | 48.0 | 3.7 | 4.3 |
| I 585 | 0.061 | 2.82 | Calreticulin | Chaperone, transcription factor | gi 6680836 | 39.9 | 48.0 | 6.0 | 4.3 |
| I 138# | 0.881 | 1.79 | 78 kD glucose-regulated protein precursor (GRP 78) (HSP70 family) | Chaperone, signal transduction | gi 121574 | 78.4 | 72.3 | 4.8 | 5.1 |
| I 660*# | 0.208 | 0.18 | 78 kD glucose-regulated protein precursor (GRP 78) (HSP70 family) | Chaperone, signal transduction | gi 121574 | 70.2 | 72.3 | 4.8 | 5.1 |
| I 6347# | 0.173 | 0.39 | 78 kD glucose-regulated protein precursor (GRP 78) (HSP70 family) | Chaperone, signal transduction | gi 121574 | 65.1 | 72.3 | 4.9 | 5.1 |
| I 1136*# | 0.405 | 0.45 | Probable protein disulfide isomerase P5 precursor | Chaperone, signal transduction | gi 2501206 | 52.9 | 47.2 | 4.8 | 5.0 |
| I 8580# | 0.034 | 0.38 | Protein disulfide isomerase | Chaperone, signal transduction | gi 91897 | 60.2 | 56.6 | 6.0 | 5.9 |
| I 68# | 0.084 | 0.23 | Endoplasmic reticulum protein ERP 29 precursor | Chaperone, signal transduction | gi 2507015 | 25.9 | 28.6 | 6.3 | 6.2 |
| I 660* | 0.208 | 0.18 | Endoplasmin precursor (HSP90 family) | Chaperone, signal transduction | gi 119362 | 70.2 | 92.5 | 4.8 | 4.7 |

TABLE 1-continued

Identification of proteins induced by IL-1β in BB-DP rat islets

| Gel match No | % IOD | % IOD ratio | Protein name | Function | Database acc. no. | Mr. | Theoretical Mr. | pI | Theoretical pI |
|---|---|---|---|---|---|---|---|---|---|
| | | | | Signal transduction, regulation, differentiation and apoptosis | | | | | |
| N 381# | 0.495 | 3.93 | Galectin-3 (IgE binding protein) | Differentiation, apoptosis | gi 204728 | 36.8 | 27.1 | 7.9 | 8.2 |
| N 377# | 3.926 | 2.11 | Galectin-3 (IgE binding protein) | Differentiation, apoptosis | gi 204728 | 36.9 | 27.1 | 8.3 | 8.2 |
| N 398# | 0.007 | 28.15 | Galectin-3 (IgE binding protein) | Differentiation, apoptosis | gi 204728 | 31.4 | 27.1 | 8.8 | 8.2 |
| N 370* | 2.055 | 0.24 | Voltage dependent anion channel | Cellular transport, apoptosis | gi 4105605 | 36.5 | 32.4 | 8.4 | 8.3 |
| I 62# | 0.060 | 3.24 | TOAD 64 (Dihydropyrimidinase related protein-2) | Differentiation, signal transduction | gi 1351260 | 69.5 | 62.3 | 6.3 | 6.0 |
| I 1153 | 0.094 | 1.42 | Eukaryotic initiation factor 4A-like NUK | Signal transduction | gi 729821 | 44.8 | 46.8 | 6.3 | 6.1 |
| I 217 $ | 0.005 | 23.63 | Craniofacial development protein 1 | Eukaryotic organogenesis | gi 5453567 | 19.9 | 33.6 | 5.2 | 4.8 |
| I 293 | 0.686 | 0.24 | Secretagogin | Proliferation, differentiation, signal transduction | gi 3757661 | 25.8 | 32.1 | 5.5 | 5.3 |
| | | | | Cellular defence | | | | | |
| N 180 | 0.096 | 3.03 | Catalase | Cellular defence | gi 115707 | 61.9 | 59.6 | 7.5 | 7.2 |
| I 2420 | 0.026 | 0.13 | Glutathione synthetase | Cellular defence | gi 1170038 | 51.9 | 52.3 | 5.3 | 5.5 |
| | | | | Other functions | | | | | |
| I 1096 | 0.169 | 0.17 | Neuroendocrine convertase 1 | Hormone processing | gi 128001 | 73.8 | 84.1 | 4.7 | 5.8 |
| I 6363 | 0.229 | 0.12 | Neuroendocrine convertase 2 | Hormone processing | gi 128004 | 72.1 | 70.8 | 5.2 | 5.9 |
| N 279 | 0.271 | 0.33 | Beta-alanine oxoglutarate aminotransferase | GABA catabolism | gi 3046865 | 49.8 | 56.5 | 8.0 | 8.5 |
| I 1202$ | 0.035 | 0.03 | 25-Dx | Progesterone receptor | gi 1518818 | 24.3 | 21.5 | 4.2 | 4.5 |
| N 432 | 0.086 | 0.17 | Amyloid beta-peptide binding protein | Hormone metabolism, apoptosis | gi 2961553 | 30.9 | 27.1 | 8.5 | 8.9 |
| I 299 | 0.129 | 0.24 | 5-aminolevulinate synthase precursor | Heme synthesis | gi 599830 | 26.8 | 71.1 | 4.8 | 9.0 |
| I 955* | 0.104 | 2.41 | Cytokeratine 8 polypeptide | Cellular structure | gi 203734 | 49.3 | 53.9 | 5.4 | 5.8 |
| I 2410 | 0.331 | 0.46 | Tubulin beta-5 chain | Cellular structure | gi 135471 | 58.1 | 49.7 | 4.6 | 4.8 |
| I 6379 | 0.383 | 0.44 | Tubulin beta-5 chain | Cellular structure | gl 135471 | 65.7 | 49.7 | 4.5 | 4.8 |
| I 590 | 0.485 | 0.41 | Tubulin beta-5 chain | Cellular structure | gl 135471 | 64.9 | 49.7 | 4.5 | 4.8 |
| I 1139 | 0.561 | 0.37 | Tubulin beta-5 chain | Cellular structure | gl 135471 | 59.5 | 49.7 | 4.6 | 4.8 |
| N 1512 $ | 0.038 | 0.14 | Immediate-early protein 1 rat cytomegalovirus | Virus protein, transcription factor | gl 543613 | 51.6 | 66.7 | 8.4 | 4.7 |

TABLE 2

| Gel match No | % IOD ratio | Protein identification | Apparent Mr. | Apparent pI | Peptide fragment list | Spectrum shown in figures |
|---|---|---|---|---|---|---|
| I 75 | 0.43 | Weak spectrum no id | 62.2 | 6.5 | Table 3 | 3A-3D |
| I 242 | 0.08 | No spectrum | 20.6 | 5.0 | | |
| I 266 | 1.77 | Weak spectrum no id | 24.8 | 4.8 | Table 3 | 4A-4D |
| I 270 | 0.22 | Good spectrum no id | 22.5 | 5.4 | Table 3 | 5A-5C |
| I 275 | 0.26 | No spectrum | 22.7 | 6.0 | | |
| I 292 | 0.08 | Weak spectrum no id | 24.8 | 4.5 | Table 3 | 6A-6E |
| I 327 | 0.43 | No spectrum | 24.4 | 6.5 | | |
| I 408 | 0.70 | Weak spectrum no id | 32.5 | 5.9 | Table 3 | 7A-7D |
| I 418 | 0.18 | Good spectrum Protein Name: Pyridoxal kinase | 33.2 | 6.3 | Table 3 | 8A-8E |
| I 545 | 0.11 | No spectrum | 54.8 | 4.5 | | |
| I 683 | 3.36 | Weak spectrum no id | 72.9 | 6.3 | Table 3 | 9A-9E |
| I 712 | 0.26 | No spectrum | 90.1 | 5.4 | | |
| I 838 | 0.20 | No spectrum | 65.1 | 4.9 | | |
| I 961 | 2.58 | Good spectrum no id | 52.0 | 5.1 | Table 3 | 10A-10E |
| I 1196 | 0.22 | No spectrum | 24.4 | 6.1 | | |
| I 6585 | 0.42 | No spectrum | 30.2 | 6.0 | | |
| I 7495 | 0.04 | No spectrum | 30.2 | 5.6 | | |
| I 8264 | 21.03 | Good spectrum no id | 13.7 | 6.6 | Table 3 | 11A-11H |
| I 8311 | 0.08 | Weak spectrum no id | 21.3 | 4.5 | Table 3 | 12A-12C |
| I 8330 | 0.27 | No spectrum | 25.5 | 4.4 | | |
| N 68 | 0.12 | Weak spectrum no id | 89.1 | 6.4 | Table 3 | 13A-13C |
| N 207 | 0.38 | No spectrum | 57.4 | 8.8 | | |
| N 212 | 0.33 | Weak spectrum no id | 57.0 | 8.5 | Table 3 | 14A-14E |
| N 268 | 3.13 | Good spectrum no id | 47.7 | 8.6 | Table 3 | 15A-15E |

TABLE 2-continued

| Gel match No | % IOD ratio | Protein identification | Apparent Mr. | Apparent pI | Peptide fragment list | Spectrum shown in figures |
|---|---|---|---|---|---|---|
| N 281 | 9.29 | No spectrum | 46.1 | 8.0 | | |
| N 284 | 5.38 | No spectrum | 46.9 | 7.7 | | |
| N 403 | 0.31 | Weak spectrum no id | 31.8 | 8.5 | Table 3 | 16A-16C |
| N 435 | 6.03 | Weak spectrum no id | 29.0 | 8.3 | Table 3 | 17A-17C |
| N 509 | 1.50 | Weak spectrum no id | 23.9 | 7.9 | Table 3 | 18A-18C |
| N 1282 | 28.67 | No spectrum | 31.8 | 8.8 | | |
| N 1355 | 0.25 | Good spectrum no id | 44.1 | 8.0 | Table 3 | 19A-19D |

TABLE 3

Molecular weights of the tryptic peptide fragments of novel proteins for which spectra were obtained but for which no match existed in the current databases.

IEF proteins
Protein I 75

| | | | | | |
|---|---|---|---|---|---|
| 670.5570 | 684.5477 | 686.5041 | 728.5521 | 873.5858 | 889.6078 |
| 908.6622 | 922.6956 | 944.6519 | 950.7223 | 966.7041 | 984.6715 |
| 1004.5717 | 1077.7616 | 1086.6330 | 1132.6399 | 1166.6526 | 1168.6858 |
| 1185.7015 | 1193.6042 | 1242.5950 | 1263.6976 | 1272.7057 | 1342.0115 |
| 1355.8121 | 1357.8145 | 1442.7404 | 1455.7503 | 1488.8207 | 1524.8321 |
| 1564.7202 | 1607.8029 | 1615.8367 | 1716.8597 | 1861.9241 | 1940.9596 |
| 2034.8915 | 2053.0293 | | | | |

Protein I 266

| | | | | | |
|---|---|---|---|---|---|
| 728.5354 | 831.5264 | 873.5511 | 886.4743 | 908.6607 | 918.4865 |
| 922.6664 | 944.6254 | 949.5555 | 980.5395 | 1057.5931 | 1084.5941 |
| 1193.6314 | 1234.6795 | 1245.5738 | 1261.5759 | 1358.7697 | 1404.6458 |
| 1434.7914 | 1512.7986 | 1561.9757 | 1601.7975 | 1617.8125 | 1650.9545 |
| 1716.8823 | 1783.8355 | 1815.9457 | 1837.9834 | 1851.9422 | 1887.9667 |
| 1917.9224 | 1933.9909 | 1997.9097 | 2046.0106 | 3606.3085 | |

Protein I 270

| | | | | | |
|---|---|---|---|---|---|
| 679.5086 | 728.5476 | 854.4555 | 908.6556 | 944.5150 | 950.7108 |
| 988.5306 | 1018.5908 | 1021.5312 | 1081.5950 | 1088.4804 | 1154.6793 |
| 1457.7506 | 1491.7937 | 1502.7706 | 1560.8159 | 1563.7089 | 1675.8092 |

Protein I 292

| | | | | | |
|---|---|---|---|---|---|
| 881.3373 | 1168.6586 | 1189.6091 | 1205.6194 | 1263.6377 | 1419.7204 |
| 1487.7331 | 1545.7266 | 1547.7188 | 1576.8979 | 1625.8683 | 1638.8148 |
| 1687.8336 | 1819.8460 | 1851.8649 | 1940.8958 | 1977.9077 | 1987.9647 |
| 2082.9463 | 2536.1013 | | | | |

Protein I 408

| | | | | | |
|---|---|---|---|---|---|
| 679.4761 | 728.5525 | 796.4827 | 1037.5187 | 1062.5377 | 1090.5288 |
| 1126.4991 | 1172.5254 | 1193.5959 | 1234.6704 | 1256.6646 | 1263.6611 |
| 1349.7196 | 1371.7023 | 1393.7119 | 1397.7314 | 1434.7747 | 1458.7111 |
| 1636.9152 | 1638.8883 | 1657.7814 | 1838.9477 | 1851.8797 | 1940.9565 |
| 2034.0037 | 2367.2130 | 2399.0118 | | | |

Protein I 418

| | | | | | |
|---|---|---|---|---|---|
| 964.5183 | 1037.5627 | 1064.5737 | 1137.6832 | 1172.5764 | 1192.6737 |
| 1235.6392 | 1250.6431 | 1263.6860 | 1269.7053 | 1297.6467 | 1343.8145 |
| 1351.6546 | 1434.8046 | 1682.0241 | 1766.8335 | 1780.9714 | 1794.9118 |
| 1810.1236 | 1833.9644 | 1881.9621 | 2010.0111 | 2490.2406 | |

Protein I 683

| | | | | | |
|---|---|---|---|---|---|
| 679.4642 | 686.4822 | 728.5341 | 740.4581 | 754.4010 | 831.5268 |
| 908.6695 | 922.6996 | 924.6633 | 927.5649 | 942.6207 | 944.6316 |
| 950.7218 | 964.7080 | 966.7058 | 989.5694 | 1027.7101 | 1057.5632 |
| 1077.7748 | 1126.5526 | 1129.7359 | 1131.7469 | 1192.6919 | 1209.6791 |
| 1235.5576 | 1267.7130 | 1299.9801 | 1335.9426 | 1427.7586 | 1454.7041 |
| 1459.7211 | 1545.7712 | 1560.8588 | 1562.8589 | 1586.8190 | 1648.8764 |
| 1670.9380 | 1724.8275 | 1940.9525 | 1948.9614 | 1975.9984 | |

Protein I 961

| | | | | | |
|---|---|---|---|---|---|
| 759.3961 | 890.4867 | 897.4147 | 973.4941 | 984.5204 | 1010.5798 |
| 1121.5470 | 1181.5950 | 1213.5632 | 1234.6504 | 1263.6617 | 1398.6162 |
| 1414.6316 | 1415.7328 | 1424.6398 | 1434.7767 | 1445.7310 | 1458.6971 |
| 1483.7347 | 1527.7932 | 1558.8253 | 1561.8434 | 1568.7826 | 1601.7848 |
| 1614.8114 | 1657.8223 | 1837.9453 | 1859.9258 | 1930.8506 | 1940.9234 |
| 2510.0925 | | | | | |

Protein I 8264

| | | | | | |
|---|---|---|---|---|---|
| 642.5045 | 658.5016 | 686.4927 | 728.5465 | 740.4921 | 774.4709 |
| 780.5196 | 831.5513 | 865.5687 | 867.5099 | 869.6086 | 873.5823 |
| 894.6489 | 908.7021 | 922.6901 | 924.6790 | 936.6994 | 942.6411 |
| 944.6494 | 950.7201 | 964.6993 | 966.7231 | 984.7021 | 1027.7337 |
| 1033.8070 | 1077.7870 | 1113.7539 | 1115.7545 | 1119.7935 | 1129.7573 |
| 1131.7649 | 1165.7695 | 1167.7520 | 1172.7909 | 1299.9896 | 1316.0267 |
| 1333.9461 | 1335.9603 | 1342.0281 | 1427.7685 | 1454.7054 | 1521.0357 |
| 1523.0652 | 1562.8953 | 1724.8181 | 2131.0723 | | |

Protein I 8311

| | | | | | |
|---|---|---|---|---|---|
| 850.5019 | 856.5146 | 869.4636 | 918.4998 | 944.5313 | 969.5587 |
| 1057.5591 | 1067.6079 | 1126.5398 | 1194.6171 | 1211.6538 | 1225.6115 |
| 1234.6546 | 1259.6481 | 1390.7952 | 1547.8033 | 1574.8037 | 1940.9446 |

NEPHGE Proteins
Protein N 68

| | | | | | |
|---|---|---|---|---|---|
| 934.5011 | 973.5176 | 995.5134 | 1037.4985 | 1057.5457 | 1067.5389 |
| 1090.5301 | 1165.5666 | 1193.6021 | 1201.6298 | 1234.6758 | 1254.6088 |
| 1263.6946 | 1357.7112 | 1372.7550 | 1383.6956 | 1434.7743 | 1493.7441 |
| 1838.9202 | | | | | |

Protein N 212

| | | | | | |
|---|---|---|---|---|---|
| 679.4801 | 728.5553 | 754.4194 | 831.5235 | 856.5218 | 870.5557 |
| 908.6769 | 922.7039 | 942.6525 | 944.6679 | 950.7372 | 964.7121 |
| 966.7143 | 976.5887 | 984.7234 | 1025.6127 | 1029.5839 | 1057.5669 |
| 1077.7906 | 1094.5759 | 1125.6473 | 1263.6958 | 1266.7342 | 1274.7816 |
| 1277.7181 | 1281.6434 | 1299.9767 | 1306.6874 | 1314.8066 | 1367.8446 |
| 1425.7379 | 1427.7699 | 1437.8714 | 1545.7752 | 1659.8590 | 1940.9373 |

Protein N 268

| | | | | | |
|---|---|---|---|---|---|
| 1127.5909 | 1143.0754 | 1150.0510 | 1179.6245 | 1263.6834 | 1329.7091 |
| 1342.7220 | 1377.7676 | 1389.7560 | 1398.7576 | 1448.7888 | 1469.7860 |
| 1488.7963 | 1537.7106 | 1545.7932 | 1567.7595 | 1652.8691 | 1822.9858 |
| 1888.9980 | 1907.0101 | 1940.9455 | 1997.8974 | 2091.0940 | 2123.0874 |
| 2483.2269 | 2536.1216 | 3039.3320 | 3131.4566 | 3191.3283 | |

Protein N 403

| | | | | | |
|---|---|---|---|---|---|
| 832.4770 | 909.4422 | 923.4959 | 944.5214 | 976.4972 | 1013.4648 |
| 1036.4942 | 1125.4947 | 1158.5404 | 1188.5988 | 1232.5625 | 1248.5905 |
| 1263.6708 | 1328.6698 | 1350.6660 | 1527.7290 | 1545.7385 | 1687.9345 |
| 1695.7709 | | | | | |

Protein N 435

| | | | | | |
|---|---|---|---|---|---|
| 1033.5528 | 1036.5348 | 1146.5669 | 1219.6851 | 1234.6535 | 1263.6714 |
| 1270.7097 | 1350.6636 | 1416.7296 | 1434.7634 | 1444.7664 | 1469.7677 |
| 1510.6958 | 1545.7626 | 1592.7967 | 1645.9039 | 1687.9633 | 1859.9505 |
| 2025.9711 | | | | | |

TABLE 3-continued

Molecular weights of the tryptic peptide fragments of novel proteins for which spectra were obtained but for which no match existed in the current databases.

| Protein N 509 | | | | | |
|---|---|---|---|---|---|
| 832.4913 | 908.6967 | 944.6603 | 950.7336 | 1111.6071 | 1125.5858 |
| 1127.5990 | 1142.5584 | 1143.5936 | 1175.6808 | 1204.5361 | 1263.7111 |
| 1337.6739 | 1340.7881 | 1378.7656 | 1652.8528 | 1688.0168 | |
| Protein N 1355 | | | | | |
| 834.5078 | 864.5228 | 880.4829 | 930.4477 | 1112.6013 | 1127.7663 |
| 1165.5930 | 1167.6745 | 1223.7230 | 1233.6671 | 1305.7169 | 1326.8050 |
| 1338.6753 | 1364.7585 | 1367.7510 | 1382.6926 | 1433.8208 | 1467.8768 |
| 1501.9072 | 1580.7527 | 1582.8264 | 1634.8417 | 1758.3905 | 1762.9243 |
| 1768.9738 | 1797.9604 | 2033.9419 | | | |

These values are given in Daltons as obtained from the mass spectrometer, Known tolerances for these values will be known to anyone skilled in the art. Peptides from trypsin, keratin and other common contaminating proteins have been removed.

REFERENCES

1. Gepts W: Pathologic anatomy of the pancreas in juvenile diabetes mellitus. Diabetes 14:619-633,1965
2. Junker K, Egeberg J, Kromann H, Nerup J: An Autopsy Study of the Islets of Langerhans in Acute Onset Juvenile Diabetes Mellitus. Acta Pathologica Et Microbiologica scandinavica Section a Pathology 85:699-706,1977
3. Nerup J, Mandrup-Poulsen T, Helqvist S, Andersen H U, Pociot F, Reimers J I, Cuartero B G, Karisen A E, Bjerre U, Lorenzen T: On the pathogenesis of IDDM. Diabetologia 37 (suppl 2):S82-89,1994
4. Corbett J A, McDaniel M L: Intraisiet release of interleukin 1 inhibits p cell expression of inducible nitric oxide synthase. J Exp Med 181:559-568,1995
5. Mandrup-Poulsen T: The role of interleukin-1 in the pathogenesis of insulin-dependent diabetes mellitus. Diabetologia 39:1005-1029,1996
6. Lortz S, Tiedge M, Nachtwey T, Karisen A, Nerup J, lenzen S: Protection of insulin-producing RINm5F cells against cytokine-mediated toxicity through overexpression of antioxidant enzymes. Diabetes 49:1123-1130, 2000
7. Mose Larsen P, Fey S J, Larsen M R, Nawrocki A, Andersen H U, Kähler H, Heilmann M C V, Roepstorff P, Pociot F, Karisen A E, Nerup J: Proteome analysis of IL-1β induced changes in protein expression in rat islets of Langerhans. Diabetes 50:1056-1063, 2001
8. Bone A J: Animal models of type I diabetes, Current Opinion in Oncologic, Endocrine and Metabolic Investigational Drugs 2:192-200, 2000
9. Nakhooda A F, Uke A A Chappel C I, Murray F T, Marliss E B: The spontaneously diabetic Wistar rat. Metabolic and morphologic studies. Diabetes 26:100-112,1977
10. Andersen H U, Mandrup-Poulsen T, Egeberg J, Helqvist S, Nerup J: Genetically determined differences in newborn rat islet sensitivity to interleukin-1 in vitro: no association with the diabetes prone phenotype in the BB-rat. Acta endocrinologica 120:92-98,1989
11. Reimers J T, Andersen H U, Mauricio D, Pociot F, A. E. K, Petersen J S, Mandrup-Poulsen T, Nerup J: Strain dependent differences in sensitivity of rat beta-cells to IL-1 beta in vitro and in vivo: Association with islet nitric oxide synthesis. Diabetes 45:771-778,1996
12. Bellmann K, Hui L, Radons J, Burkart V, Kolb H: Low stress response enhances vulnerability of islet cells in diabetes-prone BB rats. Diabetes 46:232-236,1997
13. Christensen U B, Larsen P M, Fey S J, Andersen H U, Nawrocki A, Sparre-T., Mandrup-Poulsen T, Nerup J: Islet protein expression changes during diabetes development in islet syngrafts in BB-DP rats and during rejection of BB-DP islet allografts. Autoimmunity 32:1-15, 2000
14. Andersen H U, Fey S J, Mose Larsen P, Nawrocki A, Hejnaes K R, Mandrup-Poulsen T, Nerup J:Interlieukin-1 beta induced changes in the protein expression of rat islets. Electrophoresis 18:2091-2103, 1997
15. Brunstedt J, Nielsen J H, Lemmark A, and The Hagedom Study Group: Isolation of islets from mice and rats, in Methods in diabetes research, (Laboratory methods, part C) (vol 1), edited by Larner J, Pohl S L, New York, Wiley & Sons, 1984, pp 254-288
16. O'Farrell P Z, Goodman H M, O'Farrell P H: High resolution two dimentional electrophoresis of basic as well as acidic proteins. Cell 12:1133-1142,1977
17. Fey S J, Nawrocki A, Larsen M R, Gorg A, Roepstorff P, Skews G N, Williams R. Larsen P M: Proteome analysis of Saccharomyces cerevisiae: a methodological outline. Electrophoresis 18:1361-1372,1997
18. Fey S J, Mose Larsen P, Biskjaer N: The protein variation in basal cells and certain basal cell related benign and malignant diseases, Faculty of Natural Science, University of Arhus, Denmark, 1984
19. Rosenfeld J, Capdevielle J, Guillemot J C, Ferrara P: In-gel digestion of proteins for internal sequence analysis after one- or two-dimensional gel electrophoresis. Anal. Biochem 203:173-179, 1992
20. Shovchenko A, Wilm M, Vorm O, Mann M: Mass spectrometric sequencing of proteins from silver stained polyacrylamide gels. Anal. Chem 68:850-858,1996
21. Nawrocki A, Larsen M R, Podtelejnikov A V, Jensen O N, Mann M, Roepstorff P, Gorg A, Fey S J, Mose-Larsen P: Correlation of acidic and basic, ampholyte and immobilised pH gradient 2D gel patterns based on mass spectrometric identification. Electrophoresis 19:1024-1035, 1998
22. Kussmnann M, Nordhoff E, Nielsen H R, Haebel S, Larsen M R, Jacobsen L, Jensen C, Gobom J, Mirgorodskaya E, Kristensen A K, Palm L, Roepstorff P: MALDI-MS sample preparation techniques designed for various peptide and protein analytes. Journal of Mass Spectrometry 32:593-601,1997
23. Mann M, Højrup P, Roepstorff P: Use of Mass Spectrometric Molecular Weight Information to Identify Proteins in Sequence Databases. Biol. Mass Spectrom 22:338-345, 1993
24. Jensen O N, Larsen M R, Roepstorff P: Mass spectrometric identification and microcharacterization of proteins from electrophoretic gels: Strategies and applications. Proteins: Structure, Function and Genetics 33:74-89,1998
25. Asayama K, Kooy N W, Burr I M: Effect of vitamin R deficiency and selenium deficiency on insulin secretory reserve and free radical scavenging systems in islets: decrease of islet manganosuperoxide dismutase. Journal of laboratory and clinical medicine 107:459-464,1986
26. Sumoski W, Paquerizo H, Rahinovitch A: Oxygen Free Racal Scavengers Protect Rat Islet Cells from Damage by Cytokines. Diabetologia 32:792-796,1989
27. Welsh N, Bendtzen K, Sandler S: Influence of protease on inhibitory and stimulatory effects of interleukin 1 beta on beta-cell function. Diabetes 40:290-294,1991

28. Andersen H U, Larson P M, Fey S J, Karisen A E, Mandrup-Poulsen T, Nerup J: Two-dimensional gel electrophoresis of rat islet proteins. Interleukin 1 beta-induced changes in protein expression are reduced by L-arginine depletion and nicotinamide. Diabetes 44:400-407,1995

29. Helqvist S, Pola S S, Johannesen J, Nerup J: Heat shock protein induction in rat pancreatic islets by recombinant human interleukin 1 beta. Diabetologia 34:150-156,1991

30. Borg L A H, Cagliero E, Sandler S, Welsh N, Eizirik D L: Interleukin-1β increases the activity of superoxide dismutase in rat pancreatic islets. Endocrinology 130: 2851-2857, 1992

31. Corbett J A, Lancaster J R, Sweetland M A, McDaniel M L: Interleukin-1 beta-induced formation of EPR-detectable iron-nitrosyl complexes in islets of Langerhans. Role of nitric oxide in interleukin1 beta-induced inhibition of insulin secretion. Journal of biological chemistry 266:21351-21354, 1991

32. Welsh N, Elzirik D L, Bendtzen K, Sandler S: Interlieukin-1 beta-induced nitric oxide production in isolated rat pancreatic islets requires gene transcription and may lead to inhibition of the Krebs cycle enzyme aconitase. Endocrinology 129:3167-3173.1991

33. Blamonto G, Ruggiu M, Sacoone S, Dellavalle G, Rive S: 2 homologous genes, originated by duplication, encode the human hnmp protein-a2 and protein-a1. Nucleic Acids Research 22:1996-2002,1994

34. Dater K V, Dreyfuss G, Swanson M S: The human hnRNP M proteins: identification of a methionine/arginine-rich repeat motif in ribonucleoproteins. Nucleic acids research 21:439-446,1993

35. Elzirik D L, Bjorklund A, Welsh N: Interleukin-1-induced expression of nitric oxide synthase in insulin-producing cells is preceded by cabs induction and depends on gene transcription and protein synthesis. FEBS letters 311: 62-66,1993

36. Chen M C, Schuit F, Pipeleers D G, Elzirik D L: IL-1beta induces serine protease inhibitor 3 (SPI3) gene expression in rat pancreatic beta-cells. Detection by differential display of messenger RNA. Cytokine 11:856-862,1999

37. Spinas G A, Hansen B S, Linde S, Kastem W, Molvig J, Mandrup-Poulsen T, Dinarello C A, Nielsen J H, Nerup-I.: Interleukin 1 dose-dependently affects the biosynthesis of (pro)insulin in isolated rat islets of Langerhans. Diabetologia 30:474-480,1987

38. Riera M, Roher N, Miro F, Gil C, Trujillo R, Aguilera J, Plana M, Itade E: Association of protein kinase CK2 with eukalyotic translation initiation factor eIF-2 and with grp94/ndoplasmin. Molecular and Cellular Biochemistry 191:97-104,1999

39. Ramakrishnan M, Schonthai A H, LeeS: Endoplasmic reticulum stress-inducible protein GRP94 is associated with an Mg+-dependent serine kinase activity modulated by Ca2+ and GRP78/BiP. Journal of Cellular Physiology 170:115-129,1997

40. Hendershot I-M, Valentine V A, Lee A S, Morris S W, Shapiro D N: Localization of the gene encoding human BiP/GRP78, the endoplasmic reticulum cognate of the HSP70 family, to chromosome 9q34. Genomics 20:281-284,1994

41. Oliver J D, van-der W, F. J., Bulleid N J, High S: Interaction of the thiol-dependent reductase ERp57 with nascent glycoproteins. Science 275:86-88,1997

42. Nakamura M, Yamanobe T, Suyemitsu T, Komukal M, Kan R, Okinaga S, Aral K. A new membrane associated Ca(2+)-binding protein of rat spermatogenic cells: its purification and characterization. Biochemical and biophysical research communications 176:1358-1364,1991

43. Bellmann K, Jaattela M, Wissing D, Burkad V, Kolb H: Heat shock protein hsp70 overexpression confers resistance against nitric oxide. FEBS letters 391:185-188,1996

44. Scarim A L, Heitmeier M R. Corbett J A: Heat shock inhibits cytokine-induced nitric oxide synthase expression by rat and human islets. Endocrinology 139:5050-5057, 1998

45. Ankarcrona M, Dypbukt J M, Brune S, Nicotera P: Interleukin-1 beta-induced nitric oxide production activates apoptosis in pancreatic RINm5F cells. Experimental cell research 213:172-177, 1994

46. Vassilladis S, Dragiotis V, Protopapadakis E, Athanassakis I, Mitlianga P, Konidads K, Papadopoulos G K: The destructive action of IL-1alpha and IL-1beta in IDDM is a multistage process: evidence and confirmation by apoptotic studies, induction of intermediates and electron microscopy. Mediators of inflammation 8:85-91,1999

47. Kaneto H, Fujii J, Seo H G, Suzuki K, Matsuoka T, Nakamura M, Tatsumi H, Yamasaki Y, Kamada T, Taniguchi N: Apoptotic cell-death triggered by nitric-oxide in pancreatic beta-cell Diabetes 44:733-738,1995

48. Lotz M M, Andrews C W, Korzelius C A, Lee E C, Steele G D, Clarke A, Mercurio A M: Decreased expression of Mac-2 (carbohydrate binding protein 35) and loss of its nuclear localization are associated with the neoplastic progression of colon carcinoma. Proceedings of the National Academy of Sciences of the United States of America 90:3466-3470,1993

49. Hsu D K, Dowling C A, Jeng K C G, Chen J T, Yang R Y, Liu F T: Galectin-3 expression is induced in cirrhotic liver and hepatocellular carcinoma. International Journal of Cancer 81:519-526,1999

50. Karisen A E, Andersen H U, Larsen P M, Fey S J, Larsen M, Pociot F, Whitmore T, Nielsen K, Nerup J: Galectin-3, a lectin involved in cytokine-mediated beta-cell destruction and IDDM? Diabetologia 40:A35,1997

51. Sudo K, Takahashi E, Nakamura Y: Isolation and mapping of the human EIFAZ gene homologous to the murine protein synthesis initiation factor 4A-II gene Eif4a2. Cytogenetics and cell genetics 71:385-388,1995

52. Minturn J E, Fryer H J, Geschwind D H, Hockfield S: TOAD-64, a gene expressed early in neuronal differentiation in the rat, is related to unc-33, a C, elegans gene involved in axon outgrowth. Journal of neuroscience 15:6757-6766,1995

53. Wagner L, Oliyamyk O, Gartner W, Nowotny P, Groeger M, Kaserer K, Waldhausi W, Pasternack M S: Cloning and expression of secretagogin, a novel neuroendocrine- and pancreatic islet of Langerhans-specific Ca2+-binding protein. Journal of Biological Chemistry 275:24740-24751, 2000

54. Rabinovitch A, Suarez-Pinzon W, Strynadka K, Sooy K, Chrisakos S: Calbindin-D28k overexpression prevents cytokine-induced apoptosis in pancreatic islet beta-cells. Diabetes 48:A427-428,1999

55. Burns K, Duggan B, Atkinson E A, Famulski K S, Nemer M, Bleackley R C, Michalak M: Modulation of gene expression by calreticulin binding to the glucocorticoid receptor. Nature 367:476-480,1994

56. Dedhar S, Ronnie P S, Shago M, Hagesteijn C Y, Yang H, Filmus J, Hawley R G, Bruchovsky N, Cheng H, Matusik R J: Inhibition of nuclear hormone receptor activity by calreticulin. Nature 1367:480-483,1994

57. Shimizu S, Narita M, Tsujimoto Y: Bcl-2 family proteins regulate the release of apoptogenic cytochrome c by the mitochondrial channel VDAC. Nature 399:483-487, 1999
58. Tiedge M, Lortz S, Munday I R, Lenzen S: Protection against the co-operative toxicity of nitric oxide and oxygen free radicals by overexpression of antioxidant enzymes in bioengineered insulin producing RINm5F cells. Diabetologia 42:849-855,1999
59. Goth L, Eaton J W: Hereditary catalase deficiencies and increased risk of diabetes. Lancet (North American Edition) 356:1820-1821, 2000
60. Meister A, Anderson M E: Glutathione. Annual review of biochemistry 52:711-760,1983
61. Uhlig S, Wendel A: The physiological consequences of glutathione variations. Life sciences 51:1083,1094,1992
62. Casanova M L, Bravo A, Ramirez A, Morreale-de E, G, Were F, Medino G, Vidal M, Jorcano J L: Exocrine pancreatic disorders in transgenic mice expressing human keratin 8. Journal of clinical investigation 103:1587-1595, 1999
63. Selmin O, Lucier G W, Gark G C, Tritscher A M, Vanden-Heuvel J P, Gastel J A, Walker N J, Sutter T R, Bell D A: Isolation and characterization of a novel gene induced by 2,3,I,8-tetrachlorodibenzo-p-dioxin in rat liver. Carcinogenesis 17:2609-2615,1996
64. Oppermann U C, Salim S, Tjernberg L O, Terenius L, Jornvall H: Binding of amyloid beta-peptide to mitochondrial hydroxyacyl-CoA dehydrogenase (ERAB): regulation of an SDR enzyme activity with implications for apoptosis in Alzheimer's disease. FEBS letters 451:238-242,1999
65. Sandford G R, Ho K, Burns W H: Characterization of the major locus of immediate-early genes of rat cytomegalovirus. Journal of virology 67:4093-4103,1993
66. Lahm H W, Langen H: Mass spectrometry: A toot for the identification of proteins separated by gels. Electrophoresis 21:2105-2114, 2000
67. Rabinovitch A, Suarez-Pinzon W I., Sorensen O, Bleackley R C: Inducible nitric oxide synthase (INOS) in pancreatic islets of nonobese diabetic mice: Identification of INOS-expressing cells and relationships to cytokines expressed in the islets. Endocrinology 137:2093-2099, 1996
68. Christensen U, Spare T, Cooke A, Andersen H, Mandrup-Poulsen T, Nerup J: Syngeneic islet transplantation in prediabetic BB-DP rats-a synchronized model for studying beta-cell destruction during the development of IDDM. Autoimmunity 28:91-107,1998
69. Sparre T, Christensen U B, Larsen P M, Fey S J, Karisen A E, Pociot F, Gotfredsen C, Richter B, Mandrup-Poulsen T, Nerup J: Dynamic changes in protein expression in syngeneic islet transplants during IDDM development in DP-BB rats. Diabetologia 41:A157,1998

The invention claimed is:

1. A method for diagnosing diabetes in a mammal, wherein the method comprises determining decreased level of expression of mitochondrial precursor of ATP synthase alpha chain, in a biological sample from said mammal selected from the group consisting of urine, blood, saliva, lymphatic fluids, and tissue.

2. A method according to claim 1, wherein the tissue is pancreatic tissue.

3. A method for determining the predisposition in a human for diabetes, the method comprising
determining decreased level of expression of
mitochondrial precursor of ATP synthase alpha chain, in a biological sample originating from the human selected from the group consisting of urine, blood, saliva, lymphatic fluids, and tissue.

4. The method of claim 1, wherein the level of expression of the mitochondrial precursor of ATP synthase alpha chain is determined by measuring the amount of binding to an antibody for said mitochondrial precursor of ATP synthase alpha chain.

5. The method according to claim 4, wherein the antibody is a polyclonal antibody.

6. The method according to claim 4, wherein the antibody is a monoclonal antibody.

* * * * *

UNITED STATES PATENT AND TRADEMARK OFFICE
CERTIFICATE OF CORRECTION

PATENT NO. : 7,279,274 B2
APPLICATION NO. : 10/960652
DATED : October 9, 2007
INVENTOR(S) : Larsen et al.

It is certified that error appears in the above-identified patent and that said Letters Patent is hereby corrected as shown below:

Col. 4, line 8: "Daltons for LEE protein" should read --Daltons for IEF protein--

Col. 4, line 46: "FIGS. 13b-13C" should start a new paragraph

Col. 17, line 55: "terms "nucleic acidd fragment" and" should read --terms "nucleic acid fragment" and--

Col. 20, line 54: "Cl/mmol, containing 0.1%" should read --Ci/mmol, containing 0.1%--

Col. 24, line 22: "(http://www.ncbi.nim.nih.aovg through" should read --(http://www.ncbi.nim.nih.gov) through--

Col. 33, line 19: "Welsh N, Elzirik D L," should read --Welsh N, Eizirik D L,--

Signed and Sealed this

Seventeenth Day of June, 2008

JON W. DUDAS
*Director of the United States Patent and Trademark Office*